United States Patent [19]

Higashii et al.

[11] Patent Number: 5,693,251
[45] Date of Patent: Dec. 2, 1997

[54] OPTICALLY ACTIVE BENZENE DERIVATIVES, PROCESS FOR PRODUCING THE SAME AND LIQUID-CRYSTALLINE COMPOSITION CONTAINING SAID DERIVATIVES AS LIQUID-CRYSTALLINE COMPOUND AND LIGHT SWITCHING ELEMENTS

[75] Inventors: Takayuki Higashii, Kishiwada; Isao Kurimoto, Toyonaka; Shoji Toda, Takarazuka; Masayoshi Minai, Moriyama; Takeshi Tani, Tsukuba; Chizu Kawakami, Tsukuba; Koichi Fujisawa, Tsukuba, all of Japan

[73] Assignee: Sumitomo Chemical Company, Limited, Osaka, Japan

[21] Appl. No.: 347,117

[22] Filed: Nov. 23, 1994

Related U.S. Application Data

[62] Division of Ser. No. 912,130, Jul. 9, 1992, Pat. No. 5,389,293, which is a continuation of Ser. No. 815,914, Jan. 2, 1992, abandoned, which is a continuation of Ser. No. 410,263, Sep. 21, 1989, abandoned.

[30] Foreign Application Priority Data

| Sep. 22, 1988 | [JP] | Japan | 63-238091 |
| Sep. 22, 1988 | [JP] | Japan | 63-238092 |
| Sep. 22, 1988 | [JP] | Japan | 63-238094 |
| Oct. 13, 1988 | [JP] | Japan | 63-258938 |
| Oct. 18, 1988 | [JP] | Japan | 63-263748 |
| Apr. 25, 1989 | [JP] | Japan | 1-106659 |
| May 30, 1989 | [JP] | Japan | 1-138333 |

[51] Int. Cl.$^6$ .................... C09K 19/12; C07C 67/02; C07C 41/00
[52] U.S. Cl. ................ 252/299.66; 25/299.65; 568/660; 568/661; 568/662; 560/179; 560/184; 560/186; 560/187; 560/188; 560/227; 560/228; 560/254; 560/255
[58] Field of Search .................... 560/179, 184, 560/186, 187, 188, 227, 228, 254, 255, 129; 568/660, 661, 662; 252/299.65, 299.66

[56] References Cited

U.S. PATENT DOCUMENTS

| 4,744,918 | 5/1988 | Heppke et al. | |
| 4,780,241 | 10/1988 | Furukawa et al. | |
| 4,834,904 | 5/1989 | Krause et al. | |
| 4,876,026 | 10/1989 | Saito et al. | |
| 4,882,084 | 11/1989 | Ohno et al. | 252/299.66 |
| 4,911,863 | 3/1990 | Sage et al. | |
| 4,973,426 | 11/1990 | Ohno et al. | |
| 4,980,082 | 12/1990 | Ohba et al. | |
| 5,047,172 | 9/1991 | Saito et al. | 252/299.61 |
| 5,236,618 | 8/1993 | Heppke et al. | 252/299.61 |
| 5,238,598 | 8/1993 | Kurimoto et al. | 568/661 |
| 5,389,293 | 2/1995 | Higashii et al. | 252/299.61 |

FOREIGN PATENT DOCUMENTS

| 0021636 | 1/1981 | European Pat. Off. |
| 0175591 | 3/1986 | European Pat. Off. |
| 0255219 | 2/1988 | European Pat. Off. |
| 0255962 | 2/1988 | European Pat. Off. |
| 0259995 | 3/1988 | European Pat. Off. |
| 0267758 | 5/1988 | European Pat. Off. |
| 0270243 | 6/1988 | European Pat. Off. |
| 0277815 | 8/1988 | European Pat. Off. |
| 0357435 | 3/1990 | European Pat. Off. |
| 2304763 | 8/1974 | Germany. |
| 61-195187 | 8/1986 | Japan. |
| 63-48270 | 2/1988 | Japan. |
| 63-135346 | 6/1988 | Japan. |
| 63-165344 | 7/1988 | Japan. |
| 8705012 | 8/1987 | WIPO. |

OTHER PUBLICATIONS

Chemical Abstracts 112:46255W, vol. 112, 1990.
Schuster et al., Chemical Abstracts 64: 17379d, Abstract of J. Am. Chem. Soc. 88(8), pp. 1722–1731, (1966).
Patent Abstracts of Japan, vol. 12, No. 258 (C–513)[3105] 20 Jul. 1988, p. 99 C 513 & JP-A-63 44 551 (Canon Inc.).
Patent Abstracts of Japan, vol. 13, No. 313 (C–618)[3661] 17 Jul. 1989, & JP-A-1 96 153 (Dainippon Ink & Chem., Inc.).
Patent Abstracts of Japan, vol. 14, No. 96 (C–692)[4039] 22 Feb. 1990, & JP-A-1 305 055 (Sumitomo Chem., Co., Ltd.).
Tetrahedron Letters No. 49, pp. 4783–4786 (1979), Pergamon Press Ltd. (GB), L. Bin Din et al.: "Nucleophilic Reactions In . . . ".
Tetrahedron Letters, vol. 25, No. 45, pp. 5129–5132 (1984) Pergamon Press Ltd. (GB), M.J. Cook et al.: "Rotational . . . ".

*Primary Examiner*—Philip Tucker
*Attorney, Agent, or Firm*—Watson Cole Stevens Davis, P.L.L.C.

[57] ABSTRACT

An optically active phenol useful in the preparation of liquid crystalline compounds which is represented by the formula (V):

$$HO-Z'-O-\left(\overset{O}{\underset{\|}{C}}\right)_s-R_2 \quad (V)$$

wherein $R_2$ represents an alkyl or alkoxyalkyl group having 1 to 20 carbon atoms optionally substituted by halogen atoms; Z' represents $$-\left(\!\!\!\bigcirc\!\!\!\right)_l\!\!-(CH_2)_q\!-\overset{CH_3}{\underset{*}{C}H}-$$

or $$-\left(\!\!\!\bigcirc\!\!\!\right)_l\!\!-\overset{CH_3}{\underset{*}{C}H}-(CH_2)_t-$$

wherein q represents a number of 1 to 5 and * indicates asymmetric carbon atom; l represents a number of 2; t represents a number of 1 to 5; s represents a number of 0 or 1.

7 Claims, No Drawings

OPTICALLY ACTIVE BENZENE DERIVATIVES, PROCESS FOR PRODUCING THE SAME AND LIQUID-CRYSTALLINE COMPOSITION CONTAINING SAID DERIVATIVES AS LIQUID-CRYSTALLINE COMPOUND AND LIGHT SWITCHING ELEMENTS

This is a division of application Ser. No. 07/912,130, filed Jul. 9, 1992; now U.S. Pat. No. 5,389,293, which in turn is a continuation of application Ser. No. 07/815,914, filed Jan. 2, 1992, now abandoned; which in turn is a continuation of application Ser. No. 07/410,263, filed Sep. 21, 1989, now abandoned.

This invention relates to the optically active benzene derivatives represented by the general formula (I):

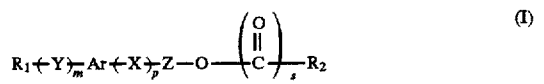

(wherein $R^1$ represents an alkyl group having 3 to 20 carbon atoms; Y represents —O—, —COO— or —OCO—; m, p and s each represents a number of 0 or 1; Ar represents

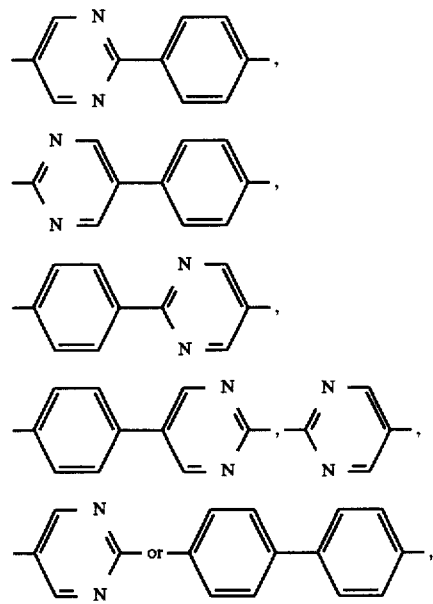

provided that when p is 1 Ar represents

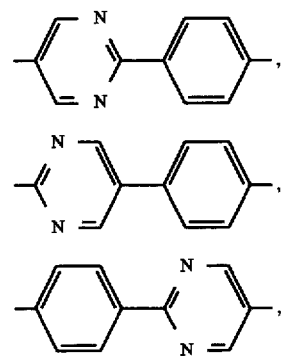

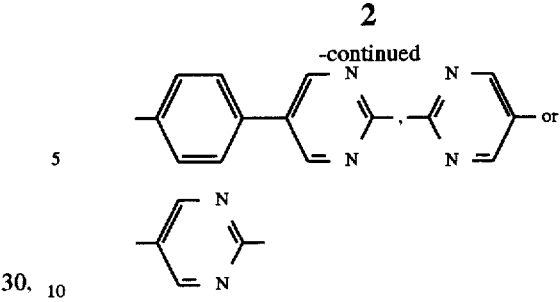

when p is 0 Ar represents

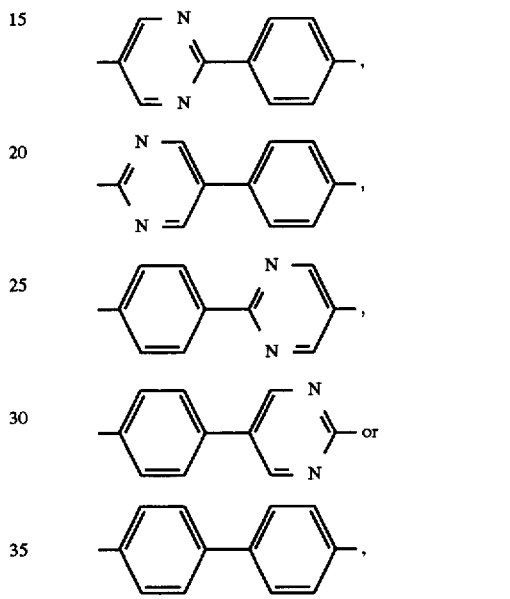

X represents —COO— or —OCO—; Z represents

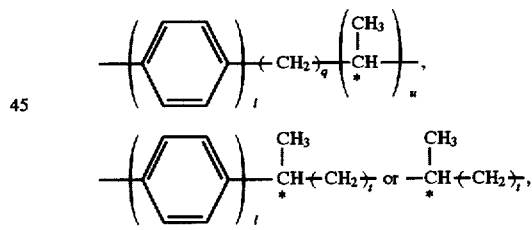

wherein q represents a number of 1 to 5, t represents a number of 0 to 5, 1 represents a number of 1 or 2, u represents a number of 0 or 1 and * indicates asymmetric carbon atom; provided that when Ar represents

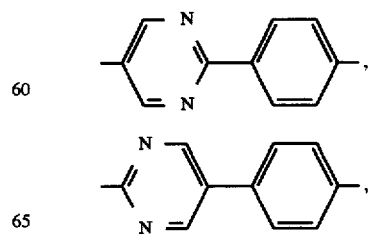

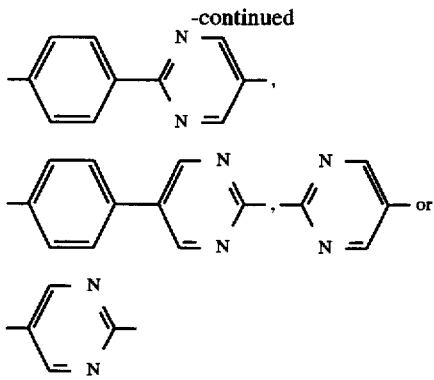

Z represents

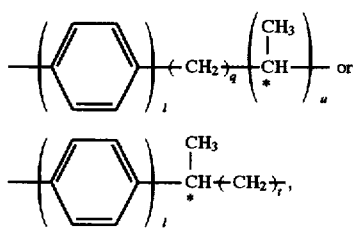

when P is 0 Z represents

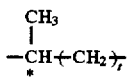

with the proviso that when t is 0 Ar represents

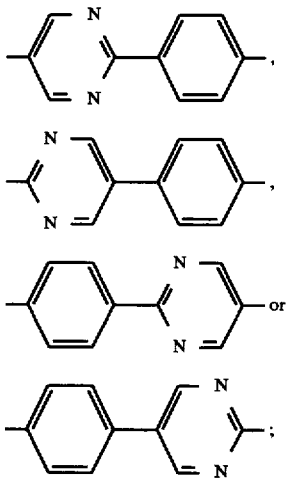

$R_2$ represents an alkyl or alkoxyalkyl group having 1 to 20 carbon atoms optionally substituted by halogen atoms; provided that when u is 0 $R_2$ represents an optically active alkyl or alkoxyalkyl group having 1 to 20 carbon atoms optionally substituted by halogen atoms), a process for producing the same, liquid-crystalline composition containing said derivatives as liquid-crystalline compound, and light switching elements utilizing the liquid crystal compositions containing said derivatives.

The term "liquid-crystalline compound" is used in this specification to refer to the liquid-crystalline compound of the broad sense, including those which may not have been confirmed to take a liquid crystal phase per se but can be utilized effectively as a liquid crystal composition.

Image display devices using liquid crystal are now practically used in various fields. TN (twisted nematic) type liquid crystal display is known as one of these display systems. This display system has the advantages that its power consumption is low and it is soft to the eye because of the light-receiving type (the display panel itself is not luminous). Display by this system, however, is not always satisfactory in the aspect of response speed.

As a system which is capable of high speed response, a display device utilizing the optical switching performance of ferroelectric liquid crystal has been proposed (Applied Physics Letters, 36, 899 (1980)) and is attracting attention.

In view of its molecular configuration, ferroelectric liquid crystal is considered to belong to the type of liquid crystal having chiral smectic C phase (hereinafter referred to as $S_C^*$ phase) or chiral smectic H phase ($S_H^*$ phase). With its high speed response characteristics, such ferroelectric liquid crystal is expected to find its use not only for display devices such as liquid crystal televisions but also as materials for electronic elements such as optical printer head, photo-Fourier transformation element, etc.

A ferroelectric liquid crystal material to be used in a ferroelectric liquid crystal indicating element practically utilized is required to have a number of characteristics, however, at present, one kind of compound singly can not satisfy these requirements, thus, it is necessary to use a ferroelectric liquid crystal composition obtained by mixing several kinds of liquid crystal compounds or non-liquid crystal compounds.

Further, in addition to the ferroelectric liquid crystal composition comprising ferroelectric liquid crystal compounds only, Japanese Unexamined Patent Publication No. 195187/1986 has reported that a compound and a composition exhibiting a phase of smectic C, F, G, H or I which is non-chiral (hereinafter abbreviated as a phase of Sc or the like) are used as basic substances and one kind or plural kinds of compounds exhibiting a ferroelectric liquid crystal phase are mixed with the above substance to obtain a liquid crystal composition which is ferroelectric as a whole. Further, there has been found a report that compounds and compositions exhibiting a phase of Sc or the like are used as basic substances and one kind or plural kinds of compounds which are optically active but exhibit no ferroelectric liquid crystal phase are mixed therewith to make them a ferroelectric liquid crystal composition as a whole (Mol. Cryst. Liq. Cryst. 89. 327 (1982).

Summarizing the above described, it is understood that one kind or plural kinds of compounds which are optically active, irrespectively of the compounds exhibiting a ferroelectric liquid crystal phase or not, can be mixed with basic substances to constitute a ferroelectric liquid crystal composition. However, it is preferable that the optically active substances desirably exhibit a liquid crystal phase, and even if they exhibit no liquid crystal phase, they preferably have a structure similar to a liquid crystal substance, namely, they are preferably the so-called pseudo liquid crystal substance.

However, there has yet been found no liquid crystal material which shows spontaneous polarization necessary for high-speed response and liquid crystal properties in the low temperature region.

In view of the above, the present inventors have made studies for developing a liquid crystal compound which can be widely applied to various types of display systems such as mentioned above, and as a result they found out novel optically active benzene derivatives and achieved the present invention.

The present invention provides the novel optically active benzene derivatives represented by the above-described general formula (I). Such optically active benzene derivatives have been unknown in the prior art and disclosed for the first time by the present inventors.

The compounds representing by the formula (I-a),

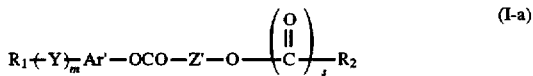  (I-a)

(wherein $R_1$, $R_2$, Y, m and s have the meanings given above; Ar' represents

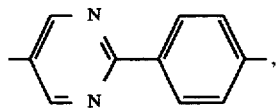

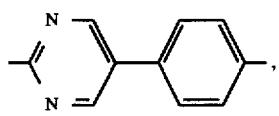

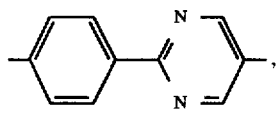

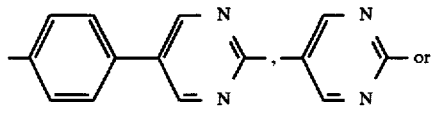 or

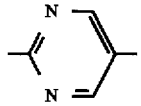

Z' represents

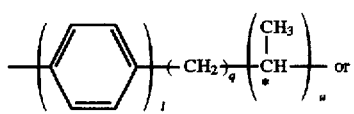

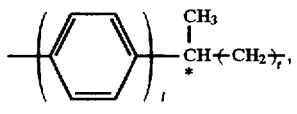

wherein l, q, t, u and * have the same meanings given above), which are one of such novel derivatives can be produced, for instance, by reacting the phenols represented by the formula (II):

  (II)

(wherein $R_1$, Y, Ar' and m have the meanings given above) with optically active carboxylic acid compounds represented by the formula (III):

  (III)

wherein Z', $R_2$ and s have the meanings given above and R' represents a hydroxyl group or a halogen atom.

The novel compounds representing by the formula (I-b):

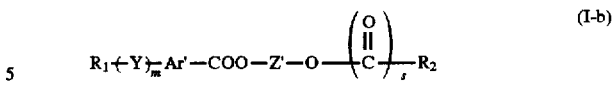  (I-b)

(wherein $R_1$, $R_2$, Y, Ar', Z', m and s have the meanings given above), which are one of said novel derivatives can be produced, for instance, by reacting aromatic carboxylic acids represented by the formula (IV):

  (IV)

(wherein $R_1$, Y, Ar' and m have the meanings given above and R' represents a hydroxyl group or a halogen atom) with optically active phenols represented by the formula (V):

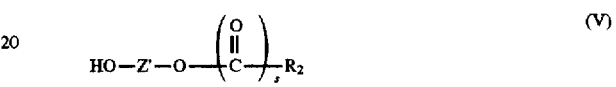  (V)

wherein Z', $R_2$ and s have the meanings given above.

The compounds representing by the formula (I-c):

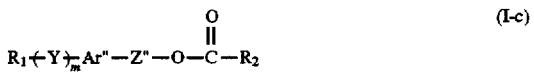  (I-c)

(wherein $R_1$, $R_2$, Y and m have the meanings given above; Z" represents

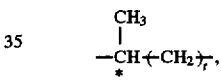

wherein t represents a number of 0 to 5 and * indicates asymmetric carbon atom; and Ar" represents

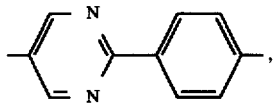

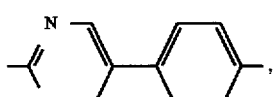

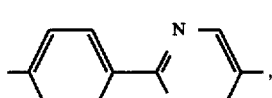

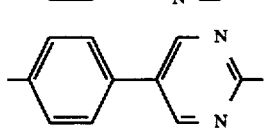

or

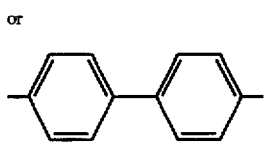

with the proviso that when t=0, Ar" represents

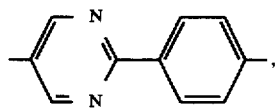,

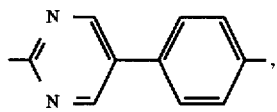,

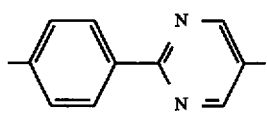

or

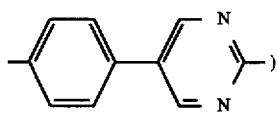)

can be produced, for instance, by reacting optically active aromatic alcohols represented by the formula (VI):

$$R_1\!-\!(Y)_m\!-\!Ar"\!-\!Z"\!-\!OH \qquad (VI)$$

(wherein $R_1$, Y, Ar", Z" and m have the meanings given above) with carboxylic acids and the derivatives thereof represented by the formula (VII):

$$\underset{R'-C-R_2}{\overset{O}{\|}} \qquad (VII)$$

wherein $R_2$ have the meanings given above and R' represents a hydroxyl group or a halogen atom.

The compounds represented by the formula (I-d):

$$R_1\!-\!(Y)_m\!-\!Ar"\!-\!Z"\!-\!O\!-\!R_2 \qquad (I\text{-}d)$$

(wherein $R_1$, Y, Ar", Z", $R_2$ and m have the meanings given above) which are last one of said novel derivatives can be produced, for instance, by reacting optically active aromatic alcohols represented by the formula (VI):

$$R_1\!-\!(Y)_m\!-\!Ar"\!-\!Z"\!-\!OH \qquad (VI)$$

(wherein $R_1$, Y, Ar", Z" and m have the meanings given above) with alkylating reagents represented by the formula (IX):

$$Q\!-\!R_2 \qquad (IX)$$

wherein $R_2$ have the meanings given above; Q represents a halogen atom or $-OSO_2R'''$ wherein R''' represents a lower alkyl group or a phenyl group optionally substituted by alkyl groups.

The optically active carboxylic acid compounds (III) containing asymmetric carbon, which are used as starting material in the above reactions, can be produced, for instance, (a) t or q=1–5 and s=0.

ⓑ S = 1

ⓑ S=1

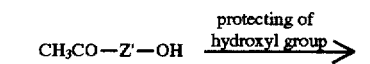

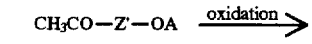

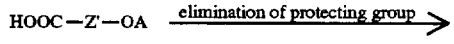

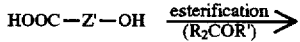

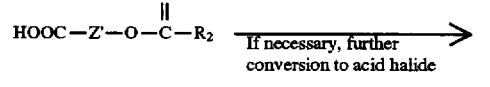

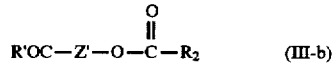

(In the above reaction formulae, A represents a protecting group such as benzyl, t-butyldimethylsilyl or tetrahydropyranyl group.)

ⓒ t=0

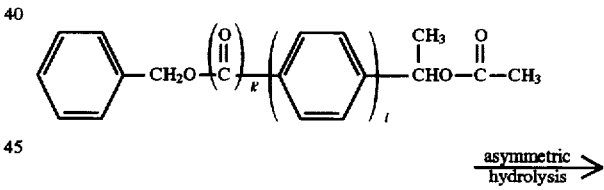

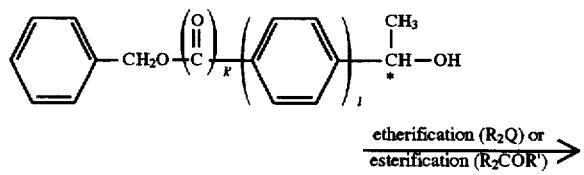

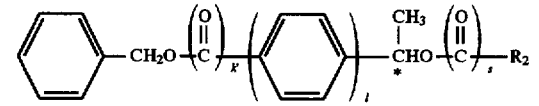

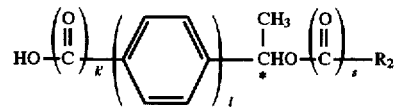

(In the above reaction formulas, k' represents a number of 1.)

The optically active phenols (V) containing asymmetric carbon, which are used as starting material in the above reactions, can be produced, for instance,

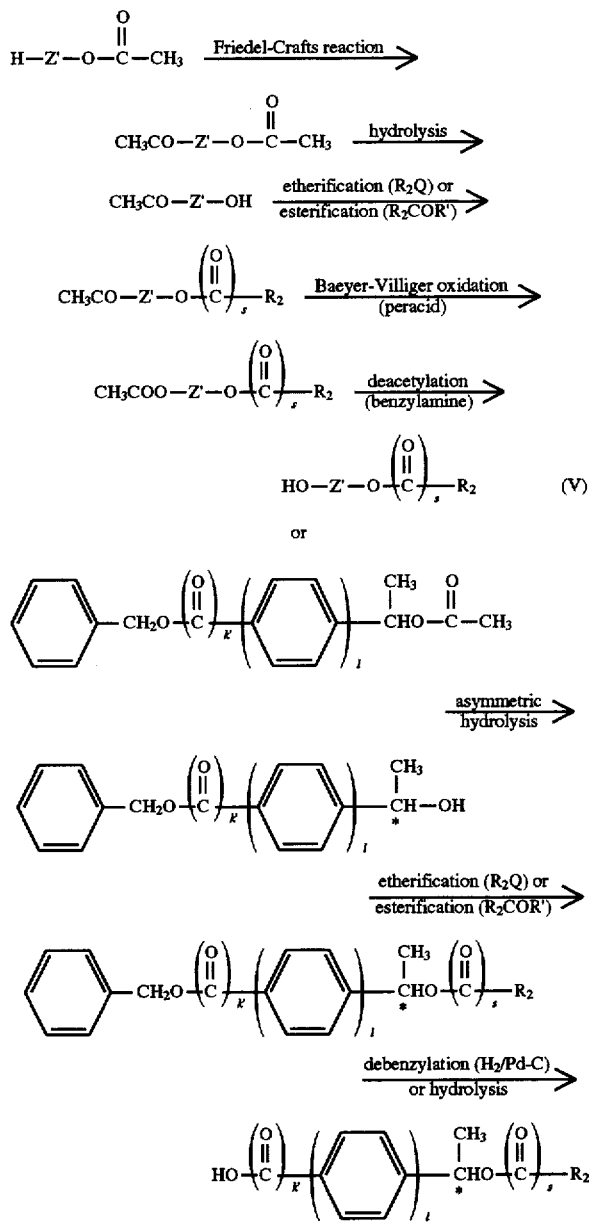

(In the above reaction formulas, k represents a number of 0.)

The optically active aromatic alcohols (VI) containing asymmetric carbon, which are used as starting material in the above reactions, can be produced, for instance, (a) t=0

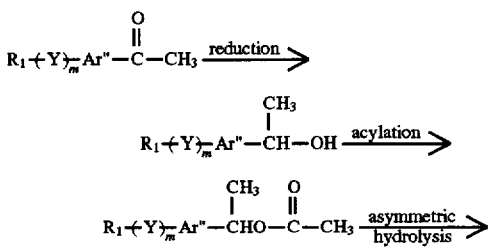

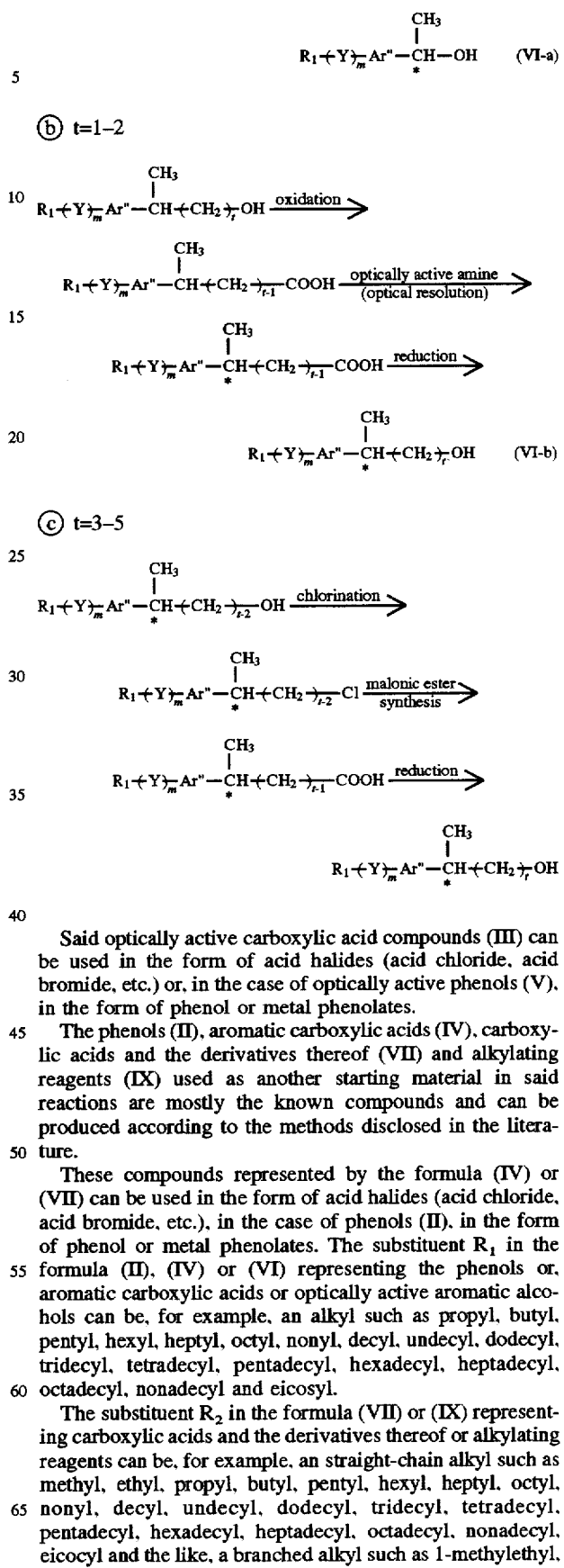

Said optically active carboxylic acid compounds (III) can be used in the form of acid halides (acid chloride, acid bromide, etc.) or, in the case of optically active phenols (V), in the form of phenol or metal phenolates.

The phenols (II), aromatic carboxylic acids (IV), carboxylic acids and the derivatives thereof (VII) and alkylating reagents (IX) used as another starting material in said reactions are mostly the known compounds and can be produced according to the methods disclosed in the literature.

These compounds represented by the formula (IV) or (VII) can be used in the form of acid halides (acid chloride, acid bromide, etc.), in the case of phenols (II), in the form of phenol or metal phenolates. The substituent $R_1$ in the formula (II), (IV) or (VI) representing the phenols or, aromatic carboxylic acids or optically active aromatic alcohols can be, for example, an alkyl such as propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl and eicosyl.

The substituent $R_2$ in the formula (VII) or (IX) representing carboxylic acids and the derivatives thereof or alkylating reagents can be, for example, an straight-chain alkyl such as methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicocyl and the like, a branched alkyl such as 1-methylethyl, 2-methylbutyl, 3-methylpentyl, 4-methylhexyl, 5-methylheptyl, 6-methyloctyl, 1-methylpropyl, 1-methylbutyl, 1-methylpentyl, 1-methylhexyl, 2-ethylbutyl, 1-methylheptyl, 2,3-dimethylbutyl, 2,3,3-trimethylbutyl, 2-methylpentyl, 2,3-dimethylpentyl, 2,4-dimethylpentyl, 2,3,3,4-tetramethylpentyl, 2-methylhexyl, 3-methylhexyl, 2,5-dimethylhexyl, 2-methylheptyl, 2-methyloctyl, 2-trihalomethylpentyl, 2-trihalomethylhexyl, 2-trihalomethylheptyl, 2-halopropyl, 3-halo-2-methylpropyl, 2,3-dihalopropyl, 2-halobutyl, 3-halobutyl, 2,3-dihalobutyl, 2,4-dihalobutyl, 3,4-dihalobutyl, 2-halo-3-methylbutyl, 2-halo-3,3-dimethylbutyl, 2-halopentyl, 3-halopentyl, 4-halopentyl, 2,4-dihalopentyl, 2,5-dihalopentyl, 2-halo-3-methylpentyl, 2-halo-4-methylpentyl, 2-halo-3-monohalomethyl-4-methylpentyl, 2-halohexyl, 3-halohexyl, 4-halohexyl, 5-halohexyl, 2-haloheptyl, 2-halooctyl ("halo" in the alkyl group described above represents fluorine, chlorine, bromine or iodine), and the like, or an alkyloxyalkyl such as methoxymethyl, methoxyethyl, methoxypropyl, methoxybutyl, methoxypentyl, methoxyhexyl, methoxyheptyl, methoxyoctyl, methoxynonyl, methoxydecyl, ethoxymethyl, ethoxyethyl, ethoxypropyl, ethoxybutyl, ethoxypentyl, ethoxyhexyl, ethoxyheptyl, ethoxyoctyl, ethoxynonyl, ethoxydecyl, propoxymethyl, propoxyethyl, propoxypropyl, propoxybutyl, propoxypentyl, propoxyhexyl, propoxyoctyl, propoxydecyl, butoxymethyl, butoxyethyl, butoxypropyl, butoxybutyl, butoxypentyl, butoxyhexyl, butoxyheptyl, butoxynonyl, pentyloxymethyl, pentyloxyethyl, pentyloxypropyl, pentyloxybutyl, pentyloxypentyl, pentyloxyoctyl, pentyloxydecyl, hexyloxymethyl, hexyloxyethyl, hexyloxypropyl, hexyloxybutyl, hexyloxypentyl, hexyloxyhexyl, hexyloxyoctyl, hexyloxynonyl, hexyloxydecyl, heptyloxymethyl, heptyloxyyethyl, heptyloxypropyl, heptyloxypentyl, octyloxymethyl, octyloxyethyl, decyloxymethyl, decyloxyethyl, decyloxypropyl and the like. In said branched alkyls, the branching carbon may be optically active one.

Further, the substituent R₂ in the optically active carboxylic acid compounds (III) or the optically active phenols (V) may include those exemplified below (however, in case where u=0, an optically active group having an asymmetric carbon atom is used):

methyl, ethyl, propyl, butyl, pentyl, hexyl, heptyl, octyl, nonyl, decyl, undecyl, dodecyl, tridecyl, tetradecyl, pentadecyl, hexdecyl, heptadecyl, octadecyl, nonadecyl, eicocyl, methoxymethyl, methoxyethyl, methoxypropyl, methoxybutyl, methoxypentyl, methoxyhexyl, methoxyheptyl, methoxyoctyl, methoxynonyl, methoxydecyl, ethoxymethyl, ethoxyethyl, ethoxypropyl, ethoxybutyl, ethoxypentyl, ethoxyhexyl, ethoxyheptyl, ethoxyoctyl, ethoxynonyl, ethoxydecyl, propoxymethyl, propoxyethyl, propoxypropyl, propoxybutyl, propoxypentyl, propoxyhexyl, propoxyheptyl, propoxyoctyl, propoxydecyl, butoxymethyl, butoxyethyl, butoxypropyl, butoxybutyl, butoxypentyl, butoxyhexyl, butoxyheptyl, butoxyoctyl, butoxynonyl, butoxydecyl, pentyloxymethyl, pentyloxyethyl, pentyloxypropyl, pentyloxybutyl, pentyloxypentyl, pentyloxyhexyl, pentyloxyoctyl, pentyloxydecyl, hexyloxymethyl, hexyloxyethyl, hexyloxypropyl, hexyloxybutyl, hexlhexypentyl, hexyloxyhexyl, hexyloxyoctyl, hexyloxynonyl, hexyloxydecyl, heptyloxymethyl, heptyloxyethyl, heptyloxypropyl, heptyloxybutyl, heptyloxypentyl, octyloxymethyl, octyloxyethyl, ctyloxypropyl, decyloxymethyl, decyloxyethyl, decyloxypropyl, 1-methylethyl, 1-methylpropyl, 1-methylbutyl, 1-methylpentyl, 1-methylhexyl, 1-methylheptyl, 1-methyloctyl, 2-methylethyl, 2-methylbutyl, 2,3-dimethylbutyl, 2,3,3-trimethylbutyl, 2-methylpentyl, 3-methylpentyl, 2,3-dimethylpentyl, 2,4-dimethylpentyl, 2,3,3,4-tetarmethylpentyl, 2-methylhexyl, 3-methylhexyl, 4-methylhexyl, 2,5-dimethylhexyl, 2-methylheptyl, 2-methyloctyl, 2-trihalomethylpentyl, 2-trihalomethylhexyl, 2-trihalomethylheptyl, 2-haloethyl, 2-halopropyl, 3-halopropyl, 3-halo-2-methylpropyl, 2,3-dihalopropyl, 2-halobutyl, 3-halobutyl, 4-halobutyl, 2,3-dihalobutyl, 2,4-dihalobutyl, 3,4-dihalobutyl, 2-halo-3-methylbutyl, 2-halo-3,3-dimethylbutyl, 2-halopentyl, 3-halopentyl, 4-halopentyl, 2,4-dihalopentyl, 2,5-dihalopentyl, 5-halopentyl, 2-halo-3-methylpentyl, 2-halo-4-methylpentyl, 2-halo-3-monohalomethyl-4-methylpentyl, 2-halohexyl, 3-halo-hexyl, 4-halohexyl, 5-halohexyl, 6-halohexyl, 2-haloheptyl and 2-halooctyl ("halo" in the alkyl group described above represents fluorine, chlorine, bromine or iodine).

Further, in case where s=1, there may be mentioned, in addition to those above mentioned, halomethyl, 1-haloethyl, 1-halopropyl, 1-halobutyl, 1-halopentyl, 1-halohexyl, 1-halo-heptyl, 1-halooctyl, etc.

Meanwhile, those which are capable of becoming optical active among the alkyl groups or alkoxyalkyl groups which may be substituted with a halogen atom may be an optically active group.

An ordinary esterification method can be applied for the reaction of phenols (II) and optically active carboxylic acid compounds (III), the reaction of aromatic carboxylic acids (IV) and optically active phenols (V) or the reaction of optically active aromatic alcohols (VI) and carboxylic acids (VII) and the derivatives thereof, and such reaction can be carried out in the presence or absence of a solvent by using a catalyst.

In case of using a solvent in these reactions, such solvent is selected from those which are inert to the reaction, such as aliphatic or aromatic hydrocarbons, ethers, halogenated hydrocarbons and the like, the typical examples thereof being tetrahydrofuran, ethyl ether, acetone, methyl ethyl ketone, toluene, benzene, chlorobenzene, dichloromethane, dichloroethane, chloroform, carbon tetarchloride, dimethylformamide, hexane and the like. These solvents may be used either singly or in combination. No specific limitations are imposed on the amount of such solent(s) used.

Since the optically active carboxylic acid compounds (III), the optically active phenols (V) and the optically active aromatic alcohols (VI) used in the reaction are expensive, it is advisable to use the other starting material, viz. phenols (II), aromatic carboxylic acids (IV) or carboxylic acids (VII) and the derivatives thereof, in an excess amount, usually 1 to 4 equivalents, preferably 1 to 2 equivalents to the optically active compound (III), (V) or (VI).

As the catalyst, there can be used organic or inorganic basic materials such as dimethylaminopyridine, triethylamine, tri-n-butylamine, pyridine, picoline, collidine, imidazole, sodium carbonate, sodium methylate, potassium hydrogencarbonate and the like.

Organic or inorganic acids such as toluenesulfonic acid, methanesulfonic acid, sulfuric acid, etc., are also usable as catalyst.

It is also possible to use a condensing reagent in the case of dehydration for the carboxylic acids and phenols.

As the condensing reagent, there can be used organic materials such as N,N'-dicyclohexyl carbodiimide, N-cyclohexyl-N'-(4-diethylamino)cyclohexyl carbodiimide, imidazoylimidazole and the like.

If necessary there can be used organic amines such as 4-pyrrolidinopyridine, pyridine, triethylamine and the like.

The amount of a condensing reagent is usually 1 to 1.2 equivalents to the carboxylic acid.

The amount of organic amine is usually 0.01 to 0.2 equivalent to a condensing reagent.

The amount of the catalyst to be used is not specified as it varies depending on the type of the starting materials used, their combination with the catalyst used and other factors, but in case of using an acid halide as a starting material, a basic material is used as catalyst in an amount not less than one equivalent to said acid halide.

The reaction temperature is usually −30° to 100° C.

The reaction time is not subject to any specific limitations.

After the reaction has been completed, the reaction product is subjected to the ordinary separating means such as extraction, separation of liquid phase, concentration, etc., to isolate the objective optically active benzene derivative of the formula (I-a), (I-b) and (I-c). If necessary, the product may be purified by column chromatography, recrystallizaiton or other means.

In the above reaction, as the carboxylic acids (VII) and the derivatives thereof may be used, in addition to the substituents $R_2$ described above, aliphatic carboxylic acids having halomethyl, 1-haloethyl, 1-halopropyl, 1-halobutyl, 1-halopentyl, 1-halohexyl, 1-haloheptyl, 1-halooctyl group or acid anhydrides thereof or acid halides thereof such as acid chlorides and acid bromides thereof.

These aliphatic carboxylic acids or derivatives thereof may be either of a racemic modification and an optically active one.

Some of the optically active carboxylic acids described above can be obtained by oxidation of the corresponding alcohols or reductive deamination of amino acids. Further, some of them exist in nature, or can be derived from the following optically active amino acids and optically active oxyacids obtained by optical resolution:

alanine, valine, leucine, isoleucine, phenylalanine, cerin, threonine, allothreonine, homocerin, alloisoleucine, tertleucine, 2-aminobutyric acid, norvaline, norleucine, ornithine, lysine, hydroxylysine, phenylglycine, trifluoroalanine, aspartic acid glutamic acid, lactic acid, mandelic acid, tropic acid, 3-hydroxybutyric acid, malic acid, tartaric acid, isopropylmalic acid, etc. An ordinary etherification method can be applied for the reaction of optically active aromatic alcohols (VI) and alkylating reagents (IX), and such reaction can be carried out in the presence of a solvent by using a basic substance.

As the basic substance, there may be exemplified, for example, an alkaline metal hydride such as sodium hydride and potassium hydride, an alkaline metal such as lithium, sodium and potassium, an alkaline metal alcoholate such as sodium ethylate and sodium methylate, an alkaline metal carbonate such as sodium carbonate and potassium carbonate; lithium butyl and the like.

The amount of the above basic substance required is one equivalent amount or more and preferably within the range of 1 to 5 equivalent amounts relative to the optically active alcohols, although the upper limit thereof is not particularly limited.

Alkylating reagents (IX) to be used in this reaction are halides such as a chloride, a bromide, an iodide and the like or sulfates (methanesulfonic ester, ethanesulfonic ester, benzene sulfonic ester, toluenesulfonic ester and the like) having an alkyl group or an alkoxyalkyl group of 1 to 20 carbon atoms, which may be substituted with a halogen atom, as exemplified as the above.

These alkyl group or alkoxyalkyl group of 1 to 20 carbon atoms which may optionally be substituted with a halogen atom may be an optically active group.

These halides or sulfates having an optically active group are derived from the corresponding alcohols, and some of the optically active alcohols can easily be obtained by asymmetric reduction of the corresponding ketones with an asymmetric metal catalyst, a microorganism or an enzyme. Some of the alcohols exist in nature or can be derived from the following optically active amino acids and optically active oxy acids obtainable by optical resolution:

valine, leucine, isoleucine, phenylalanine, threonine, allothreonine, homocerin, alloisoleucine, tert-leucine, 2-aminobutyric acid, norvaline, norleucine, ornithine, lysine, hydroxylysine, phenylglycine, aspartic acid, glutamic acid, mandelic cid, toropic acid, 3-hydroxybutyric acid, malic acid, tartaric acid, isopropylmalic acid and the like.

The amount of such an alkylating agent (IX) used is not limited so long as it is one equivalent amount or more and usually within the range of 1 to 5 equivalent amounts relative to the optically active aromatic alcohols (VI).

As the reaction solvent, in addition to the above exemplified solvents, polar solvents such as dimethylsulfoxide, hexamethyl triamide phosphate, N-methylpyrrolidone and the like can be used.

The reaction temperature may be usually −50° C. to 120° C., preferably within the range of −30° C. to 100° C.

After completion of the reaction, optically active benzene derivatives of the general formula (I-d) can be obtained in a good yield according to the ordinary separation methods such as procedures of extraction, separation, concentration and the like, and if necessary, derivatives can be purified by column chromatography, recrystallization and the like.

Specific examples of optically active benzene derivatives (I-c) and (I-d) are shown below.

5-[4-{1-Alkyl(of 1 to 20 carbon atoms) carbonyloxyethyl}phenyl]-2-alkyl(of 3 to 20 carbon atoms) pyrimidine, 5-[4-{1-Alkyl(of 1 to 20 carbon atoms) carbonyloxyethyl}phenyl]-2-alkyl(of 3 to 20 carbon atoms) oxypyrimidine, 5-[4-{1-Alkyl(of 1 to 20 carbon atoms) carbonyloxyethyl}phenyl]-2-alkyl(of 3 to 20 carbon atoms) carbonyloxypyrimidine, 5-[4-{1-Alkyl(of 1 to 20 carbon atoms) carbonyloxyethyl}phenyl]-2-alkyl(of 3 to 20 carbon atoms) oxycarbonylpyrimidine, 2-{1-Methyl-2-alkyl(of 1 to 20 carbon atoms) carbonyloxyethyl}-5-{4-alkyl(of 3 to 20 carbon atoms) phenyl}pyrimidine, 2-{1-Methyl-2-alkyl(of 1 to 20 carbon atoms) carbonyloxyethyl}-5-{4-alkyl(of 3 to 20 carbon atoms) oxyphenyl}pyrimidine, 2-{1-Methyl-2-alkyl(of 1 to 20 carbon atoms) carbonyloxyethyl}-5-{4-alkyl(of 3 to 20 carbon atoms) carbonyloxyphenyl}pyrimidine, 2-{1-Methyl-2-alkyl(of 1 to 20 carbon atoms) carbonyloxyethyl}-5-{4-alkyl(of 3 to 20 carbon atoms) oxycarbonylphenyl}pyrimidine, 5-{1-Methyl-2-alkyl(of 1 to 20 carbon atoms) carbonyloxyethyl}-2-{4-alkyl(of 3 to 20 carbon atoms) phenyl}pyrimidine, 5-{1-Methyl-2-alkyl(of 1 to 20 carbon atoms) carbonyloxyethyl}-2-{4-alkyl(of 3 to 20 carbon atoms) oxyphenyl}pyrimidine, 5-{1-Methyl-2-alkyl(of 1 to 20 carbon atoms)carbonyloxyethyl}-2-{4-alkyl(of 3 to 20 carbon atoms)carbonyloxyphenyl}pyrimidine, 5-{1-Methyl-2-alkyl(of 1 to 20 carbon atoms)carbonyloxyethyl}-2-{4-alkyl(of 3 to 20 carbon atoms)oxycarbonylphenyl}pyrimidine, 4-{1-Methyl-2-alkyl(of 1 to 20 carbon atoms)carbonyloxyethyl}-4'-{4-alkyl(of 3 to 20 carbon atoms)}biphenyl, 4-{1-Methyl-2-alkyl(of 1 to 20 carbon atoms)carbonyloxyethyl}-4'-{4-alkyl(of 3 to 20 carbon atoms)oxy}biphenyl, 4-{1-Methyl-2-alkyl(of 1 to 20 carbon atoms)carbonyloxyethyl}-4'-{4-alkyl(of 3 to 20 carbon atoms)oxycrbonyl}biphenyl 4-{1-Methyl-2-alkyl(of 1 to 20 carbon atoms)carbonyloxyethyl}-4'-{4-alkyl(of 3 to 20 carbon atoms)carbonyloxy}biphenyl 2-[4-{1-Methyl-2-alkyl(of 1 to 20 carbon atoms)carbonyloxyethyl}phenyl]-5-alkyl(of 3 to 20 carbon atoms)pyrimidine, 2-[4-{1-Methyl-2-alkyl(of 1 to 20 carbon atoms)carbonyloxyethyl}phenyl]-5-alkyl(of 3 to 20 carbon atoms)oxypyrimidine, 2-[4-{1-Methyl-2-alkyl(of 1 to 20 carbon atoms)carbonyloxyethyl}phenyl]-5-alkyl(of 3 to 20 carbon atoms)carbonyloxypyrimidine, 2-[4-{1-Methyl-2-alkyl(of 1 to 20 carbon atoms)carbonyloxyethyl}phenyl]-5-alkyl(of 3 to 20 carbon atoms)oxycarbonylpyrimidine, 5-[4-{1-Methyl-2-alkyl(of 1 to 20 carbon atoms)carbonyloxyethyl}phenyl]-2-alkyl(of 3 to 20 carbon atoms)pyrimidine, 5-[4-{1-Methyl-2-alkyl(of 1 to 20 carbon atoms)carbonyloxyethyl}phenyl]-2-alkyl(of 3 to 20 carbon atoms)oxypyrimidine, 5-[4-{1-Methyl-2-alkyl(of 1 to 20 carbon atoms)carbonyloxyethyl}phenyl]-2-alkyl(of 3 to 20 carbon atoms)carbonyloxypyrimidine, 5-[4-{1-Methyl-2-alkyl(of 1 to 20 carbon atoms)carbonyloxyethyl}phenyl]-2-alkyl(of 3 to 20 carbon atoms)oxycarbonylpyrimidine, 2-{1-Alkyl(of 1 to 20 carbon atoms)oxyethyl}-5-{4-alkyl(of 3 to 20 carbon atoms)phenyl}pyrimidine, 2-{1-Alkyl(of 1 to 20 carbon atoms)oxyethyl}-5-{4-alkyl(of 3 to 20 carbon atoms)oxyphenyl}pyrimidine, 2-{1-Alkyl(of 1 to 20 carbon atoms)oxyethyl}-5-{4-alkyl(of 3 to 20 carbon atoms)carbonyloxyphenyl}pyrimidine, 2-{1-Alkyl(of 1 to 20 carbon atoms)oxyethyl}-5-{4-alkyl(of 3 to 20 carbon atoms)oxycarbonylphenyl}pyrimidine, 2-{1-Alkyl(of 1 to 20 carbon atoms)carbonyloxyethyl}-5-{4-alkyl(of 3 to 20 carbon atoms)phenyl}pyrimidine, 2-{1-Alkyl(of 1 to 20 carbon atoms)carbonyloxyethyl}-5-{4-alkyl(of 3 to 20 carbon atoms)oxyphenyl}pyrimidine, 2-{1-Alkyl(of 1 to 20 carbon atoms)carbonyloxyethyl}-5-{4-alkyl(of 3 to 20 carbon atoms)carbonyloxyethyl}-5-{4-alkyl(of 3 to 20 carbon atoms)oxycarbonylphenyl}pyrimidine, 5-{1-Alkyl(of 1 to 20 carbon atoms)oxyethyl}-2-{4-alkyl(of 3 to 20 carbon atoms)phenyl}pyrimidine, 5-{1-Alkyl(of 1 to 20 carbon atoms)oxyethyl}-2-{4-alkyl(of 3 to 20 carbon atoms)oxyphenyl}pyrimidine, 5-{1-Alkyl(of 1 to 20 carbon atoms)oxyethyl}-2-{4-alkyl(of 3 to 20 carbon atoms)carbonyloxyphenyl}pyrimidine, 5-{1-Alkyl(of 1 to 20 carbon atoms)oxyethyl}-2-{4-alkyl(of 3 to 20 carbon atoms)phenyl}pyrimidine, 5-{1-Alkyl(of 1 to 20 carbon atoms)oxyethyl}-2-{4-alkyl(of 3 to 20 carbon atoms)oxyphenyl}pyrimidine, 5-{1-Alkyl(of 1 to 20 carbon atoms)oxyethyl}-2-{4-alkyl(of 3 to 20 carbon atoms)carbonylphenyl}pyrimidine, 5-{1-Alkyl(of 1 to 20 carbon atoms)oxycarbonylphenyl}pyrimidine, 2-[4-{1-Alkyl(of 1 to 20 carbon atoms)oxyethyl}phenyl]-5-alkyl(of 3 to 20 carbon atoms)pyrimidine, 2-[4-{1-Alkyl(of 1 to 20 carbon atoms)oxyethyl}phenyl]-5-alkyl(of 3 to 20 carbon atoms)oxypyrimidine, 2-[4-{1-Alkyl(of 1 to 20 carbon atoms)oxyethyl}phenyl]-5-alkyl(of 3 to 20 carbon atoms)carbonyloxypyrimidine, 2-[4-{1-Alkyl(of 1 to 20 carbon atoms)oxyethyl}phenyl]-5-alkyl(of 3 to 20 carbon atoms)oxycarbonyloxypyrimidine, 2-[4-{1-Alkyl(of 1 to 20 carbon atoms)carbonyloxyethyl}phenyl]-5-alkyl(of 3 to 20 carbon atoms)pyrimidine, 2-[4-{1-Alkyl(of 1 to 20 carbon atoms)carbonyloxyethyl}phenyl]-5-alkyl(of 3 to 20 carbon atoms)oxypyrimidine, 2-[4-{1-Alkyl(of 1 to 20 carbon atoms)carbonyloxyethyl}phenyl]-5-alkyl(of 3 to 20 carbon atoms)carbonyloxypyrimidine, 2-[4-{1-Alkyl(of 1 to 20 carbon atoms)carbonyloxyethyl}phenyl]-5-alkyl(of 3 to 20 carbon atoms)oxycarbonylpyrimidine, 5-[4-{1-Alkyl(of 1 to 20 carbon atoms)oxyethyl}phenyl]-2-alkyl(of 3 to 20 carbon atoms)pyrimidine, 5-[4-{1-Alkyl(of 1 to 20 carbon atoms)oxyethyl}phenyl]-2-alkyl(of 3 to 20 carbon atoms)oxypyrimidine, 5-[4-{1-Alkyl(of 1 to 20 carbon atoms)oxyethyl}phenyl]-2-alkyl(of 3 to 20 carbon atoms)carbonyloxypyrimidine, 5-[4-{1-Alkyl(of 1 to 20 carbon atoms)oxyethyl}phenyl]-2-alkyl(of 3 to 20 carbon atoms)oxycarbonylpyrimidine, 2-{1-Methyl-2-alkyl(of 1 to 20 carbon atoms)oxyethyl}-5-{4-alkyl(of 3 to 20 carbon atoms)oxyphenyl)pyrimidine, 2-{1-Methyl-2-alkyl(of 1 to 20 carbon atoms)oxyethyl}-5-{4-alkyl(of 3 to 20 carbon atoms)carbonyloxyphenyl}pyrimidine, 2-{1-Methyl-2-alkyl(of 1 to 20 carbon atoms)oxyethyl}-5-{4-alkyl(of 3 to 20 carbon atoms)oxycarbonylphenyl}pyrimidine, 4-{1-Methyl-2-alkyl(of 1 to 20 carbon atoms)oxyethyl}-4'-{4-alkyl(of 3 to 20 carbon atoms)biphenyl, 4-{1-Methyl-2-alkyl(of 1 to 20 carbon atoms)oxyethyl}-4'-{4-alkyl(of 3 to 20 carbon atoms)oxy}biphenyl, 4-{1-Methyl-2-alkyl(of 1 to 20 carbon atoms)oxyethyl}-4'-{4-alkyl(of 3 to 20 carbon atoms)carbonyloxy}biphenyl, 4-{1-Methyl-2-alkyl(of 1 to 20 carbon atoms)oxyethyl}-4'-{4-alkyl(of 3 to 20 carbon atoms)oxycarbonyl}biphenyl, 5-{1-Methyl-2-alkyl(of 1 to 20 carbonatoms)oxyethyl}-2-{4-alkyl(of 3 to 20 carbonatoms)phenyl}pyrimidine, 5-{1-Methyl-2-alkyl(of 1 to 20 carbonatoms)oxyethyl}-2-{4-alkyl(of 3 to 20 carbonatoms)oxyphenyl}pyrimidine, 5-{1-Methyl-2-alkyl(of 1 to 20 carbonatoms)oxyethyl}-2-{4-alkyl(of 3 to 20 carbonatoms)carbonyloxyphenyl}pyrimidine, 5-{1-Methyl-2-alkyl(of 1 to 20 carbonatoms)oxyethyl}-2-{4-alkyl(of 3 to 20 carbonatoms)oxycarbonylphenyl}pyrimidine, 2-[4-{1-Methyl-2-alkyl(of 1 to 20 carbon atoms)oxyethyl}-phenyl]-5-alkyl(of 3 to 20 carbon atoms)pyrimidine, 2-[4-{1-Methyl-2-alkyl(of 1 to 20 carbonatoms)oxyethyl}-phenyl]-5-alkyl(of 3 to 20 carbon atoms)oxypyrimidine, 2-[4-{1-Methyl-2-alkyl(of 1 to 20 carbon atoms)oxyethyl}-phenyl]-5-alkyl(of 3 to 20 carbon atoms)carbonyloxypyrimidine, 2-[4-{1-Methyl-2-alkyl(of 1 to 20 carbon atoms)oxyethyl}-phenyl]-5-alkyl(of 3 to 20 carbon atoms)oxycarbonylpyrimidine, 5-[4-{1-Methyl-2-alkyl(of 1 to 20 carbonatoms)oxyethyl}-phenyl]-2-alkyl(of 3 to 20 carbon atoms)pyrimidine, 5-[4-{1-Methyl-2-alkyl(of 1 to 20 carbonatoms)oxyethyl}-phenyl]-2-alkyl(of 3 to 20 carbon atoms)oxypyrimidine, 5-[4-{1-Methyl-2-alkyl(of 1 to 20 carbonatoms)oxyethyl}-phenyl]-2-alkyl(of 3 to 20 carbon atoms)carbonyloxypyrimidine, 5-[4-{1-Methyl-2-alkyl(of 1 to 20 carbonatoms)oxyethyl}-phenyl]-2-alkyl(of 3 to 20 carbon atoms)oxycarbonylpyrimidine, Compounds in which "1-methyl-2-alkyl(of 1 to 20 carbon atoms)-oxy(or carbonyloxy)ethyl" in the above exemplified compounds is replaced with any one of:

"1-methyl-3-alkyl(of 1 to 20 carbon atoms)oxy(or carbonyloxy)propyl",

"1-methyl-4-alkyl(of 1 to 20 carbon atoms)oxy(or carbonyloxy)butyl",

"1-methyl-5-alkyl(of 1 to 20 carbon atoms)oxy(or carbonyloxy)penty" and

"1-methyl-6-alkyl(of 1 to 20 carbon atoms)oxy(or carbonyloxy)hexyl".

Compounds in which "1-methyl-2-alkyl(of 1 to 20 carbona toms)-oxy(or carbonyloxy)ethyl" group which is a substituent on the phenyl group in the above exemplified compounds is replaced with any one of:

"1-methyl-3-alkyl(of 1 to 20 carbon atoms)oxy(or carbonyloxy)propyl",

"1-methyl-4-alkyl(of 1 to 20 carbon atoms)oxy(or carbonyloxy)butyl",

"1-methyl-5-alkyl(of 1 to 20 carbon atoms)oxy(or carbonyloxy)penty" and

"1-methyl-6-alkyl(of 1 to 20 carbon atoms)oxy(or carbonyloxy)hexyl" group.

Here, "alkyl (of 3 to 20 carbonatoms)" means an alkyl group having 3 to 20 carbons and "alkyl (of 1 to 20 carbonatoms)" means an alkyl group or an alkoxyalkyl group having 1 to 20 carbons and may be substituted with a halogen atom, and they are substituents exemplified above.

Further, specific examples of optically active benzene derivatives (I-a) and (I-b) will be shown below. In the names of the compounds, "alkyl (of 3 to 20 carbon atoms)" means an alkyl group of 3 to 20 carbons and "alkyl (of 1 to 20 carbon atoms)" means an alkyl group or an alkoxyalkyl group which has 1 to 20 carbons and may be substituted with a halogen atom. "heterocyclic" means a disubstituted heterocyclic ring such as 4',5-disubstituted-2-phenylpyrimidine

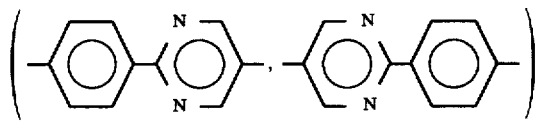

4',2-disubstituted-5-phenylpyrimidine

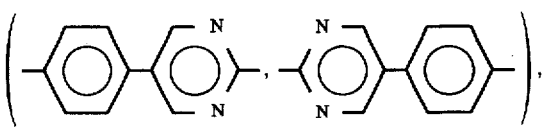

2,5-disubstituted pyrimidine

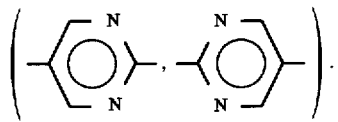

(i) 4-{Alkyl(of 3 to 20 carbon atoms)heterocyclic oxycarbonyl}-1-{1-alkyl(of 1 to 20 carbonatoms)oxyethyl)benzene, 4-{Alkyl(of 3 to 20 carbon atoms)oxyheterocyclicoxycarbonyl}-1-{1-alkyl(of 1 to 20 carbon atoms)oxyethyl}benzene, 4-{Alkyl(of 3 to 20 carbon atoms)carbonyloxyheterocyclic oxycarbonyl}-1-{1-alkyl(of 1 to 20 carbon atoms)oxyethyl}benzene, 4-{Alkyl(of 3 to 20 carbon atoms)oxycarbonylheterocyclic oxycarbonyl}-1-{1-alkyl(of 1 to 20 carbon atoms)oxyethyl}benzene, 4-{Alkyl(of 3 to 20 carbon atoms)heterocyclic oxycarbonyl}-1-{1-alkyl(of 1 to 20 carbon atoms)carbonyloxyethyl}benzene, 4-{Alkyl(of 3 to 20 carbon atoms)oxyheterocyclic oxycarbonyl}-1-{1-alkyl(of 1 to 20 carbon atoms)carbonyloxyethyl}benzene, 4-{Alkyl(of 3 to 20 carbon atoms)carbonylheterocyclic oxycarbonyl}-1-{1-alkyl(of 1 to 20 carbon atoms)carbonyloxyethyl}benzene, 4-{Alkyl(of 3 to 20 carbon atoms)oxycarbonylheterocyclic oxycarbonyl}-1-{1-alkyl(of 1 to 20 carbon atoms)carbonyloxyethyl}benzene, 4-{Alkyl(of 3 to 20 carbon atoms)heterocyclic carbonyloxy}-1-{1-alkyl(of 1 to 20 carbon atoms)oxyethyl}benzene, 4-{Alkyl(of 3 to 20 carbon atoms)oxyheterocyclic carbonyloxy}-1-{1-alkyl(of 1 to 20 carbon atoms)oxyethyl}benzene, 4-{Alkyl(of 3 to 20 carbon atoms)carbonyloxyheterocyclic carbonyloxy}-1-{1-alkyl(of 1 to 20 carbon atoms)oxyethyl}benzene, 4-{Alkyl(of 3 to 20 carbon atoms)oxycarbonylheterocyclic carbonyloxy}-1-{1-alkyl(of 1 to 20 carbon atoms)oxyethyl}benzene, 4-{Alkyl(of 3 to 20 carbon atoms)heterocyclic carbonyloxy}-1-{1-alkyl(of 1 to 20 carbon atoms)carbonyloxyethyl}benzene, 4-{Alkyl(of 3 to 20 carbon atoms)oxyheterocyclic carbonyloxy}-1-{1-alkyl(of 1 to 20 carbon atoms)carbonyloxyethyl}benzene, 4-{Alkyl(of 3 to 20 carbon atoms)carbonyloxyheterocyclic carbonyloxy}-1-{1-alkyl(of 1 to 20 carbon atoms)carbonyloxyethyl}benzene, 4-{Alkyl(of 3 to 20 carbon atoms)oxycarbonylheterocyclic oxycarbonyl}-1-{1-alkyl(of 1 to 20 carbon atoms)carbonyloxyethyl}benzene, 4-{Alkyl(of 3 to 20 carbon atoms)heterocyclic oxycarbonyl}-4'-(1-alkyl(of 1 to 20 carbon atoms)oxyethyl}biphenyl, 4-{Alkyl(of 3 to 20 carbon atoms)oxyheterocyclic oxycarbonyl}-4'-{1-alkyl(of 1 to 20 carbon atoms)oxyethyl}biphenyl, 4-{Alkyl(of 3 to 20 carbon atoms)carbonyloxyheterocyclic oxycarbonyl}-4'-{1-alkyl(of 1 to 20 carbon atoms)oxyethyl}biphenyl, 4-{Alkyl(of 3 to 20 carbon atoms)oxycarbonylheterocyclic oxycarbonyl}-4'-{1-alkyl(of 1 to 20 carbon atoms)oxyethyl}biphenyl, 4-{Alkyl(of 3 to 20 carbon atoms)heterocyclic oxycarbonyl}-4'-{1-alkyl(of 1 to 20 carbon atoms)carbonyloxyethyl}biphenyl, 4-{Alkyl(of 3 to 20 carbon atoms)oxyheterocyclic oxycarbonyl}-4'-{1-alkyl(of 1 to 20 carbon atoms)carbonyloxyethyl}biphenyl, 4-{Alkyl(of 3 to 20 carbon atoms)carbonyloxyheterocyclic oxycarbonyl}-4'-{1-alkyl(of 1 to 20 carbon atoms)carbonyloxyethyl}biphenyl, 4-{Alkyl(of 3 to 20 carbon atoms)oxycarbonylheterocyclic oxycarbonyl}-4'-{1-alkyl(of 1 to 20 carbon atoms)carbonyloxyethyl}biphenyl, 4-{Alkyl(of 3 to 20 carbon atoms)heterocyclic carbonyloxy}-4'-{1-alkyl(of 3 to 20 carbon atoms)oxyethyl}biphenyl, 4-{Alkyl(of 3 to 20 carbon atoms)oxyheterocyclic carbonyloxy}-4'-{1-alkyl(of 1 to 20 carbon atoms)oxyethyl}biphenyl, 4-{Alkyl(of 3 to 20 carbon atoms)carbonyloxyheterocyclic oxycarbonyl}-4'-{1-alkyl(of 1 to 20 carbon atoms)oxyethyl}-biphenyl, 4-{Alkyl(of 3 o 20 carbon atoms)oxycarbonylheterocyclic carbonyloxy}-4'-{1-alkyl(of 1 to 20 carbon atoms)oxyethyl}biphenyl, 4-{Alkyl(of 3 o 20 carbon atoms)heterocyclic carbonyloxy)-4'-{1-alkyl(of 1 to 20 carbon atoms)carbonyloxyethyl}biphenyl, 4-=Alkyl(of 3 o 20 carbon atoms)oxyheterocyclic carbonyloxy}-4'-{1-alkyl(of 1 to 20 carbon atoms)carbonyloxyethyl}biphenyl, 4-{Alkyl(of 3 o 20 carbon atoms)carbonyloxyheterocyclic carbonyloxy}-4'-{1-alkyl(of 1 to 20 carbon atoms)carbonyloxyethyl}biphenyl, 4-{Alkyl(of 3 o 20 carbon atoms)oxycarbonylheterocyclic carbonyloxy}-4'-{1-alkyl(of 1 to 20 carbon atoms)carbonyloxyethyl}biphenyl, Optically active compounds exemplified below are also included:

Compounds in which "2-alkyl(of 1 to 20 carbon atoms)oxy(or carbonyloxy)ethyl" group in the compounds exemplified below is replaced with any one of:

3-Alkyl(of 1 to 20 carbona toms)oxy(or carbonyloxy)propyl,

4-Alkyl(of 1 to 20 carbona toms)oxy(or carbonyloxy)butyl,

5-Alkyl(of 1 to 20 carbona toms)oxy(or carbonyloxy)pentyl and

6-Alkyl(of 1 to 20 carbona toms)oxy(or carbonyloxy)hexyl, (ii) 4-{Alkyl(of 3 to 20 carbona toms)heterocyclic oxycarbonyl}-1-{1-methyl-2-alkyl(of 1 to 20 carbon atoms)oxyethyl}benzene, 4-{Alkyl(of 3 to 20 carbonatoms)oxyheterocyclic oxycarbonyl}-1-{1-methyl-2-alkyl(of 1 to 20 carbon atoms)oxyethyl}benzene, 4-{Alkyl(of 3 to 20 carbonatoms)carbonyloxyheterocyclic oxycarbonyl}-1-{1-methyl-2-alkyl(of 1 to 20 carbon atoms)oxyethyl}benzene, 4-{Alkyl(of 3 to 20 carbonatoms)oxycarbonylheterocyclic oxycarbonyl}-1-{1-methyl-2-alkyl(of 1 to 20 carbon atoms)oxyethyl}benzene, 4-{Alkyl(of 3 to 20 carbonatoms)heterocyclic oxycarbonyl}-1-{1-methyl-2-alkyl(of 1 to 20 carbon atoms)carbonyloxyethyl}benzene, 4-{Alkyl(of 3 to 20 carbonatoms)oxyheterocyclic oxycarbonyl}-1-{1-methyl-2-alkyl(of 1 to 20 carbon atoms)carbonyloxyethyl}benzene, 4-{Alkyl(of 3 to 20 carbonatoms)carbonyloxyheterocyclic carbonyloxyethyl}benzene, 4-{Alkyl(of 3 to 20 carbonatoms)oxycarbonylheterocyclic oxycarbonyl}-1-{1-methyl-2-alkyl(of 1 to 20 carbon atoms)carbonyloxyethyl}benzene, 4-{Alkyl(of 3 to 20 carbonatoms)heterocyclic oxycarbonyl}-4'-{1-methyl-2-alkyl(of 1 to 20 carbon atoms)oxyethyl}biphenyl, 4-{Alkyl(of 3 to 20 carbonatoms)oxyheterocyclic oxycarbonyl}-4'-{1-methyl-2-alkyl(of 1 to 20 carbon atoms)oxyethyl}biphenyl, 4-{Alkyl(of 3 to 20 carbonatoms)carbonyloxyheterocyclic oxycarbonyl}-4'-{1-methyl-2-alkyl(of 1 to 20 carbon atoms)oxyethyl}biphenyl, 4-{Alkyl(of 3 to 20 carbonatoms)oxycarbonylheterocyclic oxycarbonyl}-4'-{1-methyl-2-alkyl(of 1 to 20 carbon atoms)oxyethyl}biphenyl, 4-{Alkyl(of 3 to 20 carbonatoms)heterocyclic oxycarbonyl}-4'-{1-methyl-2-alkyl(of 1 to 20 carbon atoms)carbonyloxyethyl}biphenyl, 4-{Alkyl(of 3 to 20 carbonatoms)oxyheterocyclic oxycarbonyl}-4'-{1-methyl-2-alkyl(of 1 to 20 carbon atoms)carbonyloxyethyl}biphenyl, 4-{Alkyl(of 3 to 20 carbonatoms)carbonyloxyheterocyclic oxycarbonyl}-4'-{1-methyl-2-alkyl(of 1 to 20 carbon atoms)carbonyloxyethyl}biphenyl, 4-{Alkyl(of 3 to 20 carbonatoms)oxycarbonylheterocyclic oxycarbonyl}-4'-{1-methyl-2-alkyl(of 1 to carbon atoms)carbonyloxyethyl}biphenyl, 4-{Alkyl(of 3 to 20 carbonatoms)heterocyclic carbonyloxyethyl}-1-{1-methyl-2-alkyl(of 1 to 20 carbon atoms)oxyethyl}benzene, 4-{Alkyl(of 3 to 20 carbonatoms)oxyheterocyclic carbonyloxy}-1-{1-methyl-2-alkyl(of 1 to 20 carbon atoms)oxyethyl}benzene, 4-{Alkyl(of 3 to 20 carbonatoms)carbonyloxyheterocyclic carbonyloxy}-1-{1-methyl-2-alkyl(of 1 to 20 carbon atoms)oxyethyl}benzene, 4-{Alkyl(of 3 to 20 carbonatoms)oxycarbonylheterocyclic oxycarbonyl}-1-{1-methyl-2-alkyl(of 1 to 20 carbon atoms)oxyethyl}benzene, 4-{Alkyl(of 3 to 20 carbonatoms)heterocyclic carbonyloxy}-1-{1-methyl-2-alkyl(of 1 to 20 carbon atoms)carbonyloxyethyl}benzene, 4-{Alkyl(of 3 to 20 carbonatoms)oxyheterocyclic carbonyloxy}-1-{1-methyl-2-alkyl(of 1 to 20 carbon atoms)carbonyloxyethyl}benzene, 4-{Alkyl(of 3 to 20 carbonatoms)carbonylheterocyclic carbonyloxy}-1-{1-methyl-2-alkyl(of 1 to 20 carbon atoms)carbonyloxyethyl}benzene, 4-{Alkyl(of 3 to 20 carbonatoms)heterocyclic carbonyloxy}-4'-{1-methyl-2-alkyl(of 1 to 20 carbon atoms)oxyethyl}biphenyl, 4-{Alkyl(of 3 to 20 carbonatoms)oxyheterocyclic carbonyloxy}-4'-{1-methyl-2-alkyl(of 1 to 20 carbon atoms)oxyethyl}biphenyl, 4-{Alkyl(of 3 to 20 carbonatoms)carbonyloxyheterocyclic carbonyloxy}-4'-{1-methyl-2-alkyl(of 1 to 20 carbon atoms)oxyethyl}biphenyl, 4-{Alkyl(of 3 to 20 carbonatoms)oxycarbonylheterocyclic carbonyloxy}-4'-{1-methyl-2-alkyl(of 1 to 20 carbon atoms)oxyethyl}biphenyl, 4-{Alkyl(of 3 to 20 carbonatoms)heterocyclic carbonyloxy}-4'-{1-methyl-2-alkyl(of 1 to 20 carbon atoms)carbonyloxyethyl}biphenyl, 4-{Alkyl(of 3 to 20 carbonatoms)oxyheterocyclic carbonyloxy}-4'-{1-methyl-2-alkyl(of 1 to 20 carbon atoms)carbonyloxyethyl}biphenyl, 4-{Alkyl(of 3 to 20 carbonatoms) carbonyloxyheterocyclic carbonyloxy}-4'-{1-methyl-2-alkyl(of 1 to 20 carbon atoms)carbonyloxyethyl}biphenyl, 4-{Alkyl(of 3 to 20 carbonatoms) oxycarbonyloxyheterocyclic carbonyloxy}-4'-{1-methyl-2-alkyl(of 1 to 20 carbon atoms)carbonyloxyethyl}biphenyl, 4-{Alkyl(of 3 to 20 carbonatoms)heterocyclic oxycarbonyl}-1-{2-alkyl(of 1 to 20 carbon atoms) oxypropyl}benzene, 4-{Alkyl(of 3 to 20 carbonatoms)oxyheterocyclic oxycarbonyl)-1-{2-alkyl(of 1 to 20 carbon atoms) oxypropyl}benzene, 4-{Alkyl(of 3 to 20 carbonatoms) carbonyloxyheterocyclic oxycarbonyl}-1-{2-alkyl(of 1 to 20 carbon atoms)oxypropyl}benzene, 4-{Alkyl(of 3 to 20 carbonatoms) oxycarbonyloxyheterocyclic oxycarbonyl}-1-{2-alkyl(of 1 to 20 carbon atoms)oxypropyl}benzene, 4-{Alkyl(of 3 to 20 carbonatoms)heterocyclic oxycarbonyl}-1-{2-alkyl(of 1 to 20 carbon atoms) carbonyloxypropyl}benzene, 4-{Alkyl(of 3 to 20 carbonatoms)oxyheterocyclic oxycarbonyl}-1-{2-alkyl(of 1 to 20 carbon atoms) carbonyloxypropyl}benzene, 4-{Alkyl(of 3 to 20 carbonatoms) carbonyloxyheterocyclic oxycarbonyl}-1-{2-alkyl(of 1 to 20 carbon atoms)carbonyloxypropyl}benzene, 4-{Alkyl(of 3 to 20 carbonatoms) oxycarbonyloxyheterocyclic oxycarbonyl}-1-{2-alkyl(of 1 to 20 carbon atoms)carbonyloxypropyl}benzene, 4-{Alkyl(of 3 to 20 carbonatoms)heterocyclic oxycarbonyl}-4'-{2-alkyl(of 1 to 20 carbon atoms) oxypropyl}biphenyl, 4-{Alkyl(of 3 to 20 carbonatoms)oxyheterocyclic oxycarbonyl}-4'-{2-alkyl(of 1 to 20 carbon atoms) oxypropyl}biphenyl, 4-{Alkyl(of 3 to 20 carbonatoms) carbonyloxyheterocyclic oxycarbonyl)-4'-{2-alkyl(of 1 to 20 carbon atoms)oxypropyl}biphenyl, 4-{Alkyl(of 3 to 20 carbonatoms) oxycarbonyloxyheterocyclic oxycarbonyl}-4'-{2-alkyl(of 1 to 20 carbon atoms)oxypropyl}biphenyl, 4-{Alkyl(of 3 to 20 carbonatoms)heterocyclic oxycarbonyl}-4'-{2-alkyl(of 1 to 20 carbon atoms) oxypropyl}biphenyl, 4-{Alkyl(of 3 to 20 carbonatoms)oxyheterocyclic oxycarbonyl}-4'-{2-alkyl(of 1 to 20 carbon atoms) carbonyloxypropyl}biphenyl, 4-{Alkyl(of 3 to 20 carbonatoms) carbonyloxyheterocyclic oxycarbonyl}-4'-{2-alkyl(of 1 to 20 carbon atoms)carbonyloxypropyl}biphenyl, 4-{Alkyl(of 3 to 20 carbonatoms) oxyarbonyloxyheterocyclic oxycarbonyl}-4'-{2-alkyl(of 1 to 20 carbon atoms)carbonyloxypropyl}biphenyl, 4-{Alkyl(having 3 to 20 carbon atoms)heterocyclic carbonyloxy}-1-{2-alkyl(having 1 to 20 carbon atoms) oxypropyl}benzene, 4-{Alkyl(having 3 to 20 carbon atoms)oxyheterocyclic carbonyloxy}-1-{2-alkyl(having 1 to 20 carbon atoms) oxypropyl}benzene, 4-{Alkyl(having 3 to 20 carbon atoms) carbonyloxyheterocyclic carbonyloxy}-1-{2-alkyl(having 1 to 20 carbon atoms)oxypropyl}benzene, 4-{Alkyl(having 3 to 20 carbon atoms) oxycarbonylheterocyclic carbonyloxy}-1-{2-alkyl(having 1 to 20 carbon atoms)oxypropyl}benzene, 4-{Alkyl(having 3 to 20 carbon atoms)heterocyclic carbonyloxy}-1-(2-alkyl(having 1 to 20 carbon atoms) carbonyloxypropyl}benzene, 4-{Alkyl(having 3 to 20 carbon atoms)oxyheterocyclic carbonyloxy}-1-(2-alkyl(having 1 to 20 carbon atoms) carbonyloxypropyl}benzene, 4-{Alkyl(having 3 to 20 carbon atoms) carbonyloxyheterocyclic carbonyloxy}-1-{2-alkyl(having 1 to 20 carbon atoms)carbonyloxypropyl}benzene, 4-{Alkyl(having 3 to 20 carbon atoms) oxycarbonylheterocyclic carbonyloxy}-1-{2-alkyl(having 1 to 20 carbon atoms)carbonyloxypropyl}benzene, 4-{Alkyl(having 3 to 20 carbon atoms)heterocyclic carbonyloxy}-4'-{2-alkyl(having 1 to 20 carbon atoms) oxypropyl}biphenyl, 4-{Alkyl(having 3 to 20 carbon atoms)oxyheterocyclic carbonyloxy}-4'-{2-alkyl(having 1 to 20 carbon atoms) oxypropyl}biphenyl, 4-{Alkyl(having 3 to 20 carbon atoms) carbonyloxyheterocyclic carbonyloxy}-4'-{2-alkyl(having 1 to 20 carbon atoms)oxypropyl}biphenyl, 4-{Alkyl(having 3 to 20 carbon atoms) oxycarbonylheterocyclic carbonyloxy}-4'-{2-alkyl(having 1 to 20 carbon atoms)oxypropyl}biphenyl 4-{Alkyl(having 3 to 20 carbon atoms)heterocyclic carbonyloxy}-4'-(2-alkyl(having 1 to 20 carbon atoms) carbonyloxypropyl}biphenyl, 4-{Alkyl(having 3 to 20 carbon atoms)oxyheterocyclic carbonyloxy}-4'-{2-alkyl(having 1 to 20 carbon atoms) carbonyloxypropyl}biphenyl, 4-{Alkyl(having 3 to 20 carbon atoms) carbonyloxyheterocyclic carbonyloxy}-4'-{2-alkyl(having 1 to 20 carbon atoms)carbonyloxypropyl}biphenyl, 4-{Alkyl(having 3 to 20 carbon atoms) oxycarbonylheterocyclic carbonyloxy}-4'-{2-alkyl(having 1 to 20 carbon atoms)carbonyloxypropyl}biphenyl, Compounds in which "2-alkyl(having 1 to 20 carbon atoms)oxy(or carbonyloxy)propyl" group which is a substituent is replaced with any one of:

3-alkyl(having 1 to 20 carbon atoms)oxy(or carbonyloxy) butyl, 4-alkyl(having 1 to 20 carbon atoms)oxy(or carbonyloxy) pentyl, 5-alkyl(having 1 to 20 carbon atoms)oxy(or carbonyloxy) hexyl, and 6-alkyl(having 1 to 20 carbon atoms)oxy(or carbonyloxy)heptyl group.

Further, the following compounds can be exemplified:

In the names of the compounds, "alkyl (having 1 to 20 carbon atoms)" means an alkyl group or an alkoxyalkyl group which has 1 to 20 carbons and may be substituted with a halogen atom, and they are optically active substituents among those exemplified above.

4-{Alkyl(having 3 to 20 carbon atoms)heterocyclic oxycarbonyl}-1-{alkyl(having 1 to 20 carbon atoms) oxymethyl}benzene, 4-{Alkyl(having 3 to 20 carbon atoms)oxyheterocyclic oxycarbonyl}-1-{alkyl(having 1 to 20 carbon atoms) oxymethyl}benzene, 4-{Alkyl(having 3 to 20 carbon atoms) carbonyloxyheterocyclic oxycarbonyl}-1-{alkyl(having 1 to 20 carbon atoms)oxymethyl}benzene, 4-{Alkyl(having 3 to 20 carbon atoms) oxycarbonylheterocyclic oxycarbonyl}-1-{alkyl(having 1 to 20 carbon atoms)oxymethyl}benzene, 4-{Alkyl(having 3 to 20 carbon atoms)heterocyclic oxycarbonyl}-1-{alkyl(having 1 to 20 carbon atoms) carbonyloxymethyl}benzene, 4-{Alkyl(having 3 to 20 carbon atoms)oxyheterocyclic oxycarbonyl}-1-{alkyl(having 1 to 20 carbon atoms) carbonyloxymethyl}benzene, 4-{Alkyl(having 3 to 20 carbon atoms) carbonyloxyheterocyclic oxycarbonyl}-1-{alkyl(having 1 to 20 carbon atoms)carbonyloxymethyl}benzene, 4-{Alkyl(having 3 to 20 carbon atoms) oxycarbonylheterocyclic oxycarbonyl]-1-{alkyl(having 1 to 20 carbon atoms)carbonyloxymethyl}benzene, 4-{Alkyl(having 3 to 20 carbon atoms)heterocyclic oxycarbonyl}-4'-alkyl(having 1 to 20 carbon atoms) oxymethyl}biphenyl, 4-{Alkyl(having 3 to 20 carbon atoms)oxyheterocyclic oxycarbonyl}-4'-{alkyl(having 1 to 20 carbon atoms) oxymethyl}biphenyl, 4-{Alkyl(having 3 to 20 carbon atoms) carbonyloxyheterocyclic oxycarbonyl}-4'-alkyl(having 1 to 20 carbon atoms)oxymethyl}biphenyl, 4-{Alkyl(having 3 to 20 carbon atoms) oxycarbonylheterocyclic oxycarbonyl}-4'-alkyl(having 1 to 20 carbon atoms)oxymethyl}biphenyl 4-{Alkyl(having 3 to 20 carbon atoms)heterocyclic oxycarbonyl}-4'-alkyl(having 1 to 20 carbon atoms) carbonyloxymethyl}biphenyl, 4-{Alkyl(having 3 to 20 carbon atoms)oxyheterocyclic oxycarbonyl}-4-{2-alkyl(having 1 to 20 carbon atoms) carbonyloxymethyl-}biphenyl, 4-}Alkyl(having 3 to 20 carbon atoms) carbonyloxyheterocyclic oxycarbonyl}-4'-alkyl(having 1 to 20 carbon atoms)carbonyloxymethyl}biphenyl, 4-{Alkyl(having 3 to 20 carbon atoms) oxycarbonylheterocyclic oxycarbonyl}-4'-alkyl(having 1 to 20 carbon atoms)carbonyloxymethyl}biphenyl, 4-{Alkyl(having 3 to 20 carbon atoms)heterocyclic carbonyloxy}-1-{alkyl(having 1 to 20 carbon atoms) oxymethyl}benzene, 4-{Alkyl(having 3 to 20 carbon atoms)oxyheterocyclic carbonyloxy}-1-{alkyl(having 1 to 20 carbon atoms) oxymethyl}benzene, 4-{Alkyl(having 3 to 20 carbon atoms) carbonyloxyheterocyclic carbonyloxyl-1-{alkyl(having 1 to 20 carbon atoms)oxymethyl}benzene, 4-{Alkyl(having 3 to 20 carbon atoms) oxycarbonylheterocyclic carbonyloxy}-1-{alkyl(having 1 to 20 carbon atoms)oxymethyl}benzene, 4-{Alkyl(having 3 to 20 carbon atoms)heterocyclic carbonyloxy}-1-{alkyl(having 1 to 20 carbon atoms) carbonyloxymethyl}benzene, 4-{Alkyl(having 3 to 20 carbon atoms)oxyheterocyclic carbonyloxy}-1-{alkyl(having 1 to 20 carbon atoms) carbonyloxymethyl}benzene, 4-{Alkyl(having 3 to 20 carbon atoms) carbonyloxyheterocyclic carbonyloxy}-1-{alkyl(having 1 to 20 carbon atoms)carbonyloxymethyl}benzene, 4-{Alkyl(having 3 to 20 carbon atoms) oxycarbonylheterocyclic carbonyloxy}-1-{alkyl(having 1 to 20 carbon atoms)carbonyloxymethyl}benzene, 4-{Alkyl(having 3 to 20 carbon atoms)heterocyclic carbonyloxy}-4'-{alkyl(having 1 to 20 carbon atoms) oxymethyl}biphenyl, 4-{Alkyl(having 3 to 20 carbon atoms)oxyheterocyclic carbonyloxy}-4'-{alkyl(having 1 to 20 carbon atoms) oxymethyl}biphenyl, 4-{Alkyl(having 3 to 20 carbon atoms) carbonyloxyheterocyclic carbonyloxy}-4'-{alkyl(having 1 to 20 carbon atoms)oxymethyl}biphenyl, 4-{Alkyl(having 3 to 20 carbon atoms) oxycarbonylheterocyclic carbonyloxy}-4'-{alkyl(having 1 to 20 carbon atoms)oxymethyl]biphenyl, 4-{Alkyl(having 3 to 20 carbon atoms)heterocyclic carbonyloxy}-4'-{alkyl(having 1 to 20 carbon atoms) carbonyloxymethyl}biphenyl, 4-{Alkyl(having 3 to 20 carbon atoms)oxyheterocyclic carbonyloxy}-4'-{alkyl(having 1 to 20 carbon atoms) carbonyloxymethyl}biphenyl, 4-{Alkyl(having 3 to 20 carbon atoms) carbonyloxyheterocyclic carbonyloxy}-4'-{alkyl(having 1 to 20 carbon atoms)carbonyloxymethyl}biphenyl, 4-{Alkyl(having 3 to 20 carbon atoms) oxycarbonylheterocyclic carbonyloxy}-4'-{alkyl(having 1 to 20 carbon atoms)carbonyloxymethyl}biphenyl, Compounds in which "alkyl(having 1 to 20 carbon atoms) oxy(or carbonyloxy)methyl" group which is a substituent is replaced with any one of:

2-alkyl(having 1 to 20 carbon atoms)oxy(or carbonyloxy) ethyl, 3-alkyl(having 1 to 20 carbon atoms)oxy(or carbonyloxy) propyl, 4-alkyl(having 1 to 20 carbon atoms)oxy(or carbonyloxy) butyl and 5-alkyl(having 1 to 20 carbon atoms)oxy(or carbonyloxy)pentyl group.

When the thus obtained optically active benzene derivatives represented by the general formula (I) is utilized as a constituent element of liquid crystals, particularly the constituent element of the ferroelectric liquid crystals, the substituent $R_2$ is preferably an alkyl group or an alkoxyalkyl group from a view of optical stability in practice, etc.

Further, in the ferroelectric liquid crystals, for permitting them to exert rapid response property which is a characteristic feature thereof, liquid crystals having a smaller viscosity coefficient are preferred and in case of optically active benzene derivatives represented by the general formula (I)-a and (I)-b, derivatives in which l=1 are particularly preferred.

For permitting liquid crystals to exert the rapid response property, a compound having a large spontaneous polarization is preferably used and in this case, s=1 is preferred.

Moreover, in case of the optically active benzene derivatives representing by the formula (I-b), in which z' is

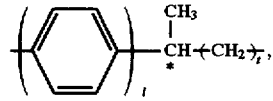

a birefringence type system is preferably employed because of larger quantities of said liquid crystalline compounds exhibit Sc*-$S_A$-I, when they are used as indicating element materials, and in case of the derivatives represented by the general formula (I-a), GH (Guest-Host) type system is more preferably employed as the phase transition because of larger quantities of Sc*-ch-I or Sc*-I.

Utilization of the optically active benzene derivatives represented by the general formulae (I-c) and (I-d) as a liquid crystal composition is effective for lowering the temperature range of the liquid crystal phase without enhancing the viscosity, even if said benzene derivatives themselves exhibit no liquid crystal phase. Further, in case of s=1 in which said derivatives represented by the formulae (I-c) and (I-d), the response speed can be enhanced because of excellent activity for enhancing spontaneous polarization in liquid crystal composition.

The liquid crystal composition of the present invention is one containing at least one kind of optically active benzene derivatives represented by the general formula (I) as the formulating component. In this case, the optically active benzene derivative represented by the general formula (I) is usually used so as to give a ratio of 0.1 to 99.9% by weight preferably 1 to 99% by weight based on the resulting liquid crystal composition. Further, such a liquid crystal composition is used to be effectively utilized also as a liquid crystal element, for example, a light switching element, and as the method of use of the liquid crystal composition in this case, a method which has heretofore been known can be applied as such without any particular limitation. Thus, according to the present invention, novel optically active derivatives represented by the general formula (I) can be easily obtained with a good yield, and besides can be effectively utilized as a liquid crystal composition and further as a liquid crystal element employing the same, due to excellent characteristics of said derivatives as a liquid crystal compound.

Optically active carboxylic acid compounds (III) can be also prepared by a process detailedly explained hereinafter.

Optically active carboxylic acid compounds represented by the general formula (III), wherein S is O, can be prepared by oxidizing optically active acetophenone derivatives represented by the general formula (XXII)

$CH_3CO-Z'-O-R_2$ (XXII)

wherein $R_2$ and $Z'$ have the same meanings as described above, with an oxidizing agent.

Examples of the oxidizing agent include potassium dichromate, sodium dichromate, potassium permanganate, sodium permanganate, potassium hypochlorite, sodium hypochlorite, potassium hypobromite, sodium hypobromite and the like.

The required equivalent amount of such an oxidizing agent used is once or more based on the optically active acetophenone derivatives (XXII), and the upper limit is not particularly restricted but preferably 10 times.

Solvents inert to oxidative reaction are normally employed as a solvent used in the reaction, and examples of such a solvent include water, dioxane, tetrahydrofuran, N-methylpyrrolidone and the like.

The reaction temperature is normally within the range of −20° to 130° C., preferably −10° to 100° C.

After completing the reaction, the optically active carboxylic acid compound [wherein s is 0 in the general formula (III)] can be obtained in good yield by ordinary operations, such as ordinary means, for example operation, such as filtration coagulation with acids, extraction, liquid separation, concentration and the like, and, if necessary, purified by column chromatography, recrystallization and the like.

The optically active acetophenone derivatives represented by the general formula (XXII) can be prepared by reacting an optically active aromatic alcohol represented by the general formula (XXIII)

$CH_3CO-Z'-OH$ (XXIII)

wherein $Z'$ denotes the same meaning as described above, with an alkylating agent represented by the general formula (IX)

$R_2-Q$ (IX)

wherein $R_2$ respectively denotes the same meaning as described above; Q respectively denotes a halogen atom or $-OSO_2R'''$, where $R'''$ denotes a lower alkyl group or phenyl group which may be substituted by the lower alkyl group, in the presence of a basic substance in a solvent.

Examples of the basic substance include alkaline metal hydrides, such as sodium hydride and potassium hydride, alkaline metal or alkaline earth metal hydroxides, such as sodium hydroxide, potassium hydroxide and calcium hydroxide, alkaline metal carbonates, such as sodium carbonate and potassium carbonate, butyl lithium, and the like and alkali metals, such as lithium, sodium, potassium and the like.

The required equivalent amount of such a basic substance used is once or more based on the optically active aromatic alcohol (XXIII), and the upper limit is not particularly restricted but preferably 1 to 5 times.

Examples of the alkylating agent used in this reaction include halides, such as chloride, bromide, iodide and the like or sulfonic acid esters (methanesulfonic acid ester, ethanesulfonic acid ester, benzenesulfonic acid ester, toluenesulfonic acid ester and the like) having an alkyl group or alkoxyalkyl group of 1 to 20 carbon atoms which may be substituted by a halogen atom. The aforementioned alkylating agent, if necessary, can be readily synthesized from the corresponding alcohol.

In addition, the above-mentioned alkyl group or alkoxyalkyl group may be an optically active group.

The alkylating agent (halides or sulfonic acid esters) having such an optically active group, if necessary, is synthesized from the corresponding optically active alcohol. Some of the above-mentioned optically active alcohol is readily obtained by asymmetric reduction of the corresponding ketone with an asymmetric metal catalyst, microorganism or enzyme. Some are present in nature or can be induced from optically active amino acids and optically active oxy acids obtained by optical resolution as follows: valine, leucine, isoleucine, phenylalanine, threonine, allothreonine, homoserine, alloisoleucine, test-leucine, 2-aminobutyric acid, norvaline, norleucine, ornithine, lysine, hydroxylysine, phenylglycine, aspartic acid, glutamic acid, mandelic acid, tropic acid 3-hydroxybutyric acid, malic acid, tartaric acid, isopropylmalic acid and the like.

Such an alkylating agent (IX) is used in an optional equivalent amount of once or more, but normally 1 to 5 times based on the optically active aromatic alcohol (XXIII).

Examples of the reaction solvent which can be used include ethers, such as tetrahydrofuran or methyl ether, ketones, such as acetone or methyl ethyl ketone, aromatic hydrocarbons, such as toluene or benzene, halogenated hydrocarbons, such as chloroform, dichloromethane, dichloroethane, or chlorobenzene, aliphatic hydrocarbons, such as pentane or hexane, or polar solvents, such as dimethylformamide, dimethyl sulfoxide, hexamethylphosphoramide or N-methylpyrrolidone or the like.

The reaction is carried out normally at −50° to 120° C., preferably −30° to 100° C.

The reaction time is not particularly limited, and the time when the optically active aromatic alcohol represented by the general formula (XXIII) disappears can be assumed as the end point of the reaction.

The optically active acetophenone derivatives represented by the general formula (XXII) can be taken out of the reaction mixture by applying ordinary post-treating operation, for example extraction, liquid separation, concentration and the like.

Further, in case of which the alkylating agent is an iodide, said reaction of an optically active aromatic alcohol (XXIII) and alkylating agent can be conducted by using silver oxide in place of said basic substance.

The optically active aromatic alcohol represented by the general formula (XXIII) can be prepared by two processes described below. That is, in case $Z'$ is

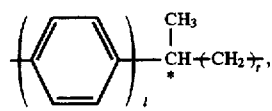

the optically active aromatic alcohol can be prepared by hydrolyzing an optically active lower alkyl ester compound represented by the general formula (XXIV)

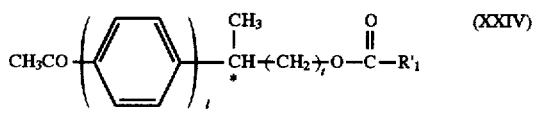

wherein $R_1'$ denotes a lower alkyl group; l, t and mark * respectively denote the same meanings as mentioned above.

On the other hand, in case Z' is

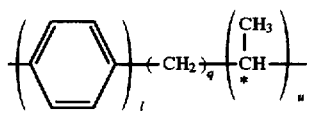

where u is 1, the optically active aromatic alcohol (XXIII) can be prepared by asymmetrically hydrolyzing a lower alkyl ester derivative represented by the general formula (XXVIII)

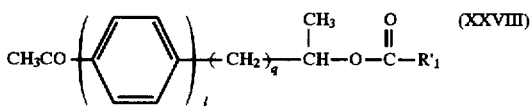

wherein R'₁ and q have the same meanings as described above.

i) The aforementioned hydrolytic reaction is normally carried out in the coexistence of an acid or alkali.

Examples of the acid herein used include inorganic acids, such as sulfuric acid, phosphoric acid, hydrochloric acid and the like, and organic acids, such as toluenesulfonic acid, methanesulfonic acid and the like. Examples of the alkali include organic and inorganic bases, such as sodium hydroxide, potassium hydroxide, barium hydroxide potassium carbonate, 1,8-diazabicyclo[5,4,0]7-undecene and the like.

The amount of such an acid or alkali used is as described below. In the case of the acid, the molar amount used is preferably 0.02 to 10 times based on 1 mol of the optically active lower alkyl ester compound (XXIV). In the case of the alkali, the molar amount is at least once or more, preferably 5 times or less based on said lower alkyl ester compound (XXIV). Of course, a larger amount than those described above may be used. The acid or alkali is normally used with a solvent, and examples of such a solvent used include the following: Water, aliphatic or aromatic hydrocarbons, ethers, alcohols, ketones, amides and halogenated hydrocarbons, such as methanol, ethanol, propanol, acetone, methyl ethyl ketone, chloroform, dichloromethane, toluene, xylene, hexane, heptane, ethyl ethedioxane, dimofuran, dioxane, dimethylformamide, N-methylpyrrolidone and the like alone inert to reaction or a mixture thereof. The amount thereof used is not particularly limited.

The reaction temperature is –30° to 120° C., and preferably –20° to 100° C.

The reaction time is not particularly limited. After completing the reaction, the optically active aromatic alcohol in which Z' is

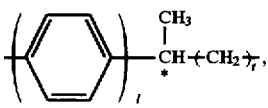

in the general formula (XXIII) is obtained in good yield by ordinary separating means, for example extraction, liquid separation, concentration, recrystalization and the like. Such an optically active aromatic alcohol, if necessary, can be then purified by column chromatography and the like, but the reaction mixture can be normally used directly for the next step.

The optically active lower alkyl ester compound represented by the general formula (XXIV) can be prepared by acetylating an optically active alkylphenyl ester represented by the general formula (XXV)

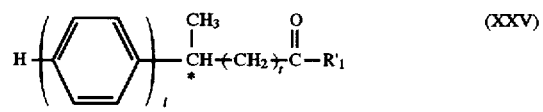

wherein l, t and mark * have the same meanings as mentioned above; $R_1'$ denotes a lower alkyl group. Ordinary Friedel-Crafts reactions are applied to the above-mentioned acetylation. Examples of the acetylating agent include acetic acid and derivatives thereof, such as acetyl chloride, acetyl bromide and the like. The amount thereof used is 1 moles or more, preferably 3 moles or below based on the optically active alkylphenyl ester (XXV). A catalyst employed for the ordinary Friedel-Crafts reactions is used for the acetylation. Examples of such a catalyst include aluminum chloride, aluminum bromide, zinc chloride, zinc bromide, titanium tetrachloride, polyphosphoric acid, boron trifluoride and the like. The molar amount thereof used is 0.3 to 3 times based on said alkylphenyl ester (XXV).

The reaction temperature is normally –30° to 150° C., preferably –10° to 100° C.

The reaction time is not particularly limited.

Optically active lower alkyl ester compounds (XXIV) are obtained in good yield from the reaction mixture thus obtained by operation, such as liquid separation, concentration, distillation, crystallization and the like and, if necessary, can be further purified by column chromatography and the like. The resulting compounds can be normally used directly for the next step.

The optically active alkylphenyl ester represented by the general formula (XXV) can be prepared by acylating an optically active benzene compound represented by the general formula (XXVI)

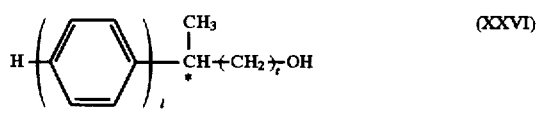

wherein l, t and mark * have the same meanings as described above. Ordinary esterification methods are applied to the aforementioned acylation, which can be carried out in the presence or absence of a solvent using a catalyst.

In such acylation, acid anhydrides, or acid halides of lower alkylcarboxylic acids are normally used as the acylating agent. Examples thereof include acetic anhydride, propionic anhydride, acetyl chloride or bromide, propionyl chloride or bromide, butyryl chloride or bromide, valeroyl chloride or bromide or the like.

In case a solvent is used in this reaction, examples of the solvent include aliphatic or aromatic hydrocarbons, ethers, ketones, halogenated hydrocarbons or aprotic polar solvents, such as tetrahydrofuran, ethyl ether, acetone, methyl ethyl ketone, toluene, benzene, chlorobenzene, dichloromethane, dichloroethane, chloroform, carbon tetrachloride, dimethylformamide and hexane inert to reaction alone or a mixture thereof. The solvent can be used in a particularly unlimited amount.

The equivalent amount of the acylating agent required is once or more based on the optically active benzene compound (XXVI), and the upper limit is not particularly restricted, but preferably 4 times or less.

Examples of the catalyst include organic or inorganic basic substances, such as dimethylaminopyridine, triethylamine, tri-n-butylamine, pyridine, picoline, imidazole, sodium carbonate, sodium methylate, potassium hydrogencarbonate and the like. The equivalent amount thereof is not particularly limited, but normally 1 to 5 times based on the optically active benzene compound (XXVI).

An organic amine, if used as the solvent, may act as the catalyst.

Acids, such as toluenesulfonic acid, methanesulfonic acid, sulfuric acid and the like can be also used as the catalyst.

The amount of the catalyst used varies with combination of the kind of the acylating agent and the catalyst used or the like and cannot be always specified. For example, in case an acid halide is used as the acylating agent, the equivalent amount thereof used is once or more based on the aforementioned acid halide.

The reaction temperature is normally –30° to 100° C., and preferably –20° to 90° C.

The reaction time is not particularly limited, and the time when the optically active benzene compound (XXVI) disappears can be assumed as the end point of the reaction.

After completing the reaction, the optically active alkylphenyl ester (XXV) can be obtained in good yield by ordinary separating means, for example operation, such as extraction, liquid separation, concentration, recrystalization and the like. Such an ester (XXV) may be also purified by column chromatography and the like, but can be normally used directly for the next step.

The optically active benzene compound (XXVI) can be readily prepared by reducing an optically active phenylalkylcarboxylic acid represented by the general formula (XXVII)

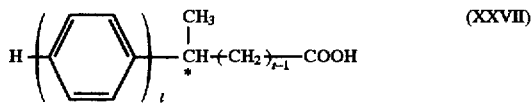

wherein l, t and mark * are the same as described above.

The above-mentioned optically active phenylalkylcarboxylic acid (XXVII) can be prepared by optically resolving the corresponding dl-isomer in case t is an integer of 1 to 2 in the general formula (XXVII) with an optically active amine, such as phenethylamine.

On the other hand, in case t is an integer of 3 to 5 in the general formula (XXVII), the optically active phenylalkylcarboxylic acid can be prepared by halogenating the hydroxyl group of an optically active benzene compound represented by the general formula (XXVI) wherein t is an integer of 1 to 2, to provide a haloalkylbenzene or haloalkylbiphenyl, then reacting the resulting compound with a malonic acid ester to afford a malonic acid ester derivative, hydrolyzing the afore-mentioned malonic acid ester derivative and subsequently decarboxylating the obtained hydrolyzate.

ii) The asymmetric hydrolytic reaction of the lower alkyl ester derivative represented by the general formula (XXVIII) is carried out by using an esterase having the ability to hydrolyze only either of the enantiomers of the above-mentioned ester derivative.

Esterase refers to esterases in a wide sense including lipase.

Microorganisms producing the esterase used in the reaction may be those having the ability to asymmetrically hydrolyze the lower alkyl ester derivative (XXVIII) and are not particularly limited.

Specific examples of such microorganisms include those belonging to the genus Enterobacter, Arthrobacter, Brevibacterium, Pseudomonas, Alcaligenes, Micrococcus, Chromobacterium, Microbacterium, Corynebacterium, Bacillus, Lactobacillus, Trichoderma, Candida, Sacharomyces, Rhodotorula, Cryptococcus, Torulopsis, Pichia, Penicillium, Aspergillus, Rhizopus, Mucor, Aureobasidium Actinomucor, Nocardia, Streptomyces, Hansenula or Achromobacter.

The above-mentioned microorganisms are normally cultivated in a liquid culture medium according to a conventional method to provide a culture solution.

For example, a microorganism is inoculated into a sterilized liquid culture medium [malt extract.yeast extract culture medium (prepared by dissolving 5 g of peptone, 10 g of glucose, 3 g of malt extract, and 8 g of yeast extract in 1 l of water and adjusting the pH to 6.5) for molds or yeasts and sugared bouillon culture medium (prepared by dissolving 10 g of glucose, 5 g of peptone, 5 g of meat extract and 3 g of NaCl in 1 l of water and adjusting the pH to 7.2) for bacteria] and cultivated normally at 20° to 40° C. for 1 to 3 days by reciprocating shaking culture.

Solid culture, if necessary, may be carried out.

Some of esterase derived from such microorganisms are commecially available and readily obtainable. Specific examples of commercially available esterase include lipase of the genus Pseudomonas [Lipase P (manufactured by Amano Pharmaceutical Co., Ltd.], lipase of the genus Aspergillus [Lipase AP (manufactured by Amano Pharmaceutical Co., Ltd.], lipase of the genus Mucor [Lipase M-AP (manufactured by Amano Pharmaceutical Co., Ltd.)] lipase of *Candidaa cylindracea* [Lipase MY (manufactured by the Meito Sangyo Co., Ltd.)], lipase of the genus Alcaligenes [Lipase PL (manufactured by the Meito Sangyo Co., Ltd.)], lipase of the genus Achromobater [Lipase AL (manufactured by the Meito Sangyo Co., Ltd.)], lipase of the genus Achromobacter [Lipase Godo BSL (Godo Shusei Co., Ltd.)], lipase of the genus Chromobacterium (manufactured by Toyo Jozo Co., Ltd.), lipase of *Rhizopus delemer* [Taripase (manufactured by Tanabe Seiyaku Co., Ltd.)] and lipase of the genus Rhizopus (Lipase Saiken (manufactured by Osaka Saikin Kenkyusho)].

In addition, animal and plant esterase can be used, and specific esterase includes the following: steapsin, pancreatin, porcine liver esterase and wheat germ esterase.

Enzymes obtained from animals, plants and microorganisms are used as the esterase employed in this reaction. Forms thereof used include various purified enzymes, crude enzymes, enzyme-containing substances, microbial culture solutions, cultures, microbial cells, culture filtrates and treated substances thereof as required and enzymes and microorganisms can be used in combination. Alternatively, the enzymes can be used as immobilized enzymes or immobilized microbial cells prepared by immobilizing on resins or the like.

The asymmetric hydrolytic reaction is carried out by vigorously stirring a mixture of the lower alkyl ester derivative (XXVIII) with the above-mentioned enzyme or microorganism normally in a buffer solution.

Buffer solutions of inorganic acid salts, such as normally used sodium phosphate, potassium phosphate and the like, or organic acid salts, such as sodium acetate, sodium citrate and the like, are used as the buffer solution. pH thereof is preferably 8 to 11 for culture solutions of alkalophilic microorganisms or alkaline esterase and 5 to 8 for culture solutions of nonalkalophilic microorganisms or esterase having no alkali tolerance. The concentration is within the range of normally 0.05 to 2M, preferably 0.05 to 0.5M.

The reaction temperature is normally 10° to 60° C., and the reaction time is generally 10 to 70 hours without any limitation thereof.

If a lipase belonging to the genus Pseudomonas or Arthrobacter is used as the lipase in the asymmetric hydrolytic reaction, the optically active aromatic alcohol (XXIII) can be obtained in a relatively, high optical yield.

In the asymmetric hydrolysis, an organic solvent, such as toluene, chloroform, methyl isobutyl ketone, dichloromethane or the like, inert to the reaction can be also used in addition to the buffer solution, and the asymmetric hydrolytic reaction can be advantageously carried out by using the organic solvent.

Only either of optically active substances of the lower alkyl ester derivative (XXVIII) is hydrolyzed by such asymmetric hydrolytic reaction to produce the optically active aromatic alcohol represented by the general formula (XXIII). On the other hand, optically active esters which are the other optically active substance of said lower alkyl ester derivative (XXVIII) remain intact as a hydrolytic residue.

After completing such asymmetric hydrolyric reaction, the optically active aromatic alcohol (XXIII) which is a hydrolyzate and optically active esters which are a hydrolytic residue [asymmetrically unhydrolyzed optically active substances of the lower alkyl ester derivative (XXVIII)] can be separated by a method for extracting the asymmetric hydrolytic reaction solution with a solvent, for example methyl isobutyl ketone, ethyl acetate, ethyl ether or the like, distilling away the solvent from the organic layer, then treating the concentration residue by column chromatography and the like.

The resulting optically active aromatic esters, if necessary, can be further hydrolyzed to provide an optically active aromatic alcohol which is an antipode of the previously obtained optically active aromatic alcohol (XXIII).

The lower alkyl ester derivative represented by the general formula (XXVIII) can be prepared by acetylating a phenylalkyl ester represented by the general formula (XXIX)

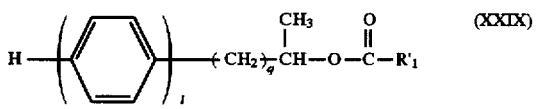

wherein R₁' denotes a lower alkyl group; l and q denote the same meanings as described above), in the solvent(s).

Ordinary Friedel-Crafts reactions are applied to the acetylation. Examples of acetic acid and derivatives thereof used for the acetylation include acetic acid, acetyl chloride, acetyl bromide or the like. The molar amount of such an acetylating agent used is once or more, preferably 3 times or less based on the phenylalkyl ester (XXIX).

Examples of said solvent(s) used in this reaction include halogenated hydrocarbons or nitroalkanes such as dichloromethane, carbon tetrachloride and nitromethane inert to reaction.

Catalysts used for the ordinary Friedel-Crafts reactions are employed for the acetylation. Examples of such catalysts include aluminum chloride, aluminum bromide, zinc chloride, zinc bromide, titanium tetrachloride, polyphosphoric acid, boron trifluoride or the like. The molar amount thereof used is 0.3 to 3 times based on the phenylalkyl esters (XXIX).

The reaction temperature is normally −30° to 150° C., preferably −10° to 100° C.

The reaction time is not particularly limited.

The lower alkyl ester derivative (XXVIII) is obtained from the resulting reaction mixture in good yield by operation, such as liquid separation, concentration, distillation, crystallization and the like, and, if necessary, can be further purified by column chromatogarphy and the like but normally used directly for the next step.

The phenylalkyl ester represented by the general formula (XXIX) can be prepared by acylating a phenylalkanol represented by the general formula (XXX)

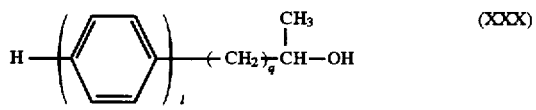

wherein l and q are the same as described above, with a lower alkylcarboxylic acid or derivative thereof.

Ordinary esterification methods are applied to the acylation reaction, and can be carried out in the presence or absence of a solvent using a catalyst.

In such acylation reaction, acid anhydrides or halides of lower alkylcarboxylic acids are normally used as the acylating agent, and examples thereof include acetic anhydride, propionic anhydride, acetyl chloride or bromide, propionyl chloridge or bromide, butyryl chloride or bromide, valeroyl chloride or bromide or the like.

In case a solvent is used in the reaction, examples thereof include aliphatic or aromatic hydrocarbons, ethers, ketones, halogenated hydrocarbons or aprotic polar solvents, for example tetrahydrofuran, ethyl ether, acetone, methyl ethyl ketone, toluene, benzene, chlorobenzene, dichloromethane, dichloroethane, chloroform, carbon tetrachloride, dimethylformamide, hexane or the like, inert to the reaction alone or a mixture thereof. Such a solvent can be used in an amount without any particular limitation.

The required equivalent amount of the acylating agent used in the reaction is once or more based on the phenylalkanol (XXX) which is a raw material. The upper limit is not particularly restricted, but preferably 4 times or less.

Examples of the catalyst include organic or inorganic basic substances, such as dimethylaminopyridine, triethylamine, tri-n-butylamine, pyridine, picoline, imidazole, sodium carbonate, sodium methylate, potassium hydrogencarbonate and the like. The molar amount thereof used is not particularly limited, and normally 1 to 5 times based on the phenylalkanol (XXX).

An organic amine, if used as a solvent, may act as the catlyst.

In addition, acids, such as toluenesulfonic acid, methanesulfonic acid, sulfuric acid or the like can be also used as the catalyst.

The amount of the catalyst used varies with combination of the kind of the acylating agent and the catalyst used, and cannot be always specified. However, if an acid halide is used as the acylating agent, the catlyst is used in an equivalent amount of once or more based on the above-mentioned acid halide.

The reaction temperature is normally −30° to 100° C., and preferably −20 to 90° C.

The reaction time is not particularly limited, and the time when the phenylalkanol (XXX) disappears can be assumed as the end point of the reaction.

After completing the reaction, the phenylalkyl esters (XXIX) can be obtained in good yield by ordinary separating means, for example, such as extraction, liquid separation, concentration, recrystalization and the like, and, if necessary, purified by column chromatography and the like. The reaction mixture, however, can be directly used for the next step.

An optically active phenol represented by general formula (V) may be prepared by debenzylating an optically active benzyloxybenzene derivative represented by general formula (VIII)

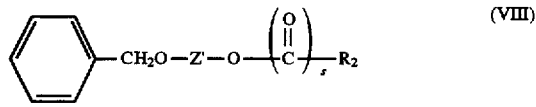

wherein $R_2$, $Z'$ and s represent as defined above, in a solvent in the presence of a hydrogenating catalyst and hydrogen.

As hydrogenating catalysts, platinum type catalysts such as $PtO_2$, Pt—C, etc. or palladium type catalysts such as Pd—C, Pd—$BaSO_4$, palladium black, etc. or rhodium type catalysts such as Rh—C, Rh—$Al_2O_3$, etc. or ruthenium type catalysts such as $RuO_2$, Ru—C, etc. or nickel type catalysts such as Raney nickel, etc. may be recited and preferably the palladium type catalysts are used.

The hydrogenating catalyst is used in an amount of ordinally 0.01 to 100% by weight preferably, 0.1–50% by weight based on an optically active benzyloxybenzene derivative represented by formula (VIII).

As the solvent, a solvent alone or a mixture of solvents such as alcohols such as methanol, ethanol, etc. or ethers such as dioxane, tetrahydrofuran, etc. or aromatic hydrocarbons such as benzene, toluene, etc. or aliphatic hydrocarbons such as n-hxane, cyclohexane, etc. or esters such as ethyl acetate, etc. or amides such as dimethylformamide or aliphatic acids such as acetic acid, etc. or water, etc. are exemplified. Hydrogen pressure is usually 1–200 atms.

The reaction is carried out at a temperature of ordinally 0°–200° C., more preferably 20°–180° C. The reaction time varies by depending on kind of hydrogenating catalyst, reaction temperature and hydrogen pressure, and is not particularly limited but the terminating point of the reaction is determined ordinally by disappearance of optically active benzyloxybenzene derivative (VIII) from the reaction system or termination of hydrogen absorption.

Recovery of an optically active phenol represented by general formula (V) from the reaction mixture is carried out by adding usual after-treatment procedures such as filtration, concentration, recrystalization, distillation or column chromatography, etc.

An optically active benzyloxybenzene derivative represented by general formula (VIII) may be prepared by reacting an optically active alcohol represented by general formula (XI)

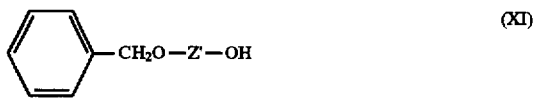

wherein $Z'$ represents as defined above, with a carboxylic acid represented by following general formula (X)

$$R_2COOH \qquad (X)$$

wherein $R_2$ represents as defined above, or derivative thereof in the presence of a catalyst or condensing agent, or reacting said alcohol with an alkylating agent represented by general formula (IX)

$$R_2\text{—}Q \qquad (IX)$$

wherein $R_2$ represents as defined above, Q represents a halogen atom or —$OSO_2R'''$, $R'''$ represents a lower alkyl group or phenyl group which may be substituted with a lower alkyl group, in a solvent in the presence of a basic substance.

In this reaction, in which carboxylic acid represented by formula (X) or derivative thereof is used, the carboxylic acid having the above-mentioned substituent $R_2$ or it's acid anhydride or acid halide such as acid chloride or acid bromide, etc. are used.

Further, these carboxylic acids or their derivative may be any of the racemic substances or optically active substances and when the carboxylic acids are optically active substances, some one among them may be obtained by oxidation of the corresponding alcohol or reductive deamination of the amino acid, or some one among them can be induced from optically active amino acids or optically active oxy acids which are exemplified hereinbelow and which naturally exist or may be obtained by optical resolution: alanine, valine, leucine isoleucine, phenyl alanine, serine, threonine, allothreonine, homoserine, alloisoleucine, tert-leucine, 2-aminobutyric acid, norvaline, norleucine, ornithine, lysine, hydroxylysine, phenylglycine, trifluoroalanine, asparginic acid, glutamic acid, lactic acid, mandelic acid, tropic acid, 3-hydroxybutyric acid, malic acid, tartaric acid, isopropyl malic acid, etc.

The reaction of such a carboxylic acid or it's derivative with an optically active alcohol (XI) is carried out in the presence or absence of solvent.

As the solvent, a solvent alone or a mixture of solvents which are inert to the reaction, for example aliphatic or aromatic hydrocarbons, ethers, ketones, amides or halogenated hydrocarbons, etc. such as tetrahydrofuran, ethyl ether, acetone, methylethyl ketone, toluene, benzene, chloroform, chlorobenzene, dichloromethane, dichloroethane, carbon tetrachloride, dimethylformamide, hexane, etc. are exemplified and the using amount of the solvent is not particularly limited.

When an acid anhydride or acid halide is used in this reaction, this reaction is carried out with using a catalyst. The using amount of an acid anhydride or acid halide requires one equivalent-fold or more based on an optically active alcohol (XI) and although the upper limit is particularly restricted, it is preferably, 4 equivalent-folds or less. As the catalyst, for example organic or inorganic basic substances such as dimethylaminopyridine, triethylamine, tri-n-butylamine, picoline, imidazole, sodium carbonate, or potassium hydrogen carbonate may be exemplified, and further organic acids or inorganic acids such as toluenesulfonic acid, methanesulfonic acid, sulfuric acid, etc. may be exemplified. Although using amount of catalyst is not particularly limited, for example when an acid halide is used the amount of the catalyst is 1 equivalent-fold or more based on said acid halide.

Further, when a carboxylic acid (X) is used in the reaction, said reaction is carried out by using a condensing agent. The using amount of the carboxylic acid is usually 1–2 equivalent-folds based on an optically active alcohol (XI).

As the condensing agent, carbodiimides such as N, N'-dicyclohexylcarbodiimide, and N-cyclohexyl-N'-(4-diethylamino)cyclohexylcarbodiimide are preferably used and also, if necessary organic bases such as 4-pyrrolidinopyridine, pyridine, triethylamine are co-used.

The use amount of the condensing agent is 1–1.2 equivalent-folds based on a carboxylic acid (X) and when an organic base is co-used, the use amount of the organic base is 0.01–0.2 equivalent-fold based on the condensing agent.

The reaction is carried out at a temperature of usually −80° C. to 120° C., preferably −20° C. to 90° C.

The reaction time is not particularly limited and the time when an optically active alcohol (XI) disappeared from the reaction system, may be regarded as terminating point of the reaction.

When alkylating reagent (IX) is used as basic substances, alkali metal hydrides such as sodium hydride, potassium hydride; alkali metal hydroxides or alkaline earth metal hydroxides such as sodium hydroxide, potassium hydroxide, calcium hydroxide; alkali metal carbonates such as sodium carbonate, potassium carbonate; butyl lithium, etc. are exemplified and also alkali metals such as lithium, sodium, potassium, etc. are exemplified.

Such a basic substance is required in an amount of 1 equivalent-fold or more based on an optically active alcohol (XI) and although the upper limit of the amount is not particularly restricted, 1–5 equivalent-folds are preferably used.

Alkylating reagent (IX) which is used in this reaction, includes a halide having $C_{1-20}$ alkyl group or alkoxyalkyl group which may be substituted with halogen atom(s), such as the chloride the bromide, the iodide, etc., or esters of sulfonic acid (methane sulfonic acid ester, ethane sulfonic acid ester, benzene sulfonic acid ester, toluene sulfonic acid ester, etc.).

If necessary, these alkylating reagents may be readily synthesized from the corresponding alcohol.

Further, above alkyl group or alkoxyalkyl group may be an optically active group.

The alkylating agents having these optically active group (halides or esters of sulfonic acid) are, if necessary synthesized from the corresponding optically active alcohols. Some of said optically active alcohols may be readily obtained by asymmetric reduction of the corresponding ketone with an asymmetric metal catalyst or a microorganism or an enzyme. Also, some of said alcohols can be induced from optically active amino acid and optically oxy acid which are exemplified hereinbelow and which naturally exist or may be obtained by optical resolution. Valine, leucine, isoleucine, phenylalanine, threonine, allothreonine, homoserine, alloisoleucine, tert-leucine, 2-amino butyric acid, norvaline, norleucine, ornithine, lysine, hydroxylysine, phenylglycine, asparaginic acid, glutamic acid, mandelic acid, tropic acid, 3-hydroxybutyric acid, malic acid, tartaric acid, isopropyl malic acid, etc.

Such an alkylating reagent (IX) is used in any amount of 1 equivalent-fold or more based on an optically active alcohol (XI) but usually 1–5 equivalent-folds are used.

As solvents, for example, ethers such as tetrahydrofuran or ethyl ether, etc.; ketones such as acetone or methylethyl ketone, etc.; aromatic hydrocarbons such as toluene or benzene, etc.; halogenated hydrocarbons such as chloroform or dichloromethane or dichloroethane or chlorobenzene; etc.; aliphatic hydrocarbons such as pentane or hexane, etc.; polar solvents such as dimethylformamide or dimethyl sulfoxide or hexamethylphosphorylamide or N-methylpyrrolidone, etc. may be used.

The reaction is carried out at a temperature of usually −50° C. to 120° C., preferably −30° C. to 100° C.

The reaction time is not particularly limited and usually the time when an optically active alcohol represented by general formula (XI) disappeared from the reaction system, may be regarded as terminating point of the reaction.

Recovery of an optically active benzyloxybenzene derivative represented by general formula (VIII) from the reaction mixture is carried out for example by adding after-treatment procedures such as extraction, separation, concentrating, etc.

An optically active alcohol represented by general formula (XI) may be also prepared by for example, processes shown hereinafter. That is;

i) The optically active alcohol wherein Z' is

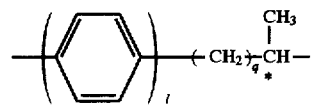

may be also prepared by reacting an optically active diol represented by general formula (XVII)

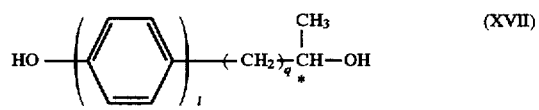

wherein q represents an integer of 1–5, 1 represents 1 or 2, * symbol represents an asymmetric carbon atom, with a benzyl halide represented by general formula (XVI)

wherein $Y_1$ represents a halogen atom, in a solvent in the presence of a base. As bases, alkalimetalcarbonates such as sodium carbonate or potassium carbonate; alkali metal hydroxides such as sodium hydroxide or potassium hydroxide; alkali metal alcoholates such as sodium methylate or sodium ethylate are exemplified.

The base is required in amount of 1 equivalent-fold or more based on optically active diols (XVII), and usually 1–5 equivalent-folds are used.

As solvents, solvents which are inert to the reaction, for example, ether type solvents such as tetrahydrofuran, dioxane, ethyl ether, etc.; ketone type solvents such as acetone, methylethylketone, etc.; or aprotic polar solvents such as dimethylformamide, dimethylsulphoxide, N-methylpyrrolidone, etc. are used alone or as a mixture thereof.

As benzyl halides represented by general formula (XVI), benzyl chloride or benzylbromide, etc. are actually exemplified and they are required in an amount of 1 equivalent-fold or more based on optically active diols represented by general formula (XVII) and although the upper limit of the amount is not particularly restricted, 1–5 equivalent-folds are usually employed.

The reaction is carried out at a temperature of usually −20° C. to 150° C., more preferably 0° C. to 130° C.

The reaction time is not particularly limited and the time when an optically active diol represented by general formula (XVII) disappeared from the reaction system may be regarded as terminal point of the reaction.

Recovery of the optically active alcohols represented by general formula (XI) from the reaction mixture is carried out for example by adding after-treatment procedures such as extraction, separation, concentration, etc.

Optically active diols represented by general formula (XVII) may be prepared by hydrolysing optically active acyloxybenzenes represented by general formula (XVIII)

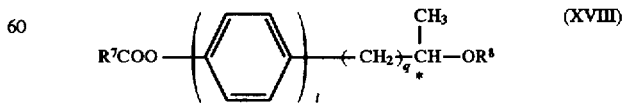

wherein $R^7$ represents a lower alkyl group, $R^8$ represents hydrogen atom or an alkylcarbonyl group having 2–6 carbons, q represents an integer of 1–5, 1 represents 1 or 2 and * symbol represents an asymmetric carbon atom.

The hydrolysis is carried out usually in the co-presence of an acid or a base.

As the acid, for example, inorganic acids such as sulfuric acid, phosphoric acid, hydrochloric acid, etc.; organic acids such as toluenesufonic acid, methanesulfonic acid may be recited. Further as the base, for example, inorganic bases such as sodium hydroxide, potassium hydroxide, barium hydroxide, potassium carbonate, etc.; or organic bases such as 1,8-diazabicyclo[5,4,0]7-undecene, etc. may be recited.

The acids are preferably used in an amount of ordinarily 0.01–10 equivalent-folds based on optically active acyloxybenzenes (XVIII) and the bases are required in an amount of 1 equivalent-fold or more based on optically active acyloxybenzenes represented by general formula (XVIII) wherein $R^8$ represents hydrogen atom and the bases is required in an amount of 2 equivalent-folds or more based on said acyloxybenzenes (XVIII) wherein $R^8$ represents an alkylcarbonyl group having 2–6 carbon atoms and although the upper limit of the amount is not particularly restricted, it is ordinarily 10 equivalent-folds or less.

The hydrolysis is preferably carried out in the presense of a solvent and as such a solvent, a solvent alone or a mixture of solvents which are inert to the reaction, for example, alcohols such as methanol, ethanol, propanol, etc.; or ketones such as acetone, methylethylkenton, etc.; or halogenated hydrocarbons such as chloroform, dichloromethane, etc.; or hydrocarbons such as tolune, xylene, hexane, heptane, etc.; or ethers such as ethylether, tetrahydrofuran, dioxane, etc. or aprotic polar solvents such as dimethylformamide, N-methylpyrrolidone, etc. are exemplified. The using amount of these solvents is not particularly limited.

The reaction is usually carried at a temperature of $-30°$ C. to $150°$ C., more preferably $-20°$ C. to $100°$ C.

The reaction time is not particularly limited and the time when optically active acyloxybenzenes represented by general formula (XVIII) disappeared from the reaction system may be regarded as terminal point of the reaction.

Recovery of the optically active diols represented by general formula (XVII) from the reaction mixture is carried out for example by adding usual after-treatment procedures such as extraction, separation, concentration, recrystalization or column chromatogarphy, etc.

Optically active acyloxybenzenes represented by general formula (XVIII) may be prepared by effecting Baeyer-Villiger oxidation of optically active acylbenzenes represented by general formula (XIX)

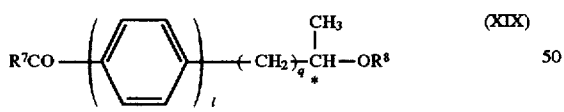

wherein $R^7$ represents a lower alkyl group, $R^8$ represents hydrogen atom or an alkylcarbonyl group having 2–6 carbon atoms, q represents an integer of 1–5, l represents 1 or 2 and * symbol represents an asymmetric carbon atom, in the presence of a solvent.

As the oxidizing agent used in the Baeyer Villiger oxidation, for example, peracids such as peracetic acid, performic acid, metachloroperbenzoic acid, perbenzoic acid, etc. ar exemplified. Such peracids may be formed from for example the corresponding acid and hydrogen peroxide, and the Baeyer Villiger oxydation may be also carried out while synthesizing the peracid in the reaction system.

The peracids are usually required in an amount of 1-equivalent-fold or more based on optically active acylbenzenes represented by general formula (XIX) and although the upper limit is not particularly restricted, preferably 1–2 equivalent-fold are used.

As the solvents used in this Baeyer Villiger oxidation, a solvent alone or a mixture of solvents which are usually inert to the oxidation reaction are used and as the solvents, for example halogenated hydrocarbons, aromatic hydrocarbons or aliphatic hydrocarbons, etc. such as dichloromethane, dichloroethane, chloroform, chlorobenzene, benzene, toluene, xylene, hexane, cyclohexane, etc. are examplified.

The reaction is carried out at a temperature of usually, $-20°$ C. to $130°$ C., preferably $10°$ C. to $100°$ C.

Recovery of optically active acyloxybenzenes represented by general formula (XVIII) from the reaction mixture is carried out by adding usual after-treatment procedures such as removing of excess per acids, filtration, extraction, separation or concentration, etc.

Optically active acylbenzenes represented by general formula (XIX) may be prepared by asymmetric-hydrolysing esters represented by general formula (XX)

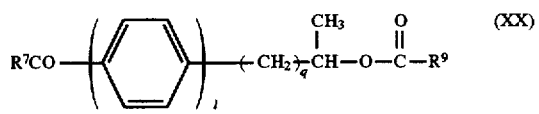

wherein $R^7$, l and q are as defined above and $R^9$ represents an alkyl group having 1–5 carbon atoms, with esterases capable of hydrolysing only anyone isomer of optical isomers of said esters.

Esters represented by general formula (XX) may be prepared by acylating alkylesters represented by general formula (XXI)

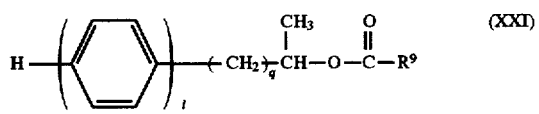

wherein $R^9$, l and q are as defined above, by using Friedel-Crafts reaction.

Further, alkyl esters (XXI) are prepared by esterifying the corresponding alcohol compound.

With reference to said alcohol compound, the alcohol compound having one methylene group in case of l=2 is known, and the alcohol compound having 2–5 methylene groups is prepared by reducing the corresponding ketone compound.

Said ketone compound having 2 methylene groups is prepared by hydrolysing ketoesters represented by general formula (XXXI)

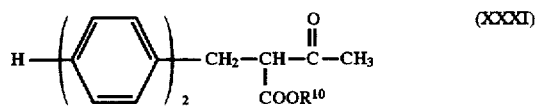

wherein, $R^{10}$ represents a lower alkyl group, under basic condition and further decarbonating under acidic condition. Further, said ketone compound having 3–5 methylene groups may be obtained by for example, cross-coupling a Grignard's compound represented by general formula (XXXII)

wherein q represents an integer of 3–5, with biphenyl iodide or biphenyl bromide for example in the presence of a nickel catalyst such as nickel bromide, etc. to provide a ketal represented by general formula (XXXIII)

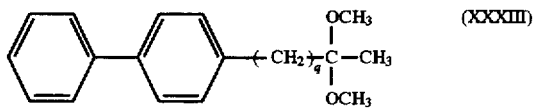

wherein q is as defined above, and then hydrolysing said ketal by using sulfuric acid as a catalyst.

ii) Optically active alcohols represented by general formula (XI) wherein Z' is

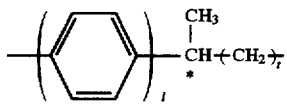

may be obtained by reducing optically active arylalkyl carboxylic acids represented by general formula (XII)

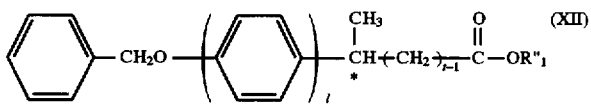

wherein l, t and * symbol are as defined above, $R_1''$ represents hydrogen atom or a lower alkyl group, with a reducing agent in a solvent.

As such a reducing agent, suitably, sodium boro hydride, lithium aluminium hydride or boron hydride is used and it is required in an amount of at least 1 equivalent-fold or more, based on an optically active arylalkyl carboxylic acid (XII) and ordinally 1–10 equivalent-folds are employed.

As the solvents, a solvent alone or a mixture of solvents which are inert to the reaction, for example, ethers, (halogenated) hydrocarbons or alcohols such as tetrahydrofuran, dioxane, ethylether, methanol, ethanol, n-propyl alcohol, isopropyl alcohol, toluene, benzene, chloroform, dichloromethane, are recited.

The reaction is carried out at a temperature of ordinally, –30° C. to 100° C., preferably –20° C. to 90° C.

The recovery of optically active alcohols [wherein Z' is

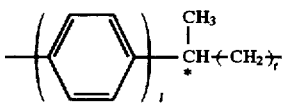

in the formura (XI)] from the reaction mixture is carried out for example by adding after-treatment procedures such as separation, concentration, distillation or crystallization, etc.

Optically active arylalkyl carboxylic acids represented by general formula (XII) may be prepared by benzylating an optically active hydroxybenzene derivative represented by general formula (XIV)

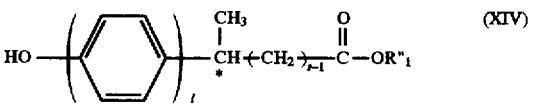

wherein, $R_1''$, l, t and * symbol are as defined above in a solvent, in the presence of a basic catalyst or dehydrating agent.

The benzylation is carried out by using benzyl halides, and as said benzyl halide, for example benzylchloride, benzylbromide, etc. are recited and it is used in an amount of ordinally 1–2 equivalent-folds, preferably 1–1.3 equivalent-folds based on an optically active hydroxybenzene derivative (XIV).

Although the basic catalyst varies by the kind of the solvent, as the basic catalyst usually alkali metal hydroxides or alkaline earth metal hydroxydes such as sodium hydroxide, potassium hydroxide, calcium hydroxide, magnesium hydroxide; salts of carbonic acid such as sodium carbonate, potassium carbonate, sodium hydrogen carbonate, potassium hydrogen carbonate: metal hydrides such as sodium hydride, potassium hydride, calcium hydride, n-butyllithium hydride, sec-butyllithium hydride, etc. are recited. Said basic catalyst is required in an amount of at least 1 equivalent-fold or more based on an optically active hydroxybenzene derivative (XIV), and ordinally 1–10 equivalent-folds are used.

When a metal hydride is used as the basic catalyst, as the solvent, ethers, hydrocarbons and aprotic polar solvents such as ethylether, tetrahydrofuran, dioxane, toluene, benzene, heptane, hexane, dimethylformamide, dimethylsulfoxide are exemplified but when a basic catalyst other than metal hydrides is employed, in addition to solvents recited above, solvents which are inert the reaction, such as ketones, alcohols, halogenated hydrocarbons, etc. such as acetone, methylethylketone, methanol, ethanol, chlorobenzene, chloroform, dichloromethane, dichloroethane, etc., are recited alone or as their mixture.

The reaction is carried out at a temperature of ordinally –70° C. to 150° C., preferably –20° C. to 100° C.

Recovery of optically active arylalkylcarboxylic acids (XII) from the reaction mixture is carried out for example, by adding after-treatment procedures such as separation, concentrating, distillation, or crystallization, etc.

Further, the benzylation is also carried out by reacting an optically active hydroxybenzene derivative (XIV) with a benzyl alcohol in a solvent by using triphenylphosphine and diethylazodicarboxylate as the delhydrating agent.

Benzyl alcohol is used ordinally in an amount of 1–2 equivalent-folds based on a hydroxybenzene derivative (XIV). Respective triphenylphosphine and diethylazodicarboxylate are usually used in an amount of 0.9–1.1 equivalent-fold based on the benzyl alcohol. As solvents, for example, ethers etc. such as terahydrofuran or diethyl ether are preferably used and the using amount thereof is not particularly limited. Recovery of optically active arylalkyl carboxylic acids (XII) from the reaction mixture is carried out for example by adding after-treatment procedures such as concentrating, colum chromatography, etc.

An optically active hydroxybenzene derivative (XIV) is prepared by for example the processes mentioned hereinbelow.

(1) When t is an integer of 1–2:

Said derivative wherein $R_1''$ is hydrogen atom is obtained by the process of effecting optical resolution of the corresponding dl-substance by using an amine such as phenethylamine, and further said derivative wherein $R_1''$ is a lower alkyl group is obtained by the process of effecting asymmetric hydrolysis of the corresponding dl-substance by using a esterase.

(2) When t is an integer of 3–5:

Said derivative is obtained by acetylating the phenolic hydroxy group of the corresponding optically active alcohol to provide p-acetoxybenzene derivative, halogenating alcoholic hydroxy group of the resulting derivative to provide resulting p-acetoxy-haloalkylbenzene with an ester of malonic acid to provide malonic acid ester derivative and then hydrolysing and thereafter further decarbonating hydrolyzate of said malonic acid ester derivative.

PREPARATION EXAMPLE (STARTING MATERIAL COMPOUND (V)) 1

38.8 g (0.2 mol) of methyl (+)-3-methyl-3-(4-hydroxyphenyl)propionate (XIV-1), 70 g of anhydrous potassium carbonate and 400 ml of dimethylformamide were charged into a four necked-flask providede with a thermometer and an agitator, and 30.4 g (0.24 mol) of benzylchloride was added, and reacted at 50°–60° C. for 6 hours.

After completing the reaction, the reaction mixture was poured into 1 l of water and extracted by adding 500 ml of chloroform. After thoroughly washing the organic layer with water, the solvent was distilled out under the reduced pressure to provide 55.1 g (yield: 97%) of methyl (+)-3-methyl-3-(4-benzyloxyphenyl)propanoate (XII-1).

54 g (0.19 mol) of the above obtained compound (XII-1) was dissolved in 300 ml of tetrahydrofuran and then dropped into 300 ml of tetrahydrofuran in which 7.2 g (0.19 mol) of lithium aluminium hydride was suspended. After agitating at temperature of 30°–40° C. for 3 hours, ethanol was carefully added in the reaction mixture and then poured into 1 l of water and then adjusted to pH 2–3 by hydrochloric acid and thereafter extracted by adding 300 ml of toluene. After washing the organic layer with 5% aqueous solution of sodium bicarbonate, the solvent were distilled out under the reduced pressure to provide 46.7 g (yield: 96%) of (+)-3-methyl-3-(4-benzyloxyphenyl)propanol (XI-1).

After 2.56 g (10 millimols) of above obtained compound (XI-1) was dissolved in 20 ml of dimethylformamide, 0.48 g (12 millimols) of 60% sodium hydride was added at temperature of 25°–35° C. and then agitated for two hours. Thereafter, 3.0 g (14 millimols) of propyl paratoluene sulfonate was added and reacted for 4 hours. After completing the reaction, the reaction mixture was poured into 300 ml of water and liquid-separated and then the organic layer was further washed with water and then dried on anhydrous magnesium sulfate. After distilling out the solvent under the reduced pressure, the resulting residue was purified by silica gel column chromatography (eluent: toluene) to provide 2.86 g (yield: 96%) of (+)-1-propoxy-3-(4-benzyloxy) phenylbutane (VIII-1).

$[\alpha]_D^{20}$+17.7° (C=1, CHCl3), $n_D^{20}$=1.5222

After 1.49 g (5 millimols) of the resulting compound (VIII-1) was dissolved in 20 ml of methanol, the debenzylation was effected by adding 5% Pd/C in an atomosphere of hydrogen. After confirming perfect disappearance of the starting material (VIII-1) when calculated amount of hydrogen was consumed, Pd/C was filtrated out and the methanol solution was concentrated under the reduced pressure to provide 1.04 g (yield: 100%) of (+)-4-(1-methyl-3-propoxypropyl)phenol (V-1).

$[\alpha]_D^{20}$=+28.2° (C=1, CHCl3), $n_D^{20}$=1.5011

PREPARATION EXAMPLE (STARTING MATERIAL COMPOUND (V)) 2–7

Condensation, debenzylation and after-treatment were effected similarly to Preparation Example (starting material compound (V)) 1 except that 2.56 g (10 millimols) of (+)-3-methyl-3-(4-benzyloxyphenyl)propanol (XI-1) obtained in Preparation Example (starting material) 1 was used and alkylating reagents (IX) shown in Table-(i) were used. The results shown in Table-(i) were obtained thereby.

TABLE (i)

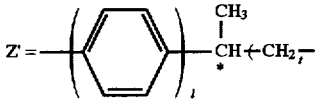

| Preparation Example (Starting Material) | Alkylating agent (IX) and it's use amount | Optically active phenols (V) $R_2$ | l | t | s | ** yield (%) | $[\alpha]_D^{20}$ (c = 1, CHCl3) |
|---|---|---|---|---|---|---|---|
| 2 | Paratoluenesulfonic acid pentyl ester (3.39 g) | n-$C_5H_{11}$ | 1 | 2 | 0 | 93 | +26.2° |
| 3 | Paratoluenesulfonic acid octyl ester (3.98 g) | n-$C_8H_{17}$ | 1 | 2 | 0 | 91 | +23.1° |
| 4 | Paratoluenesulfonic acid hexadecyl ester (5.55 g) | n-$C_{16}H_{33}$ | 1 | 2 | 0 | 95 | +13.1° |
| 5 | Paratoluenesulfonic acid 2(S)-fluoroheptyl ester (3.46 g) | F<br>\|<br>—$CH_2$—$\overset{*}{CH}$—$C_5H_{11}$ | 1 | 2 | 0 | 86 | +20.1° |
| 6 | Paratoluenesulfonic acid 2(S)-methylbutyl ester (2.91 g) | $CH_3$<br>\|<br>—$CH_2$—$\overset{*}{CH}$—$C_2H_5$ | 1 | 2 | 0 | 96 | +20.5° |
| 7 | Paratoluenesulfonic acid ethoxypropyl ester (3.1 g) | $(CH_2)_3$—O—$C_2H_5$ | 1 | 2 | 0 | 90 | +19.1° |

**Yield = $\dfrac{\text{(yield of condensation)}}{100}$ × $\dfrac{\text{(Recovery of pure portion on purification)}}{100}$ × (yield of debenzylation)

PREPARATION EXAMPLE (STARTING MATERIAL COMPOUND (V)) 8

77.6 g (0.4 mol) of ethyl(−)-2-(4-hydroxyphenyl)propionate (XIV-8), 48.6 g (0.45 mol) of benzylalcohol, 108 g (0.41 mol) of triphenylphosphine and 300 ml of tetrahydrofuran were charged into a four mouths-flask provided with a thermometer and an agitator, and 58.2 g (0.41 mol) of diethylazodicarboxylate was dropped at 0° C. After the temperature was elevated to 20° C., the mixture is agitated for one day at the same temperature and then the reaction mixture was concentrated. The resulting residue was separated by silica gel column chromatography to provide 85.9 g (yield: 72%) of (−)-ethyl 2-{4-(p-methylbenzyloxyphenyl}propionate (XII-8).

Reduction, condensation, debenzylation and after-treatment of 56.6 g (0.19 mol) of the resulting compound (XII-8) were carried out in accordance with Preparation Example (starting material) 1 to provide 0.96 g (yield: 99.5%) of (+)-4-(1-methyl-2-propoxyethyl)phenol (V-8).

$[\alpha]_D^{20}$=+3.0° (C=1, CHCl3)

appearance of the starting material (VIII-9) when calculated amount of hydrogen (about 100 ml) was consumed, Pd/C was filtrated out and the resulting methanol solution was concentrated under the reduced pressure to provide 1.18 g (yield: 99.5%) of (+)-4-(1-methyl-3-butyryloxypropyl)phenol (V-9).

$[\alpha]_D^{20}$=+18.0° (C=1, CHCl3)

PREPARATION EXAMPLE (STARTING MATERIAL COMPOUND (V)) 10–12

Condensation, debenzylation reaction and after-teatment were carried out in accordance with Preparation Example (starting material) 9 except that 2.56 g (10 millimols) of (+)-3-methyl-3-(4-benzyloxyphenyl)propanol (XI-1) obtained in Preparation Example (starting material) 1 was used and acylating agents shown in Table-(ii) was used. The results shown in Table-(ii) were obtained thereby.

TABLE (ii)

$$Z' = -\left(\!\!\!\bigcirc\!\!\!\right)_l - \underset{*}{CH} \overset{CH_3}{\underset{|}{-}} CH_2 -$$

| Preparation Example (Starting Material) | Acylating agent and it's use amount | Optically active phenols (V) R₂ | l | t | s | ** yield (%) | $[\alpha]_D^{20}$ (c = 1, CHCl₃) |
|---|---|---|---|---|---|---|---|
| 10 | Hexanoyl chloride (1.75 g) | n-C₅H₁₁ | 1 | 2 | 1 | 95 | +17.9° |
| 11 | Nonanoyl chloride (2.29 g) | n-C₈H₁₇ | 1 | 2 | 1 | 94 | +16.8° |
| 12 | (S)-2-methylbutyryl chloride (1.57 g) | CH₃<br>\|<br>—CH—C₂H₅<br>* | 1 | 2 | 1 | 95 | +19.1° |

$$**\text{Yield} = \frac{\text{(yield of condensation)}}{100} \times \frac{\text{(Recovery of pure portion on purification)}}{100} \times \text{(yield of debenzylation)}$$

PREPARATION EXAMPLE (STARTING MATERIAL COMPOUND (V)) 9

2.56 (10 millimols) of (+)-3-methyl-3-(4-benzyloxyphenyl)propanol (XI-1) obtained in Preparation Example (starting material compound (V)) 1, was dissolved in 20 ml of pyridine and 1.38 g (13 millimols) of butyrylchloride was added at 30°–40° C. and reacted for 2 hours. The reaction mixture was poured into 200 ml of water and extracted with 200 ml of toluene and separated and then washed with, in the order, 1N aqueous solution of hydrochloric acid, water, 5% aqueous solution of sodium bicarbonate and water, and thereafter dried on anhydrous magnesium sulfate. After the solvent was distilled out under the reduced pressure, the resulting residue was purified by silica gel column chromatography (eluent: toluene-ethyl acetate) to provide 3.1 g (yield: 95%) of (+)-4-benzyloxy-1-(1-methyl-3-butyryloxypropyl)benzene (VIII-9).

1.63 g (5 millimols) of the resulting compound (VIII-9) was dissolved in 200 ml of methanol and 0.1 g of 5% Pd/C was added and the debenzylation reaction was carried out in an atomosphere of hydrogen. After confirming perfect dis-

PREPARATION EXAMPLE (STARTING MATERIAL COMPOUND (V)) 13

29.6 g (0.1 mol) of (−)-4-acetyl-4'-(2-acetoxypropyl)biphenyl (XIX-13) ([α]_D^{20}=−9.9° (C=1, CHCl₃)} was charged into a four necked-flask provided with a thermometer and an agitator, and dissolved by adding 200 ml of dichloromethane. 20.7 g (0.12 mol) of m-chloroperbenzoic acid was added in this solution and agitated at reflux for 8 hours. After excess of m-chloroperbenzoic acid was decomposed by adding 10% aqueous solution of sodium hydrogen sulfite to the reaction mixture, the organic layer was washed with 10% aqueous solution of sodium bicarbonate and then with water, and dried an anhydrous magnesium sulfate. The resulting dichloromethane solution was concentrated under the reduced pressure to provide 30.2 g (yield: 97%) of (−)-4-acetoxy-4'-(2-acetoxypropyl)biphenyl (XVIII-13).

$[\alpha]_D^{20}$=−9.0° (C=1, CHCl₃)

Then, 28.1 g (90 millimols) of the above obtained compound (XVIII-13) was dissolved in 200 ml of methanol, and 50 ml of 20% aqueous solution of sodium hydroxide was added and agitated at a room temperature for 2 hours.

After pH was adjusted to 1–2 by adding 10% hydrochloric acid to the reaction mixture, almost of methanol was distilled out. The resulting residue was extracted with ethyl acetate. The resulting organic layer was washed with 5% aqueous solution of sodium bicarbonate and then with water, and dried on anhydrous magnesium sulfate. The resulting ethyl acetate solution was concentrated under the reduced pressure to provide 20.5 g (yield: 100%) of (+)-4-hydroxy-4'-(2-hydroxypropyl)biphenyl (XVII-13).

$[\alpha]_D^{20}=+9.6°$ (C=1, CH$_3$OH)

Then, 18.3 g (80 millimols) of the above obtained compound (XVII-13) was dissolved in 100 ml of dimethylformamide, and thereto 12.2 g (96 millimols) of benzylchloride and 22.1 g (0.16 mol) of pottasium carbonate were added and agitated at 50°–60° C. for 5 hours.

The reaction mixture was poured into 200 ml of water and extracted with ethyl acetate. The resulting organic layer was washed with water and then with saturated aqueous solution of NaCl, and then dried on anhydrous magnesium sulfate and thereafter the resulting ethyl acetate solution was concentrated under the reduced pressure. The resulting yellow solid was recrystallized from ethanol to provide 19.1 g (yield: 75%) of (+)-4-benzyloxy-4'-(2-hydroxypropyl) biphenyl (XI-13).

$[\alpha]_D^{20}=+7.7°$ (C=1, CHCl$_3$)

Then, 3.2 g (10 millimols) of the above obtained compound (XI-13) and 3.7 g (30 millimols) of 1-bromopropane were dissolved in 30 ml of dimethylsulfoxide, and 0.8 g (20 millimols) of 60% sodium hydride was added and then agitated at 80° C. for 12 hours. The reaction mixture was poured into 50 ml of water and extracted with toluene. The organic layer was washed with water and then with saturated aqueous solution of NaCl, and dried on anhydrous magnesium sulfate, and thereafter the resulting toluene solution was concentrated under the reduced pressure. The resulting residue was subjected to silica gel column chromatography (eluent: toluene/hexane=5/1) to provide 2.5 g (yield: 68%) of (+)-4-benzyloxy-4'-(2-propoxypropyl)biphenyl (VIII-13).

$[\alpha]_D^{20}=+5.8°$ (C=1, CHCl$_3$)

Then 1.8 g (5 millimols) of the above obtained compound (VIII-13) was dissolved in 5 ml of ethyl acetate and further diluted with 80 ml of ethanol and thereafter 0.3 g of 10% Pd/C was added and agitated vigorously under the hydrogen pressure of 1–1.2 atomospheric pressure for 10 hours.

After completing the reaction, Pd/C was filtrated out and the filtrate was concentrated to provide 1.4 g (yield: 100%) of (+)-4-hydroxy-4'-(2-propoxypropyl)biphenyl (V-13).

$[\alpha]_D^{20}=+9.1°$ (C=1, CHCl$_3$). M.P.=88°–90° C.

PREPARATION EXAMPLE (STARTING MATERIAL COMPOUND (V)) 14–15

The reaction and after-treatment were carried out similarly to Preparation Example (starting material) 13 except that (−)-4-acetyl-4'-(3-acetoxybutyl)biphenyl (XIX-14) {$[\alpha]_D^{20}=-9.1°$ (C=1, CHCl$_3$)} or (−)-4-acetyl-4'-(4-acetoxypentyl)biphenyl (XIX-15) {$[\alpha]_D^{20}=-3.4°$ (C=1, CHCl$_3$)} was used in place of (−)-4-acetyl-4'-(2acetoxypropyl)biphenyl (XIX-13). The results are shown in Table-(iii).

PREPARATION EXAMPLE (STARTING MATERIAL COMPOUND (V)) 16–18

The alkylation reaction, the reactions thereafter and after-treatment were carried out in accordance with Preparation Example (starting material) 13, by using (+)-4-benzyloxy-4'-(2-hydroxypropyl)biphenyl as starting compound except that alkylating agents (IX) shown in Table-(iv) are used in place of 1-bromopropane. The results are shown in Table-(iv).

TABLE (iii)

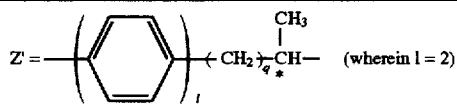

Z' = —[phenyl]—(CH$_2$)$_q$—CH(CH$_3$)—   (wherein l = 2)

| Preparation Example (Starting Material) | Optically active acylbenzene (XIX) | | | | Optically active acyloxybenzenes (XVIII) | | Optically active diols (XVII) | | Optically active alcohols (XI) | |
|---|---|---|---|---|---|---|---|---|---|---|
| | R$^7$ | R$^8$ | q | Mol | Yield (%) | $[\alpha]_D^{20}$ (c = 1, CHCl$_3$) | Yield (%) | $[\alpha]_D^{20}$ (c = 1, CHCl$_3$) | Yield (%) | $[\alpha]_D^{20}$ (c = 1, CHCl$_3$) |
| 14 | CH$_3$- | O‖—C—CH$_3$ | 2 | 0.1 | 98 | −8.3° | 99.8 | +9.0° | 78 | +6.0° |
| 15 | " | " | 3 | " | 97 | −2.7° | 99.9 | +5.4° | 76 | +3.3° |

| Optically active benzyloxy benzene derivative (VIII) | | Optically active phenols (V) (wherein s = 0) | | | | M.P. or refractive index |
|---|---|---|---|---|---|---|
| Yield (%) | $[\alpha]_D^{20}$ (c = 1, CHCl$_3$) | R$_2$ | q | Yield (%) | $[\alpha]_D^{20}$ (c = 1, CHCl$_3$) | |
| 68 | +6.3° | -n-C$_3$H$_7$ | 2 | 99.9 | +8.5° | 91–93° C. |
| 73 | +2.2° | " | 3 | 99.8 | +2.4° | n$_D^{20}$ 1.5562 |

TABLE (iv)

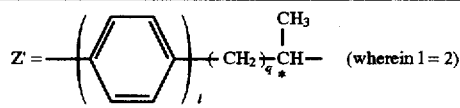

(wherein l = 2)

| Preparation Example (Starting Material) | Optically active alcohols (XI) | | Alkylating agent (IX) | | | Optically active benzyloxybenzene derivative (VIII) (wherein s = 0) | | | | Optically active phenols (V) (wherein s = 0) | | | |
|---|---|---|---|---|---|---|---|---|---|---|---|---|---|
| | q | Mol | $R_2$ | Q | Mol | $R_2$ | q | Yield (%) | $[\alpha]_D^{20}$ (c = 1, CHCl$_3$) | $R_2$ | q | Yield (%) | $[\alpha]_D^{20}$ (c = 1, CHCl$_3$) |
| 16 | 1 | 0.01 | n-C$_5$H$_{11}$— | —Br | 0.03 | n-C$_5$H$_{11}$— | 1 | 65 | +5.2° | n-C$_5$H$_{11}$— | 1 | 99.9 | +8.8° |
| 17 | " | " | n-C$_8$H$_{17}$— | " | " | n-C$_8$H$_{17}$— | " | 62 | +4.5° | n-C$_8$H$_{17}$— | " | 98 | +8.0° |
| 18 | " | " | n-C$_{16}$H$_{33}$— | " | " | n-C$_{16}$H$_{33}$— | " | 55 | +3.3° | n-C$_{16}$H$_{33}$— | " | 99 | +6.7° |

PREPARATION EXAMPLE (STARTING MATERIAL COMPOUND (V)) 19

3.2 g (10 millimols) of (+)-4-benzyloxy-4'-(2-hydroxypropyl)biphenyl (XI-13) obtained in Preparation Example (starting material) 13 was dissolved in 30 ml of pyridine and cooled to 0°–5° C. 1.1 g (12 millimols) of propionic acid chloride was dropped into this solution at the same temperature and thereafter, the temperature was elevated to the room temperature and agitated for 5 hours.

The reaction mixture was poured into 50 ml of water and extracted with ethyl acetate. The resulting organic layer was washed with, in the order, 10% hydrochloric acid, water, 5% aqueous solution of sodium bicarbonate, and saturated aqueous solution of NaCl, and dried on anhydrous magnesium sulfate. The resulting ethyl acetate solution was concentrated under the reduced pressure to provide 3.7 g (yield: 100%) of (−)-4-benzloxy-4'-(2-propanoyloxypropyl)biphenyl (VIII-19).

$[\alpha]_D^{20}$=−7.0° (C=1, CHCl$_3$).

Then, 1.9 g (5 millimols) of the above obtained compound (VIII-19) was dissolved in 20 ml of toluene and diluted with 80 ml of ethanol and thereafter, 0.2 g of 10% Pd/C was added and agitated vigorously under the hydrogen pressure of 1–1.2 atm. for 12 hours.

After completing the reaction, Pd/C was filtrated out and the resulting filtrate was concentrated under the reduced pressure to provide 1.4 g (yield: 98%) of (−)-4-hydroxy-4'-(2-propanoyloxypropyl)biphenyl (V-19).

$[\alpha]_D^{20}$=−11.5° (C=1, CHCl$_3$). $n_n^{20}$=1.5462.

PREPARATION EXAMPLE (STARTING MATERIAL COMPOUND (V)) 20–21

The reaction and after-treatment were carried out similarly to Preparation Example (starting material) 19 except that (+)-4-benzyloxy-4'-(3-hydroxybutyl)biphenyl (XI-14) obtained in Preparation Example (starting material) 14 or (+)-4-benzyloxy-4'-(4-hydroxypentyl)biphenyl (XI-15) obtained in Preparation Example (starting material) 15 was used as starting compound in place of (+)-4-benzyloxy-4'-(2-hydroxypropyl)biphenyl (XI-13). The results are shown in Table-(v).

PREPARATION EXAMPLE (STARTING MATERIAL COMPOUND (V)) 22–24

The reaction and after-treatment were carried out in accordance with Preparation Example (starting amterial)19 except that acylating agents shown in Table-(vi) was used in place of propionic acid chloride. The results are shown in Table-(vi).

TABLE (v)

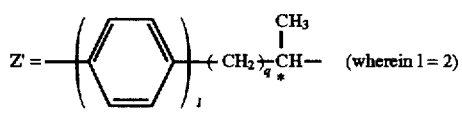

(wherein l = 2)

| Preparation Example (Starting Material) | Optically active alcohols (XI) | | Alkylating agent | | | Optically active benzyloxybenzene derivative (VIII) (wherein s = 1) | | | | Optically active phenols (V) (wherein s = 1) | | | | Refractive index |
|---|---|---|---|---|---|---|---|---|---|---|---|---|---|---|
| | q | Mol | Structure | Mol | $R_2$ | q | Yield (%) | $[\alpha]_D^{20}$ (c = 1, CHCl$_3$) | $R_2$ | q | Yield (%) | $[\alpha]_D^{20}$ (c = 1, CHCl$_3$) | $n_D^{20}$ |
| 20 | 2 | 0.01 | C$_2$H$_5$COCl | 0.012 | C$_2$H$_5$ | 2 | 99.9 | −9.4° | C$_2$H$_5$ | 2 | 98 | −9.7° | 1.5408 |
| 21 | 3 | " | " | " | " | 3 | " | −6.0° | " | 3 | 97 | −6.5° | 1.5392 |

TABLE (vi)

$$Z' = -\left(\!\!\bigcirc\!\!\right)_l\!\!-\!(CH_2)_q\!-\!\underset{*}{\overset{CH_3}{\underset{|}{CH}}}\!-\quad \text{(wherein } l = 2)$$

| Preparation Example | Optically active alcohols (XI) | | Alkylating agent | | Optically active benzyloxybenzene derivative (VIII) (wherein s = 1) | | | | Optically active phenols (V) (wherein s = 1) | | | |
|---|---|---|---|---|---|---|---|---|---|---|---|---|
| (Starting Material) | q | Mol | Name | Mol | $R_2$ | q | Yield (%) | $[\alpha]_D^{20}$ (c = 1, CHCl$_3$) | $R_2$ | q | Yield (%) | $[\alpha]_D^{20}$ (c = 1, CHCl$_3$) |
| 22 | 1 | 0.01 | hexanoyl bromide | 0.012 | n-C$_5$H$_{11}$ | 1 | 99.9 | −6.3° | n-C$_5$H$_{11}$ | 1 | 97 | −9.5° |
| 23 | " | " | nonanoyl chloride | " | n-C$_8$H$_{17}$ | " | 99.9 | −5.5° | n-C$_8$H$_{17}$ | " | 98 | −8.8° |
| 24 | " | " | heptadecanoyl chloride | " | n-C$_{16}$H$_{33}$ | " | 98 | −4.2° | n-C$_{16}$H$_{33}$ | " | 99 | −6.7° |

PREPARATION EXAMPLE (STARTING MATERIAL COMPOUND (V)) 25

25.4 g (0.1 mol) of (−)-4-acetyl-4'-(2-hydroxypropyl)biphenyl (XIX-25) {[α]$_D^{20}$=11.0° (C=1, CHCl$_3$)}, was charged into a four necked-flask provided with a thermometer and an agitator and dissolved by adding 200 ml of dichloromethane, and thereafter, 20.7 g (0.12 mol) of m-chloroperbenzoic acid was added and then agitated at the room temperature for 24 hours.

The reaction mixture was washed with, in the order, 10% sodium hydrogen sulfite, 5% aqueous solution of sodium bicarbonate water and saturated aqueous solution of NaCl and dried on anhydrous magnesium sulfate.

The resulting dichlorometane solution was concentrated under the reduced pressure to provide 26.7 g (yield: 99%) of (−)-4-acetoxy-4'-(2-hydroxypropyl)biphenyl (XVIII-25).

[α]$_D^{20}$=−10.3° (C=1, CHCl$_3$).

Then, after 24.3 g (90 millimols) of the above obtained compound (XVIII-25) was dissolved in 150 ml of methanol, 30 ml of 20% aqueous solution of sodium hydroxide was added and agitated at the room temperature for 2 hours.

The pH of the reaction mixture was adjusted to 1–2 by adding 10% hydrochloric acid and thereafter extracted with ethyl acetate. The resulting organic layer was washed with, in the order, water, 5% aqueous solution of sodium bicarbonate and saturated aqueous solution of NaCl and dried on anhydrous magnesium sulfate. The resulting ethyl acetate solution was concentrated under the reduced pressure to provide 20.5 g (yield: 100%) of (−)-4-hydroxy-4'-(2-hydroxypropyl)biphenyl (XVII-25).

[α]$_D^{20}$=−9.7° (C=1, CHCl$_3$).

Then, 18.3 g (80 millimols) of the above obtained compound (XVII-25) was dissolved in 100 ml of dimethylformamide, and 12.2 g (96 millimols) of benzyl chloride and 22.1 g (0.16 mol) of potassium carbonate were added to this solution and agitated at 50°–60° C. for 8 hours.

The reaction mixture was poured into 200 ml of water and extracted with ethyl acetate. The resulting organic layer was washed with water and then with saturated aqueous solution of NaCl and dried on anhydrous magnesium sulfate. The resulting ethyl acetate solution was concentrated under the reduced pressure. The resulting residue was subjected to silica gal column chromatography (eluent: toluene/ethyl acetate=5/1) to provide 25.3 g (yield: 95%) of (−)-4-benzyloxy-4'-(2-hydroxypropyl)biphenyl (XI-25).

[α]$_D^{20}$=−8.0° (C=1, CHCl$_3$).

Then, 3.2 g (10 millimols) of the above obtained compound (XI-25) was dissolved in 20 ml of dimethylformamide, and 0.8 g (20 millimols) of 60% sodium hydride was added and for 1 hour and temperature for 1 hour and thereafter the solution obtained by dissolving 7.7 g (30 millimols) of 3-ethoxypropyl p-toluene sulfonate in 10 ml of dimethylformamide was dropped. After completing the dropping, the temperature was elevated to 50°–60° C. and the mixture was agitated at the same temperature for 24 hours.

The reaction mixture was poured into 50 ml of water and extracted with ethyl acetate. The resulting organic layer was washed with water and then with saturated aqueous solution of NaCl and dried on anhydrous magnesium sulfate.

After the solvent was distilled out, the resulting residue was subjected to silica gel column chromatography (eluent: toluene/ethyl acetate=10/1) to provide 2.8 g (yield: 69%) of (−)-4-benzyloxy-4'-(2-(3-ethoxypropoxy)propyl}biphenyl (VIII-25).

[α]$_D^{20}$=−10.2° (C=1, CHCl$_3$).

2.0 g (5 millimols) of the above obtained compound (VIII-25) was dissolved in 80 ml of ethanol, and 0.4 g of 10% Pd/C was added and agitated vigorously 5 under the hydrogen pressure of 1–1.2 atm. for 10 hours.

After completing the reaction, Pd/C was filtrated out and the resulting filtrate was concentrated to provide 1.6 g (yield: 100%) of (−)-4-hydroxy-4'-{2-(3-ethoxypropoxy)propyl}biphenyl (V-25).

[α]$_D^{20}$=−11.4° (C=1, CHCl$_3$), M.P. 53°–55° C.

PREPARATION EXAMPLE (STARTING MATERIAL COMPOUND (V) 26-27

The alkylating reaction, the reactions thereafter and aftertreatment were carried out similarly to Preparation Example (starting material) 25 except that (+)-4-benzyloxy-4'-(2-hydroxypropyl)biphenyl (XI-13) obtained in Preparation Example (satarting material) 13 or (+)-4-benzyloxy-4'-(3-hydroxybutyl)biphenyl (XI-14) obtained in Preparation Example (starting material) 14 was used as starting material in place of (−)-4-benzyloxy-4'-(2-hydroxypropyl)biphenyl (XI-25). The results are shown in Table-(vii).

PREPARATION EXAMPLES (STARTING MATERIALS COMPOUND (V)) 28-30

Alkylation and the following reactions with aftertreatment thereof were conducted according to the procedure of Preparation Example (starting material) 25, except that (−)-4-benzyloxy-4'-(2-hydroxypropyl)biphenyl (XI-25) was used as a starting material and the alkylation agent (IX) shown in Table-(viii) was used in place of 3-ethoxypropyl p-toluene sulfonate. The results are shown in Table-(viii).

paratoluenesulfonate, n-octyl paratoluenesulfonate and hexadecyl paratoluenesulfonate, which were then followed by debenzylation to obtain (+)-4-hydroxy-4'-(1-methyl-3-pentyloxypropyl)biphenyl (V-31), (−)-4-hydroxy-4'-(1-methyl-2-octyloxyethyl)biphenyl (V-32) and (+)-4-hydroxy- TABLE (vii)

$$Z' = -\left(\!\!\bigcirc\!\!\right)_l \!\!-\!(CH_2)_q\!-\!\overset{CH_3}{\underset{*}{CH}}\!- \quad \text{(wherein } l = 2\text{)}$$

| Preparation Example (Starting Material) | Optically active alcohols (XI) | | Alkylating reagent (IX) | | Optically active benzyloxybenzene derivative (VIII) (wherein s = 0) | | | | Optically active phenols (V) (wherein s = 0) | | | |
|---|---|---|---|---|---|---|---|---|---|---|---|---|
| | Mol number used | q | Name | Mol number used | $R_2$ | q | Yield (%) | $[\alpha]_D^{20}$ (c = 1, CHCl$_3$) | $R_2$ | q | Yield (%) | $[\alpha]_D^{20}$ (c = 1, CHCl$_3$) | Melting point |

| 26 | 1 | 0.01 | 3-ethoxypropyl p-toluene sulfonate | 0.03 | C$_2$H$_5$O(CH$_2$)$_3$— | 1 | 65 | +8.1° | C$_2$H$_5$O(CH$_2$)$_3$— | 1 | 99.9 | +9.2° | 47–49° C. |
| 27 | 2 | " | 3-ethoxypropyl p-toluene sulfonate | " | " | 2 | 62 | +5.5° | " | 2 | 98 | +6.2° | 41–43° C. |

TABLE (viii)

$$Z' = -\left(\!\!\bigcirc\!\!\right)_l \!\!-\!(CH_2)_q\!-\!\overset{CH_3}{\underset{*}{CH}}\!- \quad \text{(wherein } l = 2\text{)}$$

| Preparation Example (Starting Material) | Optically active alcohols (XI) | | Alkylating reagent (IX) | | Optically active benzyloxybenzene derivative (VIII) (wherein s = 0) | | | | Optically active phenols (V) (wherein s = 0) | | | |
|---|---|---|---|---|---|---|---|---|---|---|---|---|
| | Mol number used | q | Name | Mol number used | $R_2$ | q | Yield (%) | $[\alpha]_D^{20}$ (c = 1, CHCl$_3$) | $R_2$ | q | Yield (%) | $[\alpha]_D^{20}$ (c = 1, CHCl$_3$) |
| 28 | 1 | 0.01 | 3-methoxyethyl p-toluenesulfonate | 0.03 | CH$_3$O(CH$_2$)$_2$— | 1 | 72 | −12.5° | CH$_3$O(CH$_2$)$_2$— | 1 | 99.9 | −13.2° |
| 29 | " | " | 3-ethoxyethyl p-toluenesulfonate | " | C$_2$H$_5$O(CH$_2$)$_2$— | " | 70 | −11.8° | C$_2$H$_5$O(CH$_2$)$_2$— | " | 99.9 | −12.6° |
| 30 | " | " | 8-methoxyoctyl p-toluenesulfonate | " | CH$_3$O(CH$_2$)$_8$— | " | 52 | −7.7° | CH$_3$O(CH$_2$)$_8$— | " | 98 | −8.6° |

PREPARATION EXAMPLES (STARTING MATERIALS COMPOUND (V)) 31–33

In order to obtain (+)-3-methyl-3-(4'-benzyloxybiphenylyl)propanol (XI-31), (−)-2-methyl-2-(4'-benzyloxybiphenylyl)ethanol (XI-32) and (+)-4-methyl-4-(4'-benzyloxybiphenylyl)butanol (XI-33), the procedure of Preparation Example (starting material) 1 was repeated for benzylation, reduction and after-treatment thereof, except of using (+)methyl 3-methyl-3-(4'-hydroxybiphenylyl) propionate, (+)methyl 2-methyl-2-(4'-hydroxybiphenylyl) acetate and (+)methyl 4-methyl-4-(4'-hydroxybiphenylyl) butyrate were respectively used in place of (+)methyl 3-methyl-3-(4-hydroxyphenyl)propionate (XIV-1).

The thus obtained compounds (XI-31), (XI-32) and (XI-33) were respectively alkylated with n-pentyl paratoluenesulfonate, n-octyl paratoluenesulfonate and hexadecyl paratoluenesulfonate, which were then followed by debenzylation to obtain (+)-4-hydroxy-4'-(1-methyl-3-pentyloxypropyl)biphenyl (V-31), (−)-4-hydroxy-4'-(1-methyl-2-octyloxyethyl)biphenyl (V-32) and (+)-4-hydroxy-4'-(1-methyl-4-hexadecyloxybutyl)biphenyl (V-33), respectively. The respective physical property values are shown in Table-(ix).

PREPARATION EXAMPLE (STARTING MATERIAL COMPOUND (V)) 34

(−)-2-methyl-2-(4'-benzyloxybiphenylyl)ethanol (XI-32) was acylated, debenzylated and after-tretaed in similar manner to those in Preparation Example 9, except of using valeryl chloride in place of butyryl chloride, to obtain (−)-4-hydroxy-4'-(1-methyl-2-butylcarbonyloxyethyl) biphenyl (V-34), whose physical property values are shown in Table-(ix).

TABLE (ix)

| Preparation Example (Starting Material) | Optically active phenols (V) | | | | | $[\alpha]_D^{20}$ (c = 1, CHCl₃) |
|---|---|---|---|---|---|---|
| | 1 | Z' | t | s | R₂ | |
| 31 | 2 | 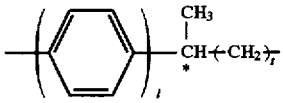 | 2 | 0 | n-C₅H₁₁ | +3.9° |
| 32 | 2 | " | 1 | 0 | n-C₈H₁₇ | −3.3° |
| 33 | 2 | " | 3 | 0 | n-C₁₆H₃₃ | +2.8° |
| 34 | 2 | " | 1 | 1 | n-C₄H₉ | +4.1° |

PREPARATION EXAMPLE (STARTING MATERIAL COMPOUND (III) OR (V) 35

Into a four-necked flask provided with a thermometer and a stirrer, 150 g (1 mol) of 4-phenyl-2-butanol (XXX-35), 500 ml of toluene and 200 ml of pyridine were charged. 122.4 g (1.2 mol) of anhydrous acetic acid and 1 g of 4-dimethylaminopyridine were further added thereto to react them for 4 hours, while temperature being maintained at 40°–50° C. After completion of the reaction, the reaction mixture was poured into 500 ml of 4N hydrochloric acid solution, extracted and fractionated, and then an organic layer was washed with 1N hydrochloric acid, water, 5% sodium bicarbonate solution and water in the order. The thus-obtained organic layer was concentrated under a reduced pressure to obtain 189 g of 2-acetoxy-4-phenylbutane (XXIX-35) with yield of 98.5%.

Secondly, 240 g (1.8 mol) of aluminium chloride and 141 g (1.8 mol) of acetyl chloride were added to 800 ml of anhydrous dichloroethane and stirred for about 1 hr until the aluminum chloride was almost dissolved. Thereafter, the solution was cooled to 0°–5° C., and then thereto a solution of 178 g (0.9 mol) of the above obtained compound (XXIX-35) in 200 ml of dichloroethane was dropwise added, while the same temperature being maintained. After completion of the dropwise addition, the mixture was stirred at the same temperature for two hrs. and then the reaction mixture was poured into 1 l of water, extracted and fractionated. After an organic layer was washed with water, 5% sodium bicarbonate solution, and water in the order, a solvent was distilled off in vacuo therefrom to obtain a yellow oily substance, which was then subjected to a vacuum distillation to obtain 149.7 g of 4-(3-acetoxybutyl)acetophenone (XXVIII-35) with yield of 71%. Boiling point was 131°–134° C., 0.3–0.4 mm Hg.

100 g of thus-obtained compound (XXVIII-35) was suspended in 1 l of 3N phosphoric acid buffer, and then added thereto with 5 g of lipase ("Amano P") while being vigorously stirred at a temperature of 36°±2° C. for 24 hrs. After the reaction was completed, 500 ml of ethyl acetate was added to the reaction mixture and then filtered, which was followed by extraction and fractionation to obtain an organic layer. A solvent was distilled off in vacuo from the organic layer which was water-washed. The obtained residue was separated by a column chromatography (elution medium: toluene-ethyl acetate) to obtain 51.0 g (yield of 51%) of (+)-4-(3-acetoxybutyl)acetophenone and 40.0 g (yield of 48.8%) of (−)-4-(3-hydroxybutyl)acetophenone (XXIII-35).

$[\alpha]_D^{20}$=−12.5° (C=1.2, CHCl₃). (XXIII-35)

To 5.77 g (30 mM) of the above obtained compound (XXIII-35), 15.3 g (90 mM) of propyl iodide and 13.9 g of silver oxide were added, and then te mixture was stirred at room temperature under a shade for 4 days. After completion of the reaction, silver salt was filtered off, and then the filtrate was concentrated to obtain a residue. The residue was separated by a silica gel column chromatography (elution medium: toluene-ethyl acetate) to obtain 4.57 g of (−)-4-(3-propoxybutyl)acetophenone (XXII-35) with yield of 65%.

$[\alpha]_D^{20}$=−10.3° (C=1.2, CHCl₃).

2.0 g of thus-obtained (−)-4-(3-propoxybutyl) acetophenone (XXII-35) along with 100 ml of dioxane were added to an aqueous solution of sodium hypobromite prepared from 100 ml of aqueous solution of 20% sodium hydroxide and 10.9 g (68.3 mM) of bromine. After stirring at room temperature for a day, 20 g of sodium sulfite was added to the reaction mixture while stirring, and the reaction mixture then acidified to pH 1–2 with hydrochloric acid was extracted with 200 ml of ether. The obtained organic layer was washed with saturated NaCl solution, and then dried with an anhydrous magnesium sulfate. Then, a solvent was distilled off in vacuo therefrom to obtain 1.88 g of (−)-4-(3-propoxybutyl)benzoic acid (III-35) with yield of 93%.

$[\alpha]_D^{20}$=−10.4° (C=1, CHCl₃).

Further, 2.0 g of the above obtained compound (XXII-35) was dissolved in 20 ml of dichloromethane, and thereto, 1.2 equivalent (1.77 g) of m-chloroperbenzoic acid was added, and then stirring was continued at room temperature for 24 hrs. After completion of the reaction, the resulting precipitation was filtered off, and then 100 ml of toluene was added to the filtrate to obtain an organic layer which was then washed with water, 5% sodium hydroxide aqueous solution and water in the order, and finally dried with anhydrous magnesium sulfate. From the organic layer a solvent was distilled off under a reduced pressure to obtain 2.09 g of (−)-4-(3-propoxybutyl)acetoxybenzene with yield of 98%.

$[\alpha]_D^{20}$=−10.1° (C=1, CHCl₃).

2.0 g taken from said 2.09 g of (−)-4-(3-propoxybutyl) acetoxybenzene, was added to a mixture solution of 20 ml of methanol, 10 ml of THF and 10 ml of 20% NaOH aqueous solution, and then stirred at room temperature for 6 hrs. After completion of the reaction, the reaction solution was acidified with hydrochloric acid to pH 2–3, and then extracted with 100 ml of ether and fractionated to obtain an organic layer. The organic layer was washed with saturated NaCl aqueous solution, and then a solvent was distilled off therefrom in vacuo to obtain 1.66 g of (−)-4-(3-propoxybutyl)phenol (V-35) with 100% yield.

$[\alpha]_D^{20}$=−9.9° (C=1, CHCl₃). $n_D^{20}$=1.4970.

PREPARATION EXAMPLES (STARTING MATERIALS COMPOUND (III) OR (V)) 36–38

Except that 5.77 g (30 mM) of Compound (XXIII-35) obtained in Preparation Example (starting material compound (III) or (V)) 35 was used and alkylating agent (IX) shown in Table-(x) was also used, the same mol numbers and the same amounts of reagents and solvents were used to conduct reaction and after-treatment. The results as shown in Table-(x) were obtained.

mM) of 60% sodium hydride was added thereto at 20°–30° C. while stirring for 1 hr. Thereafter, 1.15 g (40 mM) of 2(S)-fluoroheptyl paratoluenesulfonate was added. After reaction was effected as such for 2 hrs., the reaction solution was poured into 200 ml of water, which was then extracted TABLE (x)

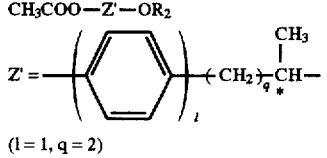

| Preparation Example (Starting Material) | Alkylating agent (IX) | | $R_2$ | Optically active acetophenone derivative (XXII) | | Optically active carboxylic acid compound (III) | | $CH_3COO-Z'-OR_2$ ($l=1$, $q=2$) | | Optically active phenols (V) (wherein s = 0) | |
|---|---|---|---|---|---|---|---|---|---|---|---|
| | Name | Amount used | | Yield (g) & Yield (%) | $[\alpha]_D^{20}$ (c = 1, $CHCl_3$) | Yield (g) & Yield (%) | $[\alpha]_D^{20}$ (c = 1, $CHCl_3$) | Yield (g) & Yield (%) | $[\alpha]_D^{20}$ (c = 1, $CHCl_3$) | Yield (g) & Yield (%) | $[\alpha]_D^{20}$ (c = 1, $CHCl_3$) |
| 36 | Pentyl iodide | 17.8 g (90 mM) | n-$C_5H_{11}$ | 4.88 g (62%) | −9.9° | 1.83 g (91%) | −9.7° | 2.06 g (97%) | −10.2° | 1.66 g (98%) | −16° |
| 37 | Octyl iodide | 21.6 g (90 mM) | n-$C_8H_{17}$ | 5.30 g (58%) | −7.9° | 1.89 g (94%) | −7.5° | 2.02 g (96%) | −8.2° | 1.70 g (98%) | −13° |
| 38 | Hexadecyl iodide | 31.7 g (90 mM) | n-$C_{16}H_{33}$ | 6.38 g (51%) | −6.0° | 1.87 g (93%) | −5.7° | 2.01 g (97%) | −6.2° | 1.77 g (98%) | −7.5° |

PREPARATION EXAMPLE (STARTING MATERIAL COMPOUND (III) OR (V)) 39

25 g of (+)-4-(3-acetoxybutyl)acetophenone obtained in Preparation Example (starting material) 35 was dissolved in a solution of 100 ml of methanol and 50 ml of tetrahydrofuran, and then 50 ml of 20% NaOH aqueous solution was added thereto. The mixture was reacted at a temperature of 30°–40° C. for 6 hrs. After completion of the reaction, the reaction solution was adjusted with 4N hydrochloric acid to pH 8, and then extracted with 300 ml of toluene and fractionated to obtain an organic layer, which was further washesd with water and then dried with anhydrous magnesium sulfate. The organic layer was concentrated under a reduced pressure to obtain 20.2 g of (+)-4-(3-hydroxybutyl)acetophenone (XXIII-39) with yield of 98.5%.

$[\alpha]_D^{20}$=+11.9° (C=1, $CHCl_3$).

7.7 g (40 mM) of the resulting compound (XXIII-39) was dissolved in 40 ml of dimethylformamide, and then 3.2 g (80 mM) of 60% sodium hydride was added thereto at 20°–30° C. while stirring for 1 hr. Thereafter, 1.15 g (40 mM) of 2(S)-fluoroheptyl paratoluenesulfonate was added. After reaction was effected as such for 2 hrs., the reaction solution was poured into 200 ml of water, which was then extracted with 200 ml of toluene and fractionated to obtain an organic layer. This was water-washsed and dried with anhydrous magnesium sulfate. The resulting organic layer was concentrated in vacuo, and then the resulting residue was separated and purified by a silica gel column chromatography (elution medium: toluene-ethyl acetate) to obtain 6.66 g of (+)-4-{3-(2-fluoroheptyl)oxybutyl}acetophenone (XXII-39) with yield of 54%.

Using the thus-obtained compound (XXII-39), reaction and after-treatment were conducted in similar manner to those in Preparation Example (starting material) 35 to obtain the results shown in Table-(xi).

PREPARATION EXAMPLE (STARTING MATERIAL COMPOUND (III) OR (v)) 40

Except of using the compound (XXIII-39) obtained in Preparation Example (starting material) 39 and 9.7 g (40 mM) of 2(S)-methylbutyl paratoluenesulfonate as alkylating agent (IX), reaction and after-treatment were conducted in similar manner to those in Preparation Example (starting material) 39 to obtain the results shown in Table-(xi).

TABLE (xi)

$$Z' = \underset{(l=1, q=2)}{CH_3COO-Z'-OR_2} \text{ with } -\!\!\left(\!\!\bigcirc\!\!\right)_{\!l}\!\!-\!\!(CH_2)_q\!-\!\!\overset{CH_3}{\underset{*}{CH}}\!\!-$$

| Preparation Example (Starting Material) | Alkylating agent (IX) | | Optically active acetopehenone derivative (XXII) | | | Optically active carboxylic acid compound (III) | | $CH_3COO-Z'-OR_2$ | | Optically active phenols (V) (wherein s = 0) | |
|---|---|---|---|---|---|---|---|---|---|---|---|
| | Name | Amount used | $R_2$ | Yield (g) & Yield (%) | $[\alpha]_D^{20}$ (c = 1, CHCl$_3$) | Yield (g) & Yield (%) | $[\alpha]_D^{20}$ (c = 1, CHCl$_3$) | Yield (g) & Yield (%) | $[\alpha]_D^{20}$ (c = 1, CHCl$_3$) | Yield (g) & Yield (%) | $[\alpha]_D^{20}$ (c = 1, CHCl$_3$) |
| 39 | 2(S)-fluoro-heptyl para-toluene sulfonate | 11.5 g (40 mM) | $\underset{(S)}{-CH_2\overset{F}{\underset{|}{CH}}C_5H_{11}}$ | 6.66 g (54%) | +8.5° | 1.83 g (91%) | +8.9° | 2.02 g (96%) | +9.4° | 1.54 g (89%) | +11.5° |
| 40 | 2(S)-methyl butyl para-toluene sulfonate | 9.7 g (40 mM) | $\underset{(S)}{-CH_2\overset{CH_3}{\underset{|}{CH}}C_2H_5}$ | 6.09 g (58%) | +12.1° | 1.85 g (92%) | +11.9° | 2.01 g (95%) | +12.0° | 1.68 g (99%) | +12.2° |

PREPARATION EXAMPLE (STARTING MATERIAL COMPOUND (III) OR (V)) 41

Except of using 136 g (1.0 mol) of 1-phenyl-2-propanol in place of 4-phenyl-2-butanol (1.0 mol), reaction was conducted, according to Preparation Example (starting material) 36, using the same mol numbers and volumes of reagents and solvents to obtain the results in Table-(xii).

PREPARATION EXAMPLE (STARTING MATERIAL COMPOUND (III) OR (V)) 42

Except of using 164 g (1.0 mol) of 5-phenyl-2-pentanol in place of 4-phenyl-2-butanol (1.0 mol), reaction was conducted, according to Preparation Example (starting material) 36, using the same mol numbers and volumes of reagents and solvents to obtain the results in Table-(xii).

PREPARATION EXAMPLE (STARTING MATERIAL COMPOUND (V)) 43

Into a four-necked flask provided with a stirrer and a thermometer, 25.4 g of (−)-4-acetyl-4'-(2-hydroxypropyl)biphenyl (XXIII-43) [0.1 mol, $[\alpha]_D^{20}=-11.2°$ (C=1, CHCl$_3$)], 69.5 g (0.3 mol) of silver oxide and 255 g (1.5 mol) of propyl iodide were charged, and then stirred at room temperature for 15 days. Thereafter, the reaction mixture was diluted with 300 ml of chloroform, and silver salt was filtered off, and thereafter, the filtrate was concentrated under a reduced pressure. The resulting residue was subjected to a silica gel column chromatography (elution medium: toluene/ethyl acetate=10/1) to obtain 9.0 g of (−)-4-acetyl-4'-(2-propoxypropyl)biphenyl (XXII-43) [yield=30.5%, $[\alpha]_D^{20}=-10.2°$ (C=1, CHCl$_3$), m.p.=53°–55° C.] and 17.4 g of the starting material (XXIII-43) with recovery of 68.5%.

TABLE (xii)

$$Z' = -\!\!\left(\!\!\bigcirc\!\!\right)\!\!-\!\!(CH_2)_q\!-\!\!\overset{CH_3}{\underset{*}{CH}}\!\!-$$

| Preparation Example (Starting Material) | Alkylating agent (IX) | | Optically active acetophenone derivative (XXII) | | | | Optically active carboxylic acid (III) (wherein s = 0) | | | $CH_3COO-\!\!\left(\!\bigcirc\!\right)\!-\!(CH_2)_q\!-\!\overset{CH_3}{\underset{*}{CH}}\!-OR_2$ | | | Optically active phenols (V) (wherein s = 0) | |
|---|---|---|---|---|---|---|---|---|---|---|---|---|---|---|
| | Name | Amount used | $R_2$ | q | Yield (g) & Yield (%) | $[\alpha]_D^{20}$ (c = 1, CHCl$_3$) | q | Yield (g) & Yield (%) | $[\alpha]_D^{20}$ (c = 1, CHCl$_3$) | Yield (g) & Yield (%) | $[\alpha]_D^{20}$ (c = 1, CHCl$_3$) | q | Yield (g) & Yield (%) | $[\alpha]_D^{20}$ (c = 1, CHCl$_3$) |
| 41 | Pentyl iodide | 17.8 g (90 mM) | n-C$_5$H$_{11}$ | 1 | 5.22 g (70%) | −14.4° | 1 | 1.92 g (95%) | −14.4° | 2.02 g (95%) | −13.8° | 1 | 1.67 g (99%) | −15.5° |
| 42 | Pentyl iodide | 17.8 g (90 mM) | " | 3 | 5.39 g (65%) | −4.5° | 3 | 1.97 g (98%) | −4.4° | 2.01 g (95%) | −4.8° | 3 | 1.70 g (99%) | −5.8° |

3.0 g (10 mM) of the thus-obtained compound (XXII-43) was dissolved in 50 ml of anhydrous dichloromethane, and then added with 2.1 g (12 mM) of m-chloroperbenzoic acid and stirred at room temperature for 24 hrs. After completion of the reaction, 10% sodium hydrogen sulfite aqueous solution was added to the reaction mixture to decompose excess m-chloroperbenzoic acid. An organic layer obtained was washed with 10% sodium bicarbonate aqueous solution and water in the order. The resulting organic layer was concentrated in vacuo to obtain 2.9 g of (−)-4-acetoxy-4'-(2-propoxypropyl)biphenyl with yield of 94%.

$[[\alpha]_D^{20}=-9.3°$ (C=1, CHCl$_3$), $n_D^{20}=1.5505]$.

Then, 2.5 g (8 mM) of the thus-obtained (−)-4-acetoxy-4'-(2-propoxypropyl)biphenyl was dissolved in 30 ml of methanol, added with 20% NaOH aqueous solution, and sturred at room temperature for 2 hrs. After completion of the reaction, the reaction solution was added with 1N hydrochloric acid till pH 2–3, and then further added with 100 ml of ethyl acetate to subject extraction treatment. The resulting organic layer was water-washed and then concentrated under a reduced pressure to obtain 2.2 g of (−)-4-hydroxy-4'-(2-propoxypropyl)biphenyl (V-43) with 100% yield.

$[[\alpha]_D^{20}=-8.8°$ (C=1, CHCl$_3$), m.p. 52°–54° C.].

PREPARATION EXAMPLES (STARTING MATERIAL COMPOUND (V)) 44–46

Except of using alkylating agent (IX) shown in Table-(xiii), alkylation, Baeyer-Villiger oxidation, hydrolysis reaction and after-treatment were conducted in the same manner as in Preparation Example (starting material) 43. The results were obtained as shown in Table-(xiii).

chloroform, silver salt was filtered off, and then concentrated under a reduced pressure. The resulting residue was subjected to a silica gel column chromatography (elution medium: toluene/ethylacetate=10/1) to obtain 10.2 g of (−)-4-acetyl-4'-(3-propoxybutyl)biphenyl (XXII-47) with yield of 33.1% $[[\alpha]_D^{20}=-6.8°$ (C=1, CHCl$_3$), $n_D^{20}=1.5380]$, and 17.7 g of starting material (XXIII-47) with recovery of 66.0%.

3.1 g (10 mM) of the thus-obtained compound (XXII-47) was dissolved in 50 ml of anhydrous dichloromethane, added thereto with 2.1 g (12 mM) of m-chloroperbenzoic acid and then stirred for 12 hrs. under a reflux condition. After completion of the reaction, 10% sodium hydrogen sulfite aqueous solution was added to the reaction mixture to decompose excess m-chloroperbenzoic acid, and thereafter an organic layer was washed with 10% sodium bicarbonate aqueous solution and water in the order. The organic layer was concentrated under a reduced pressure to obtain 3.2 g of (−)-4-acetoxy-4'-(3-propoxybutyl)biphenyl with yield of 99%

$[[\alpha]_D^{20}=-4.8°$ (C=1, CHCl$_3$)], $n_D^{20}=1.5478]$.

2.6 g (8 mM) of the thus-obtained (−)-4-acetoxy-4'-(3-propoxybutyl)biphenyl was dissolved in 50 ml of methanol, added thereto with 10 ml of 20% NaOH aqueous solution, and then stirred at room temperature for 2 hrs. After completion of the reaction, the reaction mixture was made to pH 2–3 by adding 1N hydrochloric acid, and then further added thereto with 100 ml of ethyl acetate, and thereafter subjected to extraction treatment. The resulting organic layer was water-washed, and then concentrated under a reduced pressure to obtain 2.3 g of 4-hydroxy-4'-(3-propoxybutyl)biphenyl (V-47) with 100% yield $[[\alpha]_D^{20}=-9.4°$ (C=1, CHCl$_3$), $n_D^{20}=1.3462$.

TABLE (xiii)

$CH_3COO-Z'-OR_2$ wherein $Z' = $ —⟨C$_6$H$_4$⟩—⟨C$_6$H$_4$⟩—CH$_2$—*CH(CH$_3$)—

| Preparation Example (Starting Material) | Alkylating agent R$_2$—O (IX) Name | Amount used (mol number) | Optically active acetophenone derivative (XXII) Yield · g (%) | $[\alpha]_D^{20}$ (c = 1, CHCl$_3$) | Yield · g (%) | $[\alpha]_D^{20}$ (c = 1, CHCl$_3$) | Optically active phenols (V) (wherein s = 0) Yield · g (%) | $[\alpha]_D^{20}$ (c = 1, CHCl$_3$) |
|---|---|---|---|---|---|---|---|---|
| 44 | Pentyl iodide | 297 g (1.5) | 9.4 g (29%) | −11.0° | 3.3 g (98%) | −10.5° | 2.4 g (99%) | −8.2° |
| 45 | Octyl iodide | 240 g (1.0) | 10.7 g (28%) | −9.6° | 3.7 g (97%) | −9.0° | 2.7 g (99%) | −7.3° |
| 46 | Hexadecyl iodide | 282 g (0.8) | 12.9 g (27%) | −5.8° | 4.9 g (99%) | −5.2° | 3.5 g (97%) | −4.1° |

PREPARATION EXAMPLE (STARTING MATERIAL COMPOUND (V)) 47

Into a four-necked flask provided with a thermometer and a stirrer, 26.8 g (0.1 mol) of (−)-4-acetyl-4'-(3-hydroxybutyl)biphenyl (XXIII-47) $[[\alpha]_D^{20}=-11.2°$ (C=1, CHCl$_3$)], 69.5 g (0.3 mol) of silver oxide and 255 g (1.5 mol) of propyl iodide were charged and stirred at room temperature for 10 days. The reaction mixture was dilutred with 300 ml of

PREPARATION EXAMPLES (STARTING MATERIAL COMPOUND (V)) 48–50

Except of using the alkylating agent (IX) shown in Table-(xiv), alkylation, Baeyer-Villiger oxidation, hydrolysis reaction and after-treatment were conducted in the same procedures as in Preparation Example (starting material) 47. The results shown in Table-(xiv) were obtained.

TABLE (xiv)

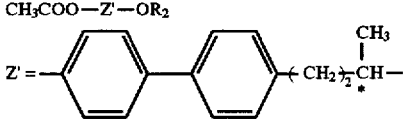

| Preparation Example (Starting Material) | Alkylating agent $R_2-Q$ (IX) Name | Amount used (mol number) | Yield · g (%) | $[\alpha]_D^{20}$ (c = 1, CHCl$_3$) | Yield · g (%) | $[\alpha]_D^{20}$ (c = 1, CHCl$_3$) | Yield · g (%) | $[\alpha]_D^{20}$ (c = 1, CHCl$_3$) |
|---|---|---|---|---|---|---|---|---|
| 48 | Pentyl iodide | 297 g (1.5) | 11.0 g (33%) | −3.8° | 3.5 g (98%) | −3.2° | 2.5 g (99%) | −6.4° |
| 49 | Octyl iodide | 240 g (1.0) | 11.7 g (31%) | −2.6° | 3.9 g (99%) | −2.2° | 2.8 g (100%) | −3.2° |
| 50 | Hexadecyl iodide | 282 g (0.8) | 14.2 g (29%) | −1.8° | 4.9 g (97%) | −1.5° | 3.7 g (99%) | −2.0° |

PREPARATION EXAMPLE (STARTING MATERIAL COMPOUND (V)) 51

Except of using 28.2 g (0.1 mol) of (−)-4-acetyl-4'-(4-hydroxypentyl)biphenyl in place of (−)-4-acetyl-4'-(3-hydroxybutyl)biphenyl, alkylation, Baeyer-Villiger oxidation, hydrolysis reaction and after-treatment were conducted in similar manner to those in Preparation Example (starting material) 47 to obtain the results shown in Table-(xv).

PREPARATION EXAMPLE (STARTING MATERIAL COMPOUND (XXII)) 52

Into a four-necked flask provided with a thermometer and a stirrer, 13.4 g (50 mM) of (−)-4-acetyl-4'-(3-hydroxybutyl) biphenyl (XXIII-52) was charged, and then added thereto with 50 ml of dimethylformamide to allow it to dissolve. After cooling the resulting solution to 0°–5° C., 2.4 g (60 mM) of 60% sodium hydride was added thereto, which was followed by stirring at the same temperature for 1 hr. Thereafter, 13.8 g (60 mM) of n-propyl paratoluenesulfonate was added thereto and stirred at room temperature for 2 hrs. After completion of the reaction, the reaction mixture was poured into 200 ml of water, and then 200 ml of toluene was added to subject extraction treatment. The resulting organic layer was water-washed and dried with anhydrous magnesium sulfate, and thereafter concentrated under a reduced pressure. The resulting residue was subjected to a silica gel column chromatography to obtain (−)-4-acetyl-4'-(3-propoxybutyl)biphenyl (XXII-52) with yields in g and % which are shown in Table-(xvi).

TABLE (xv)

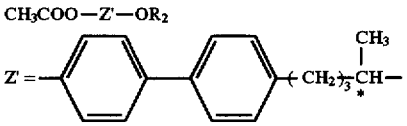

| Preparation Example (Starting Material) | Alkylating agent $R_2-Q$ (IX) Name | Amount used (mol number) | Yield · g (%) | $[\alpha]_D^{20}$ (c = 1, CHCl$_3$) | Yield · g (%) | $[\alpha]_D^{20}$ (c = 1, CHCl$_3$) | Yield · g (%) | $[\alpha]_D^{20}$ (c = 1, CHCl$_3$) |
|---|---|---|---|---|---|---|---|---|
| 51 | Propyl iodide | 255 g (1.5) | 13.2 g (41%) | −3.5° | 3.3 g (97%) | −3.2° | 2.4 g (99%) | −4.4° |

PREPARATION EXAMPLE (STARTING MATERIAL COMPOUND (XXII)) 53

Except of using, as alkylating agent (IX), n-pentyl p-toluenesulfonate in place of n-propyl para-toluenesulfonic acid, alkylation reaction and after-treatment were conducted in similar manner to those in Preparation example (starting material compound (XXII)) 52. The results obtained are shown in Table-(xvi).

TABLE (xvi)

Optically active acetophenone derivative
CH₃CO—Z'—OR₂  (XXII)

Alkylating agent R₂—Q (IX)

$Z' = $ —⟨biphenyl⟩—(CH₂)₂—CH(CH₃)— *

| Preparation Example (Material compound) | Name | Amount used (mol number) | Yield · g (%) | $[\alpha]_D^{20}$ (c = 1, CHCl₃) |
|---|---|---|---|---|
| 52 | n-propyl p-toluene-sulfonate | 13.8 g (60) | 9.6 g (62.5%) | −6.8° |
| 53 | n-pentyl p-toluene-sulfonate | (60) | 10.3 g (60.8%) | −3.8° |

PREPARATION EXAMPLE (STARTING MATERIAL COMPOUND (III)) 54

A solution of 2.0 g (6.4 mM) of (−)-4-acetyl-4'-(3-propoxybutyl)biphenyl (XXII-47) obtained in Preparation Example (starting material) 47 in 80 ml of dioxane was added to an aqueous solution of sodium hypobromite prepared from 80 ml of 20% NaOH aqueous solution and 8.2 g (51.5 mM) of bromine, and then the mixture was stirred at room temperature for 8 hrs. After 4.0 g of sodium hydrogen sulfite was added to the resulting reaction mixture and stirred for 30 mins., the mixture was adjusted to pH 1–2 by adding hydrochloric acid. This mixture was extracted with 100 ml of ether to obtain an organic layer, which was then washed with saturated NaCl solution followed by drying with anhydrous magnesium sulfate. From the resulting organic layer, a solvent was distilled off under a reduced pressure to obtain 1.9 g of (−)-4-carboxy-(3-propoxybutyl)biphenyl (III-54) with yield of 94%.

$[[\alpha]_D^{20} = -14.0° (C=1, CH_3OH)]$.

PREPARATION EXAMPLES (STARTING MATERIAL COMPOUND (III)) 55–57

Except of using the optically active acetophenone derivative (XXII) described in Table-(xiv) in place of (−)-4-acetyl-4'-(3-propoxybutyl)biphenyl (XXII-47), reaction and after-treatment were conducted in the similar manner to those in Preparation Example (starting material) 54 to obtain the results in Table-(xvii).

TABLE (xvii)

| Preparation Example (Starting Material) | Substituent R₂ | Amount used (mol number) | Yield · g (%) | $[\alpha]_D^{20}$ (c = 1, CH₃OH) |
|---|---|---|---|---|
| 55 | n-C₅H₁₁ | 2.2 g (6.4) | 2.1 g (95%) | −12.7° |
| 56 | n-C₈H₁₇ | 2.4 g (6.4) | 2.3 g (93%) | −11.2° |
| 57 | n-C₁₆H₃₃ | 3.2 g (6.4) | 2.9 g (92%) | −8.9° |

Optically active acetophenone derivative (XXII): CH₃CO—Z'—OR₂
Optically active carboxylic acid compound: HOOC—Z'—OR₂ (III)

PREPARATION EXAMPLE (STARTING MATERIAL COMPOUND (III)) 58 & 59

Oxidation reaction and after-treatment were conducted according to Preparation Example (starting material) 54, except of using (−)-4-acetyl-4'-(2-propoxypropyl)biphenyl (XXII-43) obtained in Preparation Example (starting material) 43 or (−)-4-acetyl-4'-(4-propoxypentyl)biphenyl (XXII-51), in place of (−)-4-acetyl-4'-(3-propoxybutyl) biphenyl (XXII-47). The results obtained are shown in Table-(xviii).

TABLE (xvii)

| | Optically active acetophenone derivative (XXII) CH₃CO—Z'—OR₂ | | | Optically active carboxylic acid compound HOOC—Z'—OR₂ (III) | | |
|---|---|---|---|---|---|---|
| | $Z' = $ —〈benzene〉—〈benzene〉—(CH₂)_q—*CH(CH₃)— | | | $Z' = $ —〈benzene〉—〈benzene〉—(CH₂)_q—*CH(CH₃)— | | |
| Preparation Example (Starting Material) | Substituent R₂ | q | Amount used (mol number) | Yield · g (%) | q | [α]_D^{20} (c = 1, CH₃OH) |
| 58 | n-C₃H₇ | 1 | 1.9 g (6.4) | 1.9 g (99%) | 1 | −11.6° |
| 59 | n-C₃H₇ | 3 | 2.1 g (6.4) | 2.1 g (99%) | 3 | −4.9° |

PREPARATION EXAMPLE (STARTING MATERIAL COMPOUND (III) OR (V)) 60

Into a four-necked flask provided with a stirring means and a thermometer, 150 g (1 mol) of (+)-3-phenyl-1-butanol (XXVI-60), 500 ml of toluene and 200 ml of pyridine were charged, and 122.4 g (1.2 mol) of acetic acid anhydride and 1 g of 4-dimethylaminopyridine were further added thereto. The mixture was reacted for 4 hours while temperature being maintained at 40°–50° C. After completion of the reaction, the reaction mixture was poured into 500 ml of 4N hydrochloric acid, extracted and fractionated. The resulting organic layer was washed with 1N hydrochloric acid, water, 5% sodium bicarbonate aqueous solution ad water in the order. The thus-obtained organic layer was concentrated under a reduced pressure to obtain 190 g of (+)-1-acetoxy-3-phenylbutane (XXV-60) with yield of 99.0%.

Next, 240 g (1.8 mol) of aluminium chloride and 141 g (1.8 mol) of acetyl chloride were added to 800 ml of anhydrous dichloroethane, and stirred for about 1 hr. until almost all of the aluminum chloride was dissolved. After that, the resulting solution was cooled to 0°–5° C., and then a solution of 173 g (0.9 mol) of the above obtained compound (XXV-60) in 200 ml of dichloroethane was dropwise added to the cooled solution, while the same temperature being maintained. After completion of the dropwise addition, the reaction mixture was stirred at the same temperature for 2 hrs., and then pour into 1 l of water, extracted and fractionated. The resulting organic layer was washed with water, 5% sodium bicarbonate aqueous solution and water in the order, and then a solvent was distilled off therefrom to obtain a yellow oily substance, which was further distilled in vacuo to obtain 145.5 g of (+)-4-(1-methyl-3-acetoxypropyl)acetophenone (XXIV-60) with yield of 69% (b.p. 130° C./0.3 mm Hg).

100 g of the thus-obtained compound (XXIV-60) was dissolved in a mixed solvent of 300 ml of methanol and 100 ml of tetrahydrofuran, 150 ml of 20% NaOH aqueous solution was added thereto, and then the mixture was stirred for 10 hrs. After completion of the reaction, the reaction solution was adjusted to pH 8 with hydrochloric acid, and then 300 ml of ether and 300 ml of water were further added thereto. The resulting solution was extracted and fractionated to obtain an organic layer, which was dried with anhydrous magnesium sulfate and thereafter a solvent was distilled off under a reduced pressure. Thus, 80.4 g of (+)-4-(1-methyl-3-hydroxypropyl)acetophenone (XXIII-60) were obtained with yield of 98% [[α]_D^{20}=+28.5° (C=1, CHCl₃), n=1.5366].

To 5.77 g (30 mM) of the resulting compound (XXIII-60), 15.3 g of propyl iodide and 13.9 g of silver oxide were added, and then the mixture was stirred at room temperature under a shade for 4 days. After completion of the reaction, silver salt was filtered off and the filterate was concentrated in vacuo to obtain a residue. This was separated by a silica gel column chromatography (elution medium: toluene-ethyl acetate) to obtain 4.47 g of (+)-4-(1-methyl-3-propoxypropyl)acetophenone (XXII-60) with yield of 63.6%

[[α]_D^{20}=+32.9° (C=1, CHCl₃), n_D^{20}=1.5046].

2.0 g of the resulting (+)-4-(1-methyl-3-propoxyproyl)acetophenone (XXII-60) as well as 100 ml of dioxane were added to sodium hypobromite aqueous solution prepared from 100 ml of 20% NaOH aqueous solution and 10.9 g (68.3 mM) of bromine. After stirring at room temperature for a day, the reaction mixture was added with 20 g of sodium sulfite and stirred, and thereafter adjusted with hydrochloric acid to pH 1–2, which was followed by extraction with 200 ml ether. The resulting organic layer was washed with saturated NaCl aqueous solution, and then dried with anhydrous magnesium sulfate. From the thus-treated organic layer a solvent was distilled off under a reduced pressure to obtain 1.89 g of (+)-4-(1-methyl-3-propoxypropyl)benzoic acid with yield of 93%

[[α]_D^{20}=+31.6° (C=1, CHCl₃)].

Further, 2.0 g of the compound (XXII-60) was dissolved in 20 ml of dichloromethane, and 1.77 g (1.2 equivalent) of m-chloroperbenzoic acid was added thereto, which was followed by stirring at room temperature for 24 hrs. After completion of the reaction, the resulting precipitate was filtered off, and then 100 ml of toluene was added to the filtrate to obtain an organic layer, which was then washed with water, 5% NaOH aqueous solution and water in the order, and thereafter dried with anhydrous magnesium sulfate. From the thus-treated organic layer, a solvent was distilled off under a reduced pressure to obtain 2.03 g of (+)-4-(1-methyl-3-propoxypropyl)acetoxybenzene with yield of 95%

[[α]_D^{20}=+31.8° (C=1, CHCl₃)].

2.0 g of the (+)-4-(1-methyl-3-propoxypropyl)acetoxybenzene was added to a mixed solution of 20 ml of methanol, 10 ml of THF and 10 ml of 20% NaOH aqueous solution,.and then the mixture was stirred at room temperature for 6 hrs.

After completion of the reaction, the reaction solution was adjusted with hydrochloric acid to pH 2–3, which was then followed by extraction and fractionation with 100 ml of ether. The resulting organic layer was washed with saturated NaCl aqueous solution, and then a solvent was distilled off therefrom under a reduced pressure to obtain 1.66 g of (+)-4-(1-methyl-3-propoxypropyl)phenyl (V-60) with 100% yield

[[α]_D^{20}=+31.1° (C=1, CHCl₃)].

PREPARATION EXAMPLES (STARTING MATERIAL COMPOUND (III) OR (V)) 61-63

Except of using 5.77 g (30 mM) of the compound (XXIII-60) obtained in Preparation Example (starting material) 60 and the alkylating agents shown in Table-(xix), reaction and after-treatment were conducted in the same way as in said Preparation Example 60. The results as shown in Table-(xix) were obtained.

magnesium sulfate. The organic layer was concentrated under a reduced pressure, and then resulting residue was separated and purified by a silica gel column chromatography (elution medium: toluene-ethyl acetate) to obtain 6.76 g of (+)-4-{1-methyl-3-(2-fluoroheptyl)oxypropyl}acetophenone (XXII-64) with yield of 54.8%.

Using the thus-obtained compound (XXII-64), reaction and after-treatment were conducted in the similar manner to

TABLE (xix)

$$Z' = \left(\bigcirc\right)_l - \underset{*}{CH} \underset{|}{\overset{CH_3}{|}} (CH_2)_{\overline{t}} \quad (l=1, t=2)$$

$s = 0$

| Preparation Example (Starting Material) | Alkylating agent $R_2-Q$ (IX) Name | Amount used (mM) | Optically active** acetophenone derivative (XXII) Yield g (%) ① | $[\alpha]_D^{20}$ (c = 1, CHCl$_3$) $n_D^{20}$ | Optically active** acyloxybenzene (XVIII) Yield g (%) ② | $[\alpha]_D^{20}$ (c = 1, CHCl$_3$) | Optically active** carboxylic acid compound (III) Yield g (%) ③ | $[\alpha]_D^{20}$ (c = 1, CHCl$_3$) $n_D^{20}$ | Optically active** phenols (V) Yield g (%) ④ | $[\alpha]_D^{20}$ (c = 1, CHCl$_3$) |
|---|---|---|---|---|---|---|---|---|---|---|
| 61 | n-pentyl iodide | 17.8 g (90) | 4.96 g (63%) | +32.7° 1.5040 | 2.07 g (97%) | +30.8° | 1.93 g (96%) | +31.0° | 1.65 g (98%) | +30.4° |
| 62 | n-octyl iodide | 21.6 g (90) | 5.31 g (58%) | +29.1° 1.4971 | 2.01 g (96%) | +27.3° | 1.94 g (96%) | +27.0° | 1.69 g (98%) | +26.9° |
| 63 | n-hexadecyl iodide | 31.7 g (90) | 6.28 g (50%) | +21.8° 1.4901 | 2.01 g (97%) | +20.9° | 1.95 g 97% | +20.8° | 1.69 g (94%) | +22.1° |

**p = 2① Yield (%) of alkylation reaction, ② Yield (%) of Baeyer-villiger oxidation reaction, ③ Yield (%) of oxidation reaction, ④ Yield (%) of hydrolysis reaction.

PREPARATION EXAMPLE (STARTING MATERIAL COMPOUND (III) OR (V)) 64

7.7 g (40 mM) of (+)-4-(1-methyl-3-hydroxypropyl)acetophenone (XXIII-60) obtained in Preparation Example (starting material) 60 was dissolved in 40 ml of dimethylformamide, and 3.2 g (80 mm) of 60% sodium hydride was added thereto and then the mixture was stirred for a hour. Thereafter, 11.5 g (40 mM) of 2(S)-fluoroheptyl p-toluenesulfonate was added thereto. After reaction was conducted as such for 2 hrs, the reaction solution was poured into 200 ml of water, 200 ml of toluene was further added thereto to extract and fractionate, and thereafter, an organic layer was washed with water and then dried with anhydrous magnesium sulfate.

those in Preparation Example (starting material) 60 to obtain the results shown in Table-(xx).

PREPARATION EXAMPLE (STARTING MATERIAL COMPOUND (III) OR (V)) 65

Except of using 9.7 g (40 mM) of 2(S)-methylbutyl paratoluenesulfonate as alkylating agent (IX), reaction and after-treatment were conducted in the similar manner to those in Preparation Example (starting material) 64 to obtain the results shown in Table-(xx).

TABLE (xx)

$$Z' = \left(\bigcirc\right)_l - \underset{*}{CH} \underset{|}{\overset{CH_3}{|}} (CH_2)_{\overline{t}} \quad (l=1, t=2)$$

$s = 0$

| Preparation Example (Starting Material) | Alkylating agent $R_2-Q$ (IX) Name | Amount used (mM) | Optically active acetophenone derivative (XXII) Yield g (%) | $[\alpha]_D^{20}$ (c = 1, CHCl$_3$) $n_D^{20}$ | Optically active acyloxybenzene (XVIII) Yield g (%) | $[\alpha]_D^{20}$ (c = 1, CHCl$_3$) | Optically active carboxylic acid compound (III) Yield g (%) | $[\alpha]_D^{20}$ (c = 1, CHCl$_3$) $n_D^{20}$ | Optically active phenols (V) Yield g (%) | $[\alpha]_D^{20}$ (c = 1, CHCl$_3$) |
|---|---|---|---|---|---|---|---|---|---|---|
| 64 | 2(S)fluoroheptyl p-toluene sulfonate | 11.5 g (40) | 6.16 g (50%) | +32.1° | 2.02 g (96%) | +28.1° | 1.84 g (91%) | +28.9° | 1.55 g (89%) | +27.8° |
| 65 | 2(S)methylbutyl p-toluene sulfonate | 9.7 g (40) | 6.23 g (58%) | +33.0° | 2.02 g (95%) | +31.4° | 1.97 g (98%) | +32.0° | 1.69 g (99%) | +31.4° |

PREPARATION EXAMPLE (STARTING MATERIAL COMPOUND (III) OR (V)) 66

Except of using 136 g (1.0 mol) of (+)-2-phenyl-1-propanol in place of (+)-3-phenyl-1-butanol (1 mol), acylation and acetylation were conducted according to Preparation Example (starting material) 60. Thereafter, according to Preparation Example (starting material) 61, alkylation was conducted to obtain 5.07 g of (+)-4-(1-methyl-2-pentyloxyethyl)acetophenone (XXII-66) with yield of 68%.

$[\alpha]_D^{20}$=+4.5° (C=1, CHCl$_3$), $n_D^{20}$=1.5098.

Further, oxidation reaction was conducted to obtain optically active carboxylic acids (III).

Also, the compound (XXII-66) was subjected to Baeyer-Villiger oxidation followed by hydrolysis to obtain optically active phenols (V). The results are shown in Table-(xxi).

acetylphenyl)-5-decyloxypyrimidine, and while maintaining the temperature at 30° to 35° C., 2.65 g (0.07 mole) of sodium borohydride were gradually added thereto. After stirring at the same temperature for 4 hours, the reaction mixture was poured into 500 ml of water and extracted with 400 ml of ethyl acetate. The organic phase was washed sufficiently, dried over anhydrous magnesium sulfate, and then the solvent was distilled off under reduced pressure to obtain 35.6 g (yield: 99.9 %) of 2-{4-(1-hydroxyethyl)phenyl}-5-decyloxypyrimidine.

To a solution of 32.1 g (0.09 mole) of the thus obtained 2-{4-(1-hydroxyethyl)phenyl}-5-decyloxypyrimidine, 200 ml of toluene and 100 ml of pyridine were added 12.2.g (0.12 mole) of acetic anhydride and 1 g of 4-dimethylaminopyridine, and while maintaining the temperature at 30° to 40° C., reaction was carried out for 6

TABLE (xxi)

$$Z' = -\!\!\left(\!\!\!\begin{array}{c}\\ \end{array}\!\!\!\right)_l\!\!-\!\!\overset{CH_3}{\underset{*}{CH}}\!\!-\!\!(CH_2)_t\!\!-\quad \text{(wherein } l = 1, t = 1)$$

(wherein s = 0)

| Preparation Example (Starting Material) | Alkylating agent $R_2 - Q$ (IX) Name | Amount used (mM) | Optically active acetophenone derivative (XXII) Yield g (%) | $[\alpha]_D^{20}$ (c = 1, CHCl$_3$) $n_D^{20}$ | Optically active acyloxybenzene (XVIII) Yield g (%) | $[\alpha]_D^{20}$ (c = 1, CHCl$_3$) | Optically active carboxylic acid compound (III) Yield g (%) | $[\alpha]_D^{20}$ (c = 1, CHCl$_3$) $n_D^{20}$ | Optically active phenols (V) Yield g (%) | $[\alpha]_D^{20}$ (c = 1, CHCl$_3$) |
|---|---|---|---|---|---|---|---|---|---|---|
| 66 | n-pentyl iodide | 17.8 g (90) | 5.07 g (68%) | +4.5° 1.5098 | 2.01 g (95%) | +2.5° | 1.98 g (98%) | +2.0° | 1.70 g (99%) | +3.5° |

PREPARATION EXAMPLES (STARTING MATERIAL COMPOUND (III) 67–69

Except of using (+)-3-(4-biphenylyl)-1-butanol (XXVI-67), (+)-2-(4-biphenylyl)-1-propanol (XXVI-68) and (+)-4-(4-biphenylyl-1-pentanol (XXVI-69), respectively place of (+)-3-phenyl-1-butanol (XXVI-60), acylation, Friedel-Crafts reaction, hydrolysis, alkylation, oxidation and after-treatment were conducted in the similar manner to those in Preparation Example (starting material) 60 to obtain the results shown in Table-(xxii).

hours. After completion of the reaction, the reaction mixture was poured into 500 ml of water, adjusted the pH to 1 to 2 with 4N hydrochloric acid and then 200 ml of toluene were added to effect extraction and separation. The resulting organic phase was washed with water, 5% aqueous sodium hydrogen carbonate and water in this order and finally dried over anhydrous magnesium sulfate.

The solvent was distilled off under reduced pressure to obtain 35.5 g (yield: 99%) of 2-{4-(1-acetoxyethyl)phenyl}-5-decyloxypyrimidine.

TABLE (xxii)

| Preparation Example (Starting Material) | l | Z' | t | s | $R_2$ | $[\alpha]_D^{20}$ (c = 1, CHCl$_3$) |
|---|---|---|---|---|---|---|
| 67 | 2 | ![structure with CH$_3$, CH-(CH$_2$)$_t$, l] | 2 | 0 | n-C$_3$H$_7$ | +3.2° |
| 68 | 2 | " | 1 | 0 | n-C$_{12}$H$_{25}$ | +2.4° |
| 69 | 2 | " | 3 | 0 | -(CH$_2$)$_3$OC$_2$H$_5$ | +2.7° |

PREPARATION EXAMPLE (STARTING-MATERIAL COMPOUND (VI)) 70

To a mixed solvent of 200 ml of ethanol and 100 ml of chloroform were added 35.5 g (0.1 mole) of 2-(4-

31.9 g (0.08 mole) of the above 2-{4-(1-acetoxyethyl)phenyl}-5-decyloxypyrimidine were suspended in 450 ml of a 0.3M phosphate buffer (pH 7.0) and 10 ml of chloroform and 1.6 g of lipase ([Amano P]) were added thereto, followed by vigorous stirring at 38°±2° C. for 24 hours.

After completion of the reaction, to the reaction mixture were added 300 ml of ethyl acetate to effect separation of the solution. Then, the organic phase was washed with water and concentrated under reduced pressure and the resulting residue was separated by silica gel column chromatography (eluent; toluene:ethyl acetate).

13.9 g (yield: 48.7%) of (+)-2-{4-(1-hydroxyethyl) phenyl}-5-decyloxypyrimidine, $[\alpha]_D^{20}$=+26.0° (C=1, CHCl$_3$) and 16.1 g (yield: 50.5%) of (−)-2-{4-(1-acetoxyethyl)phenyl}-5-decyloxypyrimidine were obtained.

EXAMPLE 1

Into 20 ml of anhydrous dimethylformamide were dissolved 1.78 g (5 millimole) of the (+)-2-{4-(1-hydroxyethyl) phenyl}-5-decyloxypyrimidine obtained in Preparation Example [starting material compound (VI)] 70, and then 0.24 g (6 millimole) of 60% sodium hydride was added thereto, followed by stirring at 40° C. for 1 hour. Subsequently, 1.79 g (7 millimole) of hexyl p-toluenesulfonate were added thereto, to subject to reaction at the same temperature for 2 hours. After completion of the reaction, the reaction mixture was poured into 200 ml of water, extracted with 200 ml of toluene, followed by separation thereof, and the organic phase was washed with water sufficiently, followed by drying over anhydrous magnesium sulfate. After the solvent was distilled off under reduced pressure, the resulting residue was purified by silica gel column chromatography (eluent; toluene:ethyl acetate) to obtain 1.81 g (yield: 82%) of (+)-2-{4-(1-hexyloxyethyl) phenyl}-5-decyloxypyrimidine.

The physical values are shown in Table 1.

EXAMPLES 2 AND 3

Reaction and post-treatment were carried out in the same manner as in Example 1 except that (+)-2-{4-(1-hydroxyethyl)phenyl}-5-decyloxypyrimidine obtained in Preparation Example [starting material compound (VI)] 70 was used and the reagents as shown in Table-1 as the alkylating agents (IX), to obtain the results as shown in Table-1.

EXAMPLE 4

Into 20 ml of pyridine were dissolved 1.78 g (5 millimole) of the (+)-2-{4-(1-hydroxyethyl)phenyl}-5-decyloxypyrimidine obtained in the Preparation Example [starting material compound (VI)] 70, and then 0.56 g (6 millimole) of propionic chloride was added thereto, to subject to reaction at 30° to 40° C. for 2 hours. After completion of the reaction, the reaction mixture was poured into 200 ml of water, adjusted to pH 1 to 2 with 4N hydrochloric acid, and then extracted with 200 ml of toluene, followed by separation thereof. The organic phase was washed with water, 5% aqueous sodium hydrogen carbonate solution and water in this order. After drying over anhydrous magnesium sulfate, the residue obtained by distilling the organic solvent off under reduced pressure was purified by silica gel column chromatography (eluent; toluene:ethyl acetate) to obtain 2.00 g (yield: 97%) of (+)-2-{4-(1-Propanoyloxyethyl)phenyl}-5-decyloxypyrimidine.

The physical values are shown in Table-1.

EXAMPLE 5

Reaction and post-treatment were carried out in the same manner as in Example 4 except that the alkylating agent (IX) was placed with 0.81 g (6 millimoles) of hexanoyl chloride to obtain the results as shown in Table-1.

EXAMPLE 6

Into 20 ml of dichloromethane were dissolved 1.78 g (5 millimoles) of the (+)-2-{4-(1-hydroxyethyl)phenyl}-5-decyloxypyrimidine obtained in Preparation Example [starting material compound (VI)] 70 and 1.2 g (6 millimoles) of dodecanic acid, and then 1.4 g of N,N'-dicyclohexylcarbodiimide and 0.1 g of 4-pyrrolidinopyridine were added thereto, followed by stirring at room temperature for 24 hours. After completion of the reaction, the precipitates were filtered off and 200 ml of toluene were added thereto, followed by washing with water, 5% acetic acid, water, 5% aqueous sodium hydrogen carbonate solution and water in this order. After the organic phase was dried over anhydrous magnesium sulfate, the solvent was distilled off under reduced pressure. The resulting residue was purified by silica gel column chromatography (eluent; toluene:ethyl acetate) to obtain 2.53 g (yield: 94%) of (+)-2-{4-(1-dodecanoyloxyethyl)phenyl}-5-decyloxypyrimidine. The physical values are shown in Table-1.

EXAMPLE 7

Into 100 ml of methanol and 50 ml of tetrahydrofuran were dissolved 15 g of the (−)-2-{4-(1-acetoxyethyl) phenyl}-5-decyloxypyrimidine obtained in Preparation Example [starting material compound (VI)] 70, and then 50 ml of 20% aqueous sodium hydroxide solution were added thereto, to subject to reaction at 40° to 45° C. for 4 hours. After completion of the reaction, 4N hydrochloric acid was added to the reaction mixture to adjust it to pH 7 to 8, and then 200 ml of toluene were added to effect extraction and separation. After the organic phase was washed with water, the solvent was distilled off under reduced pressure to obtain 13.2 g (yield: 98.5%) of (−)-2-{4-(1-hydroxyethyl)phenyl}-5-decyloxypyrimidine.

Reaction and post-treatment were carried out in the same manner as in Example 6 except that 1.78 g (5 millimoles) of the (−)-2-{4-(1-hydroxyethyl)phenyl}-5-decyloxypyrimidine obtained above were used and those as shown in Tabla-1 were used as the acylating agents to obtain the results as shown in Table-1.

EXAMPLES 8 AND 9

Reaction and post-treatment were carried out in the same manner as in Example 1 except that 1.78 g (5 millimoles) of the (−)-2-{4-(1-hydroxyethyl)pheny}-5-decyloxypyrimidine obtained in Example 7 were used and the reagents as shown in Table-1 were used as the acylating agent to obtain the results as shown in Table-1.

EXAMPLES 10 TO 22

Reaction and post-treatment were carried out in the same manner as in Example 1 for the Examples 10, 11, 12, 14, 15, 16, 17, 19, 20, 21 and 22 and in the same manner as in Example 4 for the Examples 13 and 18, respectively, except that the optically active aromatic alcohols (VI) were used as the starting-material and the reagents as shown in Table-1 were used to obtain the results as shown in Table-1.

EXAMPLES 23 to 25

Liquid crystal compositions as shown in Table-2 were formulated by using optically active benzene derivative (I).

Formulation was carried out by weighing predetermined amounts of predetermined compounds and mixing them in a sample bottle under heating and melting.

[Preparation Method of Liquid Crystal Element]

On a glass substrate Provided with indium oxide transparent electrodes was provided a polyimide type polymer coating film, followed by rubbing in a predetermined direction by use of gauzes. A liquid crystal cell was assembled by employing glass fibers (diameter: 5 μm) as a spacer so as to maintain the rubbing directions of two pieces of the substrate paralleled and the liquid crystal composition (or liquid crystal compound) described above was charged thereinto and sealed under vacuum to obtain a liquid crystal element.

The liquid crystal element was combined with a polarizer and 20 V was applied to the electric field to observe and measure changes in intensity of transmitted light. As a result, it has been confirmed that the liquid crystal element is capable of functioning as a switching element.

It has been found that, as is apparent from these results, when the optically active benzene derivatives (I-c) and (I-d) of the present invention are used as a liquid crystal material, lowering of the temperature range for the Sc* phase can be performed as compared with the Comparative example, and further a liquid crystal composition having a spontaneous polarization value enough to practical use can be obtained.

TABLE 1

$$Z'' = -CH(CH_3)-CH_2 \overset{*}{\underset{t}{}}$$

| | Optically active aromatic alcohol (VI) | | | | Alkylating agent or | | | | Optically active benzene derivatives (I-c) or (I-d) | | | | | | | Yield | $[\alpha]_D^{20}$ |
|---|---|---|---|---|---|---|---|---|---|---|---|---|---|---|---|---|---|
| Example | $R_1$ | Y | Ar'' | | t | m | acylating agent | | $R_1$ | $R_2$ | Y | Ar'' | t | m | s | (%) | (c = 1, CHCl₃) |
| 1 | n-C₁₀H₂₁ | —O— |  | | 0 | 1 | hexyl p-toluene-sulfonate | | n-C₁₀H₂₁ | n-C₆H₁₃ | —O— |  | 0 | 1 | 0 | 82 | +25.8° |
| 2 | " | " | " | | " | " | octyl p-toluene-sulfonate | | " | n-C₈H₁₇ | " | " | " | " | 0 | 84 | +23.2° |
| 3 | " | " | " | | " | " | hexadecyl p-toluenesulfonate | | " | n-C₁₆H₃₃ | " | " | " | " | 0 | 86 | +19.1° |
| 4 | " | " | " | | " | " | propionyl chloride | | " | n-C₂H₅ | " | " | " | " | 1 | 97 | +71.0° |
| 5 | " | " | " | | " | " | hexanoyl chloride | | " | n-C₅H₁₁ | " | " | " | " | 1 | 97 | +63.4° |
| 6 | " | " | " | | " | " | dodecanoic acid | | " | n-C₁₁H₂₃ | " | " | " | " | 1 | 94 | +54.8° |
| 7 | n-C₁₀H₂₁ | —O— |  | | 0 | 1 | 2(S)-chloro-3(s)-methyl-pentanoic acid 0.89 g | | n-C₁₀H₂₁ | CH₃ Cl<br>  \|    \|<br>C₂H₅CH—CH—<br>(S)  (S) | —O— |  | 0 | 1 | 1 | 89 | −25.2° |
| 8 | " | " | " | | " | " | 2(S)-fluoroheptyl p-toluene-sulfonate 1.73 g | | " | F<br>\|<br>C₅H₁₁CHCH₂—<br>(S) | " | " | " | " | 0 | 79 | −28.2° |
| 9 | " | " | " | | " | " | 2(S)-methylbutyl p-toluene-sulfonate 1.45 g | | " | CH₃<br>\|<br>C₂H₅CH—CH₂—<br>(S) | " | " | " | " | 0 | 88 | −24.1° |
| 10 | n-C₁₆H₃₃ | —O— | " | | 0 | 1 | propyl p-toluene-sulfonate | | n-C₁₆H₃₃ | n-C₃H₇ | —O— | " | " | " | 0 | 88 | +18.1° |
| 11 | n-C₁₀H₂₁ | — | " | | 0 | 0 | " | | n-C₁₀H₂₁ | n-C₃H₇ | " | " | 0 | 0 | 0 | 82 | +22.8° |
| 12 | n-C₁₀H₂₁ | —O— | " | | 2 | 1 | hexyl p-toluene-sulfonate | | n-C₁₀H₂₁ | n-C₆H₁₃ | —O— | " | 2 | 1 | 0 | 85 | +4° |

TABLE 1-continued $$Z'' = -\overset{CH_3}{\underset{*}{CH}}(CH_2)_{\overline{t}}$$

| | Optically active aromatic alcohol (VI) | | | | Alkylating agent or | | | Optically active benzene derivatives (I-c) or (I-d) | | | | | | Yield | $[\alpha]_D^{20}$ |
|---|---|---|---|---|---|---|---|---|---|---|---|---|---|---|---|
| Example | $R_1$ | Y | Ar'' | t | m | acylating agent | $R_1$ | $R_2$ | Y | Ar'' | t | m | s | (%) | (c = 1, CHCl$_3$) |
| 13 | n-C$_{10}$H$_{21}$ | —O— | [pyrimidine-phenyl] | 2 | 1 | hexanoyl chloride | n-C$_{10}$H$_{21}$ | n-C$_5$H$_{11}$ | —O— | [pyrimidine-phenyl] | 2 | 1 | 1 | 98 | +4° |
| 14 | " | " | " | 2 | 1 | hexyl p-toluene-sulfonate | " | n-C$_6$H$_{13}$ | " | " | 2 | 1 | 0 | 90 | +3.5° |
| 15 | " | " | " | 4 | 1 | hexyl p-toluene-sulfonate | " | " | " | " | 4 | 1 | 0 | 99 | +2.0° |
| 16 | " | " | " | 4 | 1 | hexyl p-toluene-sulfonate | " | " | " | " | " | " | " | 86 | +2.0° |
| 17 | " | " | " | 1 | 1 | pentyl p-toluene-sulfonate | " | n-C$_5$H$_{11}$ | " | " | 1 | 1 | 0 | 88 | −3.0° |
| 18 | " | " | " | 1 | 1 | pentanoyl chloride | " | n-C$_4$H$_9$ | " | " | 1 | 1 | 1 | 99 | −3.6° |
| 19 | " | —OCO— | " | 2 | 1 | propyl p-toluene-sulfonate | " | n-C$_3$H$_7$ | —OCO— | " | 2 | 1 | 0 | 84 | +3.2° |
| 20 | n-C$_{10}$H$_{21}$ | —COO— | " | 2 | 1 | pentyl p-toluene-sulfonate | n-C$_{10}$H$_{21}$ | n-C$_5$H$_{11}$ | —COO— | " | 2 | 1 | 0 | 83 | −4.0° |
| 21 | " | —OCO— | [biphenyl] | 3 | 1 | 3-ethoxypropyl p-toluenesulfonate | " | C$_2$H$_5$O(CH$_2$)$_3$ | —OCO— | [biphenyl] | 3 | 1 | 0 | 84 | −1.5° |
| 22 | " | —OCO— | " | 1 | 1 | dodecyl p-toluene sulfonate | " | n-C$_{12}$H$_{25}$ | —OCO— | " | 1 | 1 | 0 | 88 | −1.8° |

TABLE 2

| | Liquid crystalline composition (Value in the parentheses is indicated by % by weight) | Phase transition temperature (°C.) | Spontaneous polarization Ps (nc/cm$^2$) |
|---|---|---|---|
| Comparative example | C$_{10}$H$_{21}$O—⟨O⟩—COO—⟨O⟩—O(CH$_2$)$_3$CHC$_2$H$_5$ with CH$_3$ branch (*)<br>Comparative compound (100) | K ⇄35⇄ Sc* ⇄70⇄ S$_A$ ⇄74⇄ I | 0 |
| Example 23 | Comparative compound (80)<br>Compound in Example 1 (20) | K ⇄⇄ S$_I$ ⇄1⇄ Sc* ⇄39⇄ S$_A$ ⇄50⇄ I | 3 |
| Example 24 | Comparative compound (80)<br>Compound in Example 5 (20) | K ⇄8⇄ Sc* ⇄36⇄ S$_A$ ⇄42⇄ I | 6 |
| Example 25 | Comparative compound (80)<br>Compound in Example 17 (20) | K ⇄⇄ S$_A$ ⇄1⇄ Sc* ⇄40⇄ S$_A$ ⇄43⇄ I | 2 |

S$_I$ shows smetic phase unidentified.

EXAMPLE 26

Into 20 ml of anhydrous dichloromethane were dissolved 1.97 g (6 millimoles) of 2-(4-hydroxyphenyl)-5-decyloxypyrimidine and 1.25 g (5 millimoles) of (−)-4-(2-pentyloxypropyl)benzoic acid, and then 1.22 g (6 millimoles) of N,N'-dicyclohexylcarbodimide and 0.1 g of 4-pyrrolidinoxyridine were added thereto, followed by stirring at room temperature for one day. After completion of the reaction, the precipitates were filtered off and 200 ml of toluene were added thereto, followed by washing with water, 5% acetic acid, water, 5% aqueous sodium hydrogen carbonate solution and water in this order. Then, the organic phase was dried over anhydrous magnesium sulfate. After the solvent was distilled off under reduced pressure, the resulting residue was purified by silica gel column chromatography (eluent; toluene:ethyl acetate) to obtain 2.44 g (yield: 87%) of 4-(5-decyloxy-2-pyrimidyl)phenyl (−)-{4-(2-pentyloxypropyl)benzoate.

EXAMPLE 27

Into 20 ml of pyridine was dissolved 1.80 g (6 millimoles) of 2-(4-hydroxyphenyl)-5-octyloxypyrimidine was dissolved and then 1.41 g (5 millimoles) of an acid chloride derived from (−)-4-(3-pentyloxybutyl)benzoic acid were added thereto, to subject to reaction at 30 to 40° C. for 2 hours. After completion of the reaction, the reaction mixture was poured into 200 ml of water, adjusted to pH 3 to 4 with hydrochlolic acid, followed by extraction with 200 ml of toluene. The organic phase was washed with water, 5% aqueous sodium hydrogen carbonate solution and water in this order and then the organic layer was dried over anhydrous magnesium sulfate. After the solvent was distilled off under reduced pressure, the resulting residue was purified by silica gel column chromatography (eluent; toluene:ethyl acetate) to obtain 2.62 g (yield: 96%) of 4-(5-octyloxy-2-pypymidyl)phenyl (−)-{4-(3-pentyloxybutyl)benzoate.

EXAMPLES 28 TO 49

Reaction and post-treatment were carried out by using the same mole number and the same amount of the solvent as in Example 26 except that the starting material used in Example 26 was placed with those as shown in Table-5, to obtain the results as shown in Table-5.

The phase transition temperature and spontaneous polarization values for representative compounds among those obtained in the above described Examples are shown in Table-3.

TABLE 3

| Example No. | Phase transition temperature | Spontaneous polarization Ps (nc/cm$^2$) |
|---|---|---|
| 26 | K ⇄35⇄ Sc* ⇄60⇄ ch ⇄99.5⇄ I | 20 |
| 31 | K ⇄36⇄ Sc* ⇄86⇄ ch ⇄113⇄ I | 16 |
| 34 | K ⇄92⇄ ch ⇄162⇄ I | — |
| 35 | K ⇄51⇄ S$_I$ ⇄95⇄ ch ⇄126⇄ I | — |
| 39 | K ⇄91⇄ Sc* ⇄126⇄ S$_A$ ⇄138⇄ I | 19 |
| 48 | K ⇄99⇄ Sc* ⇄111⇄ S$_A$ ⇄129⇄ I | 4 |

EXAMPLES 50 TO 52

Liquid crystal compositions as shown in Table-4 were formulated by using the optically active benzene derivatives (I) of the present invention. Formulation was carried out by weighing predetermined amounts of predetermined compounds and mixing them in a sample bottle under heating and melting.

[Preparation Method of Liquid Crystal Element]

On a glass substrate provided with indium oxide trsansparent electrodes was provided a polyimide type polymer coating film, followed by rubbing in a predetermined direction by use of gauzes. A liquid crystal cell was assembled by employing glass fibers (diameter: 5 μm) as a spacer so as to maintain the rubbing directions of two pieces of the substrate paralleled and the liquid crystal composition compound described above was charged thereinto and sealed under vacuum to obtain a liquid crystal element.

The liquid crystal element was combined with a polarizer and 20 V was applied to the electric field to observe and measure changes in intensity of transmitted light. As a result, it has been confirmed that the liquid crystal element is capable of functioning as a switching element.

TABLE 4

| | Liquid crystalline composition (Value in the parentheses is indicated by % by weight) | Spontaneous polarization Ps (nc/cm²) |
|---|---|---|
| Comparative example | 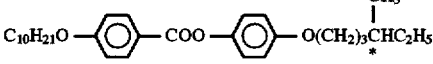 Comparative compound (100) | 0 |
| Example 50 | Comparative compound the above (80) Compound in Example 34 (20) | 4 |
| Example 51 | Comparative compound the above (80) Compound in Example 35 (20) | 5 |
| Example 52 | Comparative compound the above (50) Compound in Example 39 (50) | 12 |

As is apparent from these results, when the optically active benzene derivatives of the present invention are used as the liquid crystal material, irrespectively of said benzene derivatives themselves exhibiting Sc* phase or not, spontaneous polarization value can be increased as compared with the Comparative example in which a comparative compound is used singly, whereby the response speed can be improved.

TABLE 5

$$Z' = -\left(\bigcirc\right)_l + CH_2 \frac{}{q} + \begin{pmatrix} CH_3 \\ | \\ CH \\ * \end{pmatrix}_s$$

| | Phenols (II) | | | | Optically active carboxylic acid compound (III) | | | | | | Optically active benzene derivative (I-a) | |
|---|---|---|---|---|---|---|---|---|---|---|---|---|
| Example | $R_1$ | Ar' | Y | m | $R_2$ | R' | u | l | q | s | X | Yield (%) | $[\alpha]_D^{20}$ (c = 1, CHCl₃) |
| 26 | n-$C_{10}H_{21}$ | ⟨pyrimidinyl-phenyl⟩ | —O— | 1 | n-$C_5H_{11}$ | OH | 1 | 1 | 1 | 0 | —OCO— | 87 | −7.9° |
| 27 | n-$C_8H_{17}$ | " | —O— | 1 | n-$C_{12}H_{25}$ | OH | 1 | 1 | 1 | 0 | " | 91 | −6.5° |
| 28 | n-$C_{16}H_{33}$ | " | —O— | 1 | n-$C_3H_7$ | OH | 1 | 1 | 1 | 1 | " | 90 | −7.1° |
| 29 | n-$C_{10}H_{21}$ | " | — | 0 | n-$C_5H_{11}$ | OH | 1 | 1 | 1 | 0 | " | 90 | −8.0° |
| 30 | n-$C_8H_{17}$ | ⟨pyrimidinyl-phenyl⟩ | —O— | 1 | n-$C_5H_{11}$ | OH | 1 | 1 | 2 | 0 | —OCO— | 96 | −6.5° |
| 31 | n-$C_{10}H_{21}$ | " | —O— | 1 | n-$C_5H_{11}$ | OH | 1 | 1 | 3 | 0 | " | 85 | −4.1° |
| 32 | n-$C_{10}H_{21}$ | " | —O— | 1 | n-$C_5H_{11}$ | OH | 1 | 1 | 4 | 0 | " | 79 | −8.0° |
| 33 | n-$C_{10}H_{21}$ | " | —O— | 1 | -(CH₂)₃OC₂H₅ | OH | 1 | 1 | 2 | 0 | " | 85 | −7.1° |
| 34 | n-$C_{10}H_{21}$ | " | —O— | 1 | CH₃<br>\|<br>—CHC₂H₅<br>(S) | OH | 0 | 1 | 1 | 0 | " | 88 | +3.8° |
| 35 | n-$C_{10}H_{21}$ | " | —O— | 1 | " | OH | 0 | 1 | 3 | 0 | " | 90 | +5.1° |
| 36 | n-$C_{10}H_{21}$ | " | —O— | 1 | " | OH | 0 | 1 | 4 | 0 | " | 87 | +4.7° |
| 37 | n-$C_{10}H_{21}$ | " | —O— | 1 | Cl CH₃<br>\| \|<br>—CHCHC₂H₅<br>(S) (S) | OH | 0 | 1 | 5 | 1 | " | 89 | −2.3° |

TABLE 5-continued $$Z' = -\left(\!\!\left\langle\!\!\!\bigcirc\!\!\!\right\rangle\!\!\right)_{\!l}\!\!-(\!CH_2\!)_{\!q}\!-\!\!\left(\!\!\begin{array}{c}CH_3\\|\\CH\\*\end{array}\!\!\right)_{\!u}\!\!-$$

| | Aromatic carboxylic acid (IV) | | | | Optically active phenol (V) | | | | | Optically active benzene derivative (I-b) | | |
|---|---|---|---|---|---|---|---|---|---|---|---|---|
| Example | $R_1$ | Ar' | Y | m R' | $R_2$ | u | l | q | s | X | Yield (%) | $[\alpha]_D^{20}$ (c = 1, $CHCl_3$) |
| 38 | n-$C_{10}H_{21}$ | [pyrimidine-phenyl] | -O- | 1 OH | n-$C_3H_7$ | 1 | 1 | 1 | 0 | -COO- | 90 | -7.0° |
| 39 | n-$C_{10}H_{21}$ | " | -O- | 1 OH | n-$C_3H_7$ | 1 | 1 | 2 | 0 | " | 88 | -6.1° |
| 40 | n-$C_8H_{17}$ | " | -O- | 1 OH | n-$C_{12}H_{25}$ | 1 | 1 | 2 | 0 | " | 91 | -5.0° |
| 41 | n-$C_{16}H_{33}$ | " | -O- | 1 OH | n-$C_3H_7$ | 1 | 1 | 2 | 1 | " | 87 | +2.3° |
| 42 | n-$C_{10}H_{21}$ | [pyrimidine-phenyl] | — | 0 OH | n-$C_5H_{11}$ | 1 | 1 | 2 | 0 | -COO- | 92 | -5.5° |
| 43 | n-$C_{10}H_{21}$ | " | -O- | 1 OH | n-$C_3H_7$ | 1 | 1 | 3 | 0 | " | 95 | -6.1° |
| 44 | n-$C_{10}H_{21}$ | [pyrimidine] | — | 0 OH | n-$C_5H_{11}$ | 1 | 2 | 2 | 0 | " | 82 | -8.7° |
| 45 | n-$C_{10}H_{21}$ | [phenyl-pyrimidine] | -O- | 1 OH | n-$C_5H_{11}$ | 1 | 1 | 2 | 0 | " | 86 | -8.0° |
| 46 | n-$C_8H_{17}$ | [phenyl-pyrimidine] | -O- | 1 OH | n-$C_8H_{17}$ | 1 | 1 | 4 | 1 | " | 95 | +2.0° |
| 47 | n-$C_{10}H_{21}$ | [pyrimidine-phenyl] | -O- | 1 OH | $CH_3$<br>\|<br>-$CHC_2H_5$<br>(S) | 0 | 1 | 3 | 0 | " | 85 | +5.1° |
| 48 | n-$C_{10}H_{21}$ | " | -O- | 1 OH | " | 0 | 1 | 4 | 0 | " | 91 | +3.9° |
| 49 | n-$C_{10}H_{21}$ | " | -O- | 1 OH | Cl $CH_3$<br>\| \|<br>-$CHCHC_2H_5$<br>(S) (S) | 0 | 1 | 5 | 1 | " | 91 | -1.8° |

EXAMPLE 53

Into 20 ml of anhydrous dichloromethane were dissolved 1.97 g (6 millimoles) of 2-(4-hydroxyphenyl)-5-decyloxypyrimidine and 1.25 g (5 millimoles) of (+)-4-(1-hexyloxyethyl)benzoic acid, and then 1.22 g (6 millimoles) of N,N'-dicyclohexylcarbodimide and 0.1 g of 4-pyrrolidinopyridine were added thereto, followed by stirring at room temperature for one day. After completion of the reaction, the precipitates were filtered off and then 200 ml of toluene were added thereto, followed by washing with water, 5% acetic acid, water, 5% aqueous sodium hydrogen carbonate solution and water in this order. Then, the organic phase was dried over anhydrous magnesium sulfate. After the solvent was distilled off under reduced pressure, the resulting residue was purified by silica gel column chromatography (eluent; toluene:ethyl acetate) to obtain 2.50 g (yield: 89%) of (+)-4-(5-decyloxy-2-pyrimidyl)phenyl (4-(1-hexyloxyethyl)benzoate.

EXAMPLE 54

Into 20 ml of pyridine were dissolved 1.97 g (6 millimoles) of 2-(4-hydroxyphenyl)-5-decyloxypyrimidine, and then 1.41 g (5 millimoles) of an acid chloride derived from (+)-4-(1-hexanoyloxyethyl)benzoic acid were added thereto, to subject to reaction at 30° to 40° C. for 2 hours. After completion of the reaction, the reaction mixture was poured into 200 ml of water, adjusted to pH 3 to 4 with hydrochlolic acid, followed by extraction with 200 ml of toluene, and the organic phase was washed with water, 5% aqueous sodium hydrogen carbonate solution and water in this order and then the organic phase was dried over anhydrous magnesium sulfate. After the solvent was distilled off under reduced pressure, the resulting residue was purified by silica gel column chromatography (eluent; toluene:ethyl acetate) to obtain 2.76 g (yield: 96%) of 4-(5-decyloxy-2-pyrimidyl)phenyl (+)-4-(1-hexanoyloxyethyl)benzoate.

EXAMPLES 55 TO 73

Reaction and post-treatment were carried out by using the same mole number and the same amount of the solvent as in Example 53 except that the starting material used in Example 53 was placed with those as shown in Table-6, to obtain the results as shown in Table-6.

TABLE 6

$$Z' = -\left(\bigcirc\right)_l - \overset{*}{CH}(CH_3)-(CH_2)_t-$$

| | Phenols (II) | | | | Optically active carboxylic acid compound (III) | | | | | Optically active benzene derivative (I-a) | |
|---|---|---|---|---|---|---|---|---|---|---|---|
| Example | $R_1$ | Ar' | Y | m | $R_2$ | R' | l | t | s | X | Yield (%) | $[\alpha]_D^{20}$ (c = 1, CHCl$_3$) |
| 53 | n-C$_{10}$H$_{21}$ | 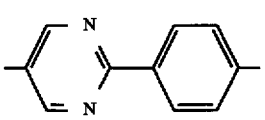 | —O— | 1 | n-C$_6$H$_{13}$ | —OH | 1 | 0 | 0 | —OCO— | 89 | +11.6° |
| 54 | " | " | " | " | n-C$_5$H$_{11}$ | —Cl | 1 | 0 | 1 | " | 96 | +13.1° |
| 55 | n-C$_8$H$_{17}$ | " | " | " | n-C$_{12}$H$_{25}$ | —OH | 1 | 0 | 0 | " | 86 | +9.3° |
| 56 | n-C$_{16}$H$_{33}$ | " | " | " | n-C$_3$H$_7$ | —OH | 1 | 0 | 0 | " | 89 | +8.8° |
| 57 | n-C$_{10}$H$_{21}$ | 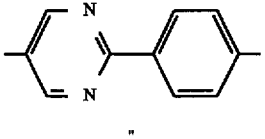 | — | 0 | n-C$_6$H$_{13}$ | —OH | 1 | 0 | 0 | —OCO— | 88 | +10.5° |
| 58 | n-C$_{10}$H$_{21}$ | " | — | 0 | -(CH$_2$)$_3$OC$_2$H$_5$ | —OH | 1 | 0 | 0 | " | 92 | +10.4° |
| 59 | n-C$_{10}$H$_{21}$ | " | 0 | 1 | n-C$_5$H$_{11}$ | —OH | 1 | 1 | 0 | " | 86 | +10.0° |
| 60 | n-C$_{10}$H$_{21}$ | " | 0 | 1 | n-C$_5$H$_{11}$ | —OH | 1 | 2 | 0 | " | 93 | +9.8° |
| 61 | n-C$_{10}$H$_{21}$ | " | 0 | 1 | n-C$_3$H$_7$ | —OH | 1 | 3 | 0 | " | 90 | +10.5° |

| | Aromatic carboxylic acid (IV) | | | | | Optically active phenol (V) | | | | | Optically active benzene derivative (I-b) | |
|---|---|---|---|---|---|---|---|---|---|---|---|
| Example | $R_1$ | Ar' | Y | m | R' | $R_2$ | l | t | s | X | Yield (%) | $[\alpha]_D^{20}$ (c = 1, CHCl$_3$) |
| 62 | n-C$_{10}$H$_{21}$ | 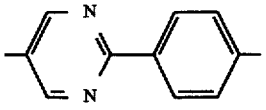 | —O— | 1 | OH | n-C$_6$H$_{13}$ | 1 | 0 | 0 | —COO— | 91 | +10.4° |
| 63 | n-C$_8$H$_{17}$ | " | " | " | " | n-C$_{12}$H$_{25}$ | 1 | 0 | 0 | —COO— | 88 | +10.5° |
| 64 | n-C$_{16}$H$_{33}$ | " | " | " | " | n-C$_3$H$_7$ | 1 | 0 | 0 | —COO— | 87 | +8.1° |
| 65 | n-C$_{10}$H$_{21}$ | " | " | 0 | " | n-C$_6$H$_{13}$ | 1 | 0 | 0 | —COO— | 85 | +11.5° |
| 66 | n-C$_{10}$H$_{21}$ | 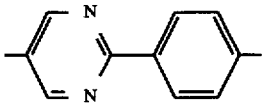 | —O— | 1 | OH | CH$_2$CH$_2$F | 1 | 0 | 0 | —COO— | 88 | +11.2° |
| 67 | n-C$_{10}$H$_{21}$ | " | —O— | 1 | OH | n-C$_5$H$_{11}$ | 1 | 0 | 1 | " | 90 | +10.5° |

TABLE 6-continued $Z' = -\left(\underset{l}{\underset{|}{\bigcirc}}\right)-\underset{*}{\overset{CH_3}{\underset{|}{CH}}}\text{-}(CH_2)_{\overline{j}}$

| 68 | n-$C_{10}H_{21}$ | 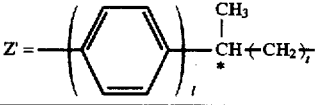 | — | 0 | OH | n-$C_6H_{13}$ | 2 | 0 | 0 | " | 85 | +10.9° |
| 69 | n-$C_{10}H_{21}$ | 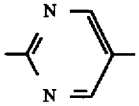 | —O— | 1 | OH | n-$C_6H_{13}$ | 1 | 0 | 0 | " | 89 | +12.0° |
| 70 | n-$C_{10}H_{21}$ | 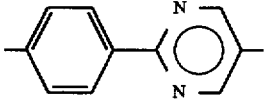 | —O— | 1 | OH | n-$C_5H_{11}$ | 1 | 0 | 1 | " | 92 | +11.2° |
| 71 | n-$C_{10}H_{21}$ | 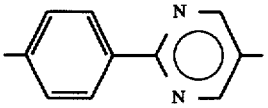 | —O— | 1 | OH | n-$C_5H_{11}$ | 1 | 1 | 0 | " | 88 | +10.0° |
| 72 | n-$C_{10}H_{21}$ | " | —O— | 1 | OH | n-$C_6H_{13}$ | 1 | 2 | 0 | " | 89 | +5.2° |
| 73 | n-$C_{10}H_{21}$ | " | —O— | 1 | OH | n-$C_3H_7$ | 1 | 3 | 0 | " | 90 | +8.1° |

The phase transition temperatures and spontaneous polarization values for representative compounds among those obtained in the above described Examples are shown in Table-7.

TABLE 7

| Compound (of Example No.) | Phase transition temperature | Spontaneous polarization Ps (nc/cm²) |
|---|---|---|
| 53 | $K \xleftrightarrow{26} \overset{*}{Sc} \xleftrightarrow{80} ch \xleftrightarrow{84} I$ | 10 |
| 59 | $K \xleftrightarrow{13} \overset{*}{Sc} \xleftrightarrow{74} ch \xleftrightarrow{94} I$ | 9 |
| 62 | $K \xrightarrow{72} \overset{*}{Sc} \xleftrightarrow{88} S_A \xleftrightarrow{100} I$ | 45 |
| 66 | $K \xrightarrow{85} S_A \xleftrightarrow{108} I$<br>$\overset{*}{Sc} \xleftarrow{}$ | 30 |
| 72 | $K \xleftrightarrow{62} \overset{*}{Sc} \xleftrightarrow{84} S_A \xleftrightarrow{98} I$ | 2 |

EXAMPLES 74 AND 75

Liquid crystal compositions as shown in Table-8 were formulated by using optically active benzene derivative (I) of the present invention. Formulation was carried out by weighing predetermined amounts of predetermined compounds and mixing them in a sample bottle under heating and melting.

[Preparation Method of Liquid Crystal Element]

On a glass substrate provided with indium oxide trsansparent electrodes was provided a polyimide type polymer coating film, followed by rubbing in a predetermined direction by use of gauzes. A liquid crystal cell was assembled by employing glass fibers (diameter: 5 μm) as a spacer so as to maintain the rubbing directions of two pieces of the substrate paralleled and the liquid crystal composition (compound) described above was charged thereinto and sealed under vacuum to obtain a liquid crystal element.

The liquid crystal element was combined with a polarizer and 20 V was applied to the electric field to observe and measure changes in intensity of transmitted light. As a result, it has been confirmed that the liquid crystal element is capable of functioning as a switching element.

TABLE 8

| | Liquid crystalline composition (Value in the parentheses is indicated by % by weight) | Phase transition temperature (°C.) | Spontaneous polarization Ps (nc/cm²) |
|---|---|---|---|
| Comparative example | $C_{10}H_{21}O$—⟨O⟩—⟨O⟩—OCO—⟨O⟩—CHOC$_6$H$_{13}$ with CH$_3$ branch (*)<br><br>Comparative compound 1 (100) | K ⇌⁵⁰ Sc* ⇌⁶⁰ I | 50 |
| Example 23 | Comparative compound 1 (50)<br>Compound in Example 53 (50) | K ⇌⁻¹¹ Sc* ⇌⁶⁴ ch ⇌⁷² I | 70 |
| Comparative example | $C_{10}H_{21}O$—⟨O⟩—COO—⟨O⟩—O(CH$_2$)$_3$CHC$_2$H$_5$ with CH$_3$ branch (*)<br><br>Comparative compound 2 (100) | K —³⁵— Sc* —⁷⁰— S$_A$ —⁷⁴— I | –0 |
| Example 75 | Comparative compound 2 (80)<br>Compound in Example 62 (20) | K —³¹— Sc* —⁶⁰— S$_A$ —⁶⁵— I | 10 |

As is apparent from these results, when the optically active benzene derivatives of the present invention are used as the liquid crystal material, lowering of the temperature range for the Sc* phase can be performed and further spontaneous polarization value can be increased as compared with the single compound in the Comparative example, whereby the response speed can be improved.

We claim:

1. An optically active phenol represented by the formula (V):

$$HO-Z'-O-\left(\overset{O}{\underset{\|}{C}}\right)_s R_2 \quad (V)$$

wherein $R_2$ represents an alkyl or alkoxyalkyl group having 1 to 20 carbon atoms optionally substituted by halogen atoms; Z' represents

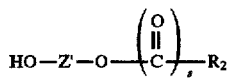

or

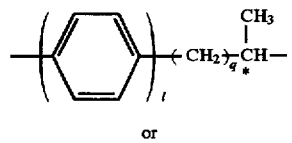

wherein q represents a number of 1 to 5 and * indicates asymmetric carbon, atom; l represents a number of 2; t represents a number of 1 to 5; s represents a number of 0 or 1.

2. An optically active phenol according to claim 1, wherein the carbon number of $R_2$ is 2–20 when t is 1.

3. An optically active phenol according to claim 1, wherein the carbon number of $R_2$ is 5–20 when t is 1 and s is 0.

4. An optically active phenol according to claim 1, wherein the carbon number of $R_2$ is 5–20 when t is 1.

5. An optically active phenol according to claim 1, wherein t is 2–5.

6. An optically active phenol according to claim 1, wherein Z' is

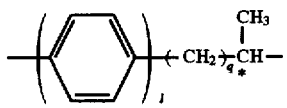

7. An optically active phenol according to claim 1, wherein is 0.

* * * * *